(12) United States Patent
Strohbehn et al.

(10) Patent No.: US 8,425,943 B2
(45) Date of Patent: *Apr. 23, 2013

(54) METHOD OF TREATMENT USING SOLUBILIZED PROTEIN COMPOSITION OBTAINED FROM EGGSHELL MEMBRANE

(75) Inventors: Ronald E. Strohbehn, Nevada, IA (US); Lisa R. Etzel, St. Anthony, IA (US); Jesse Figgins, Ames, IA (US)

(73) Assignee: Biova, L.L.C., Johnston, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/484,537

(22) Filed: May 31, 2012

(65) Prior Publication Data
US 2012/0237495 A1    Sep. 20, 2012

Related U.S. Application Data

(60) Division of application No. 12/508,750, filed on Jul. 24, 2009, now Pat. No. 8,211,477, which is a continuation-in-part of application No. 12/253,719, filed on Oct. 17, 2008, now Pat. No. 8,197,852.

(60) Provisional application No. 60/980,607, filed on Oct. 17, 2007.

(51) Int. Cl.
*A61K 36/54* (2006.01)
*A61K 36/12* (2006.01)

(52) U.S. Cl.
USPC ............................. 424/581; 424/520

(58) Field of Classification Search ............ None
See application file for complete search history.

(56) References Cited

U.S. PATENT DOCUMENTS

| | | | |
|---|---|---|---|
| 5,132,399 A | 7/1992 | Mac Donald et al. | |
| 5,415,875 A | 5/1995 | Kakoki et al. | |
| 6,946,551 B2 | 9/2005 | Long et al. | |
| 7,584,909 B2 * | 9/2009 | Vlad ................ | 241/2 |
| 2004/0180025 A1 | 9/2004 | Long et al. | |
| 2004/0202627 A1 * | 10/2004 | Kuroda et al. ........ | 424/63 |
| 2006/0100177 A1 * | 5/2006 | Nishimura et al. .... | 514/99 |
| 2006/0159816 A1 * | 7/2006 | Vlad ................. | 426/480 |
| 2007/0017447 A1 | 1/2007 | Vlad | |
| 2007/0154575 A1 * | 7/2007 | Shimoda et al. ...... | 424/756 |
| 2007/0172579 A1 | 7/2007 | Blanton et al. | |
| 2007/0178170 A1 | 8/2007 | Devore et al. | |
| 2008/0014282 A1 * | 1/2008 | Long et al. .......... | 424/547 |
| 2011/0020316 A1 | 1/2011 | Minatelli et al. | |
| 2011/0033440 A1 | 2/2011 | Strohbehn et al. | |
| 2011/0034401 A1 | 2/2011 | Strohbehn et al. | |

FOREIGN PATENT DOCUMENTS

| | | |
|---|---|---|
| JP | 59897 | 4/1993 |
| JP | 09040564 | 2/1997 |
| JP | 2004229534 | 8/2004 |
| JP | 2005185658 A | 7/2005 |
| JP | 2006158354 | 6/2006 |

OTHER PUBLICATIONS

Ahlborn, G. J. et al., "Identification of Eggshell Membrane Proteins and Purification of Ovotransferrin and Beta-NAGase from Hen Egg White", The Protein Journal, vol. 25, No. 1, Jan. 2006, pp. 71-81.
Arias, Jose L., et al. "Partial Biochemical and Immunochemical Characterization of Avian Eggshell Extracellular Matrices" Archives of Biochemistry and Biophysics, vol. 298, No. 1, Oct. 1992, pp. 293-302.
Cooke, A.S. et al., "Studies of Membrane, Mammilary Cores and Cuticle of the Hen Egg Shell", Br. Poult. Sci. II, pp. 345-352, 1970.
Kirschbaum, B. B. et al., "Glycoproteines Sulfates des Membranes de L'Oeuf de Poule de et L'Oviducte" Biophysica Acta, 320 (1973) 427-441.
Nakano, K. et al., "Sialic acid contents in chicken eggs and tissues", Canadian Journal of Animal Science, 1994, pp. 601-606.
Nakano, T., et al., "Chemical Composition of Chicken Eggshell and Shell Membranes", 2003 Poultry Science Association, Inc., pp. 510-514.
Wong, Mitchell et al., "Collagen in the Egg Shell Membranes of the Hen", Developmental Biology 104, pp. 28-36, 1984.
Yi, Feng et al., "Natural Bioactive Material: A Preparation of Soluble Eggshell Membrane Protein", Macromolecular Bioscience 2003, 3, pp. 234-237.
Yi, Feng et al., "Soluble eggshell membrane protein: preparation, characterization and biocompatibility" Biomaterials 25 (2004), pp. 4591-4599.
Nternational Search Report, Biova, LLC, PCT/US2008/080336, April 6, 2009, 2 pages.

\* cited by examiner

*Primary Examiner* — Chris R Tate
(74) *Attorney, Agent, or Firm* — McKee, Voorhees & Sease, P.L.C.

(57) ABSTRACT

The process for solubilizing proteinaceous material of the present invention includes subjecting the proteinaceous material to a sufficient amount of a basic solution to obtain a supernatant that has a basic pH and exposing the supernatant to the basic solution for a sufficient length of time and temperature for hydrolysis to occur. The process also includes cooling the mixture of the supernatant and proteinaceous material and optionally acidifying the mixture. This process may also include recovering the solubilized protein from the supernatant for use in various applications. Also provided herein is a composition of solubilized proteins from eggshell membrane obtained using processes of the present invention.

12 Claims, 28 Drawing Sheets

Excess Sebum Pore Count: 814

Acne Pore Count: 1993

Pore Count: 1389

Pore Count: 18

Effect of BiOvaDerm™ Cream on Wrinkles and Facial Redness

SUBJECT BVA 3 - JE 7:

Photo Scans. In areas sampled for analysis, Dark Blue lines indicate computer assignment of deep wrinkles; Light Blue lines are fine lines; Gray Lines are emerging wrinkles.

JE January 30 Before cream use. 100% Reference image.

JE February 27 BiOvaDerm™-- After 4 Weeks Daily Use of BiOvaDerm™ Face Cream

JE March 27 BiOvaDerm™-- After 4 Weeks Cessation of BiOvaDerm™ Face Cream Use

SUBJECT BVA 3 - SG:

Photo Scans. Acne progression in subject using cream for 1 week (cream stopped at 2/28/2009)

Just Before cream use. 100% Reference image- Acne.

BiOvaDerm™-- After 1 Week Daily Use of BiOvaDerm™ Face Cream

BiOvaDerm™-- After 4 Weeks Cessation of BiOvaDerm™ Face Cream Use

| STUDY SCHEDULE | | | | |
|---|---|---|---|---|
| Assessment | Visit-1 Screening Baseline | Visit-2 Week-2 Evaluation | Visit-3 Week-4 Evaluation | Visit-4 Week-6 Evaluation |
| Informed-Consent | S/T | | | |
| Medical-History | S/T | | | |
| Medication-History | S/T | | | |
| Lab-Asmt & Blood Work | S/T | | | S/T |
| Pain-Assessment Score | S/ | | | |
| Range of Motion | S/ | S | S | S |
| Pain-Assessment Score | | S | S | S |
| Treatment Adverse Events | | S/T | S/T | S/T |
| Review-Diary Entries | | S/T | S/T | S/T |
| Termination | | S/T | S/T | S/T |
| S.Scan for Tone | T | T | T | T |
| S.Scan for Moisture | T | T | T | T |
| S.Scan for Blemishes | T | T | T | T |
| S.Scan for Wrinkles | T | T | T | T |
| BP, HR, Height/Weight | T | T | T | T |

FIG. 20

METHOD OF TREATMENT USING SOLUBILIZED PROTEIN COMPOSITION OBTAINED FROM EGGSHELL MEMBRANE

CROSS-REFERENCE TO RELATED APPLICATIONS

This application is a Divisional application of U.S. Ser. No. 12/508,750 filed Jul. 24, 2009, which is a Continuation-in-Part of U.S. Ser. No. 12/253,719 filed Oct. 17, 2008 which claims priority under 35 U.S.C. §119 of a provisional application Ser. No. 60/980,607 filed Oct. 17, 2007, all of which are hereby incorporated by reference in their entirety.

BACKGROUND OF THE INVENTION

Many industrial waste products such as pigskin, fish scale, and avian eggshell membranes are a source of valuable bioactive materials, including collagen, that have widespread applications in medical, health and cosmetic industries. To date, a major drawback to their use has been the difficulty in solubilizing these proteinaceous starting materials in a sufficiently stable and active pure form at an industrial scale so that high yield is achieved in an economic manner.

For example, solubilization of eggshell membranes has proven technically difficult. Recent processes to solubilize eggshell membranes include the use of mercaptopropionic acid, various extraction agents, or enzymes, such as peptidases, trypsin, and collagenases; however, problems have been associated with these procedures. The amount of protein solubilized from the starting material by these processes is low, the techniques are not cost-effective, and often the recovered protein components do not maintain their native activity. Therefore an inexpensive process for solubilizing eggshell membranes and other sources of proteinaceous materials while maintaining both yield, purity and activity of the solubilized protein is needed, particularly one suited for commercial scale implementation.

BRIEF SUMMARY OF THE INVENTION

The present invention relates to a process to provide for commercial-scale solubilization of various components from a proteinaceous material such as eggshell membranes. As a result of the present invention, one can produce a composition having large amounts of solubilized proteins from eggshell membranes. This process has an additional advantage in that the resulting composition may be used as a source for the isolation of other valuable components. Specific components, such as individual proteins, may be further purified from the composition thereby making it feasible to isolate proteins of interest from the composition.

The process for solubilizing proteinaceous material of the present invention includes subjecting the proteinaceous material to a sufficient amount of a basic solution for a sufficient length of time and temperature for hydrolysis to occur. The process also includes cooling the mixture of proteinaceous material/basic solution, and, if desired acidifying the mixture, to obtain solubilized proteins. This process may also include recovering the solubilized proteins from the mixture for use in various applications.

Therefore it is a primary object feature or advantage of the present invention to improve over the state of the art.

A further object, feature, or advantage of the invention is to provide a novel process for the solubilization of a proteinaceous material.

A further object, feature, or advantage of the invention is to provide a process for the solubilization of a proteinaceous material that produces solubilized protein that can be used in medical, cosmetic, pharmaceutic, dermatological or nutritional applications.

Another object, feature, or advantage of the invention is to provide a process for the solubilization of a proteinaceous material that substantially lowers the mineral (ash) content of the solubilized protein composition.

Yet another object, feature, or advantage of the invention is to provide a process for the solubilization of a proteinaceous material that increases the yield of the solubilized protein composition.

An object, feature, or advantage of the present invention is to provide a means to solubilize proteins from eggshell membranes.

It is a further object, feature, or advantage of the present invention is to provide a composition of solubilized proteins from eggshell membranes.

Yet another object, feature, or advantage of the invention is to provide a composition that is rich in proteins solubilized from eggshell membranes.

Still another object, feature, or advantage of the invention is to provide a cosmetic, medical, pharmaceutic, dermatological, or nutritional composition that is rich in proteins solubilized from eggshell membranes.

An object, feature, or advantage of the present invention is to provide a composition useful in treating an individual in need of proteins solubilized from eggshell membranes.

An additional object, feature, or advantage of the present invention is to provide a method of treating an individual in need of proteins solubilized from eggshell membranes.

A further object, feature, or advantage of the present invention is to provide a process for preparing a composition that has solubilized proteins obtained from an eggshell membrane.

A still further object, feature, or advantage of the present invention is to provide a process which is suitable for implementation on a commercial/industrial scale.

One or more of these and/or other objects, features, or advantages of the present invention will become apparent from the specification and claims that follow. No single embodiment of the invention need fulfill all or any of the objects stated herein.

BRIEF DESCRIPTION OF THE DRAWINGS

In the bar graphs, the results for BIO1 are shown in the bar positioned to the left of a bar, which shows the results for BIO2.

As used herein, BIO1 refers to an eggshell membrane composition obtained as a 3 kDa permeate using a 3 kDa membrane and nanofilter using the methods described herein. SKU313 and 314 refer to a spray dried form of BIO1 and freeze dried form of BIO1. See also Example 5 for further details.

As used herein, BIO2 refers to an eggshell membrane composition obtained as a 3 kDa retentate using a 3 kDa membrane using the methods described herein. SKU309, OvaCore, BiOvaCore, OvaFlex, BiOva Flex, OvaDerm, BiOvaDerm all refer to a spray dried form of BIO2. See also Example 5 for further details.

Figure 1:
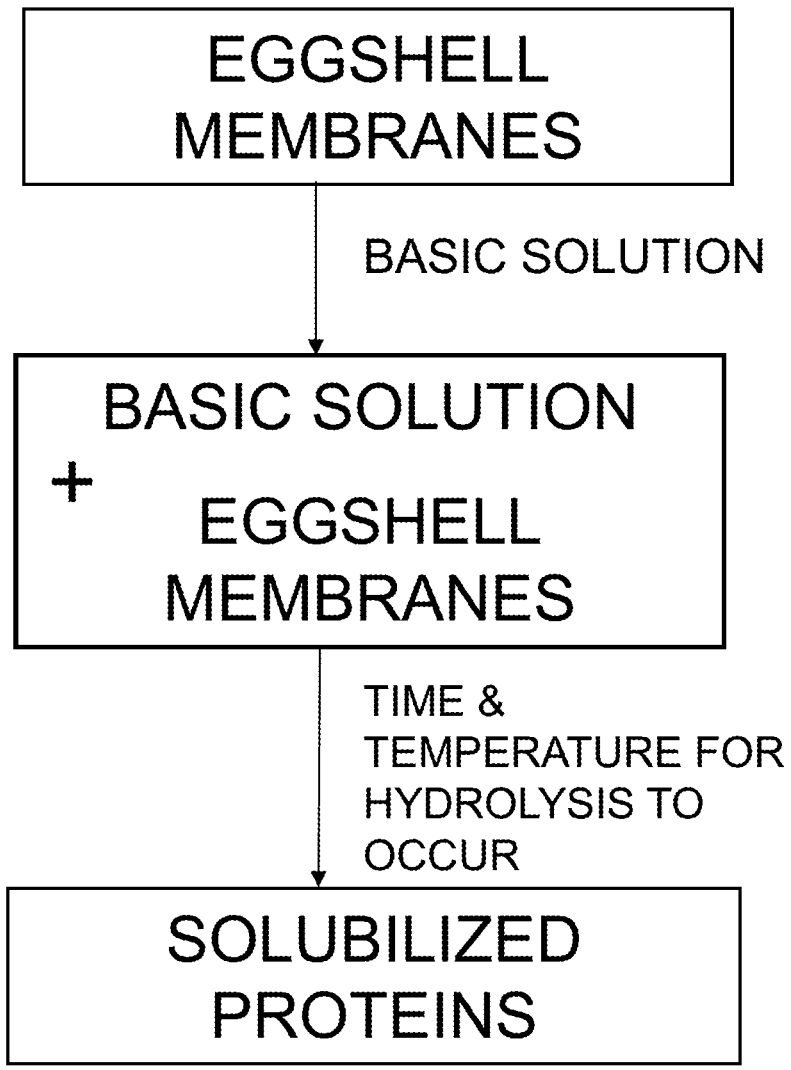

FIG. 1 is a flow chart for one embodiment of a process for solubilizing eggshell membranes.

Figure 2:
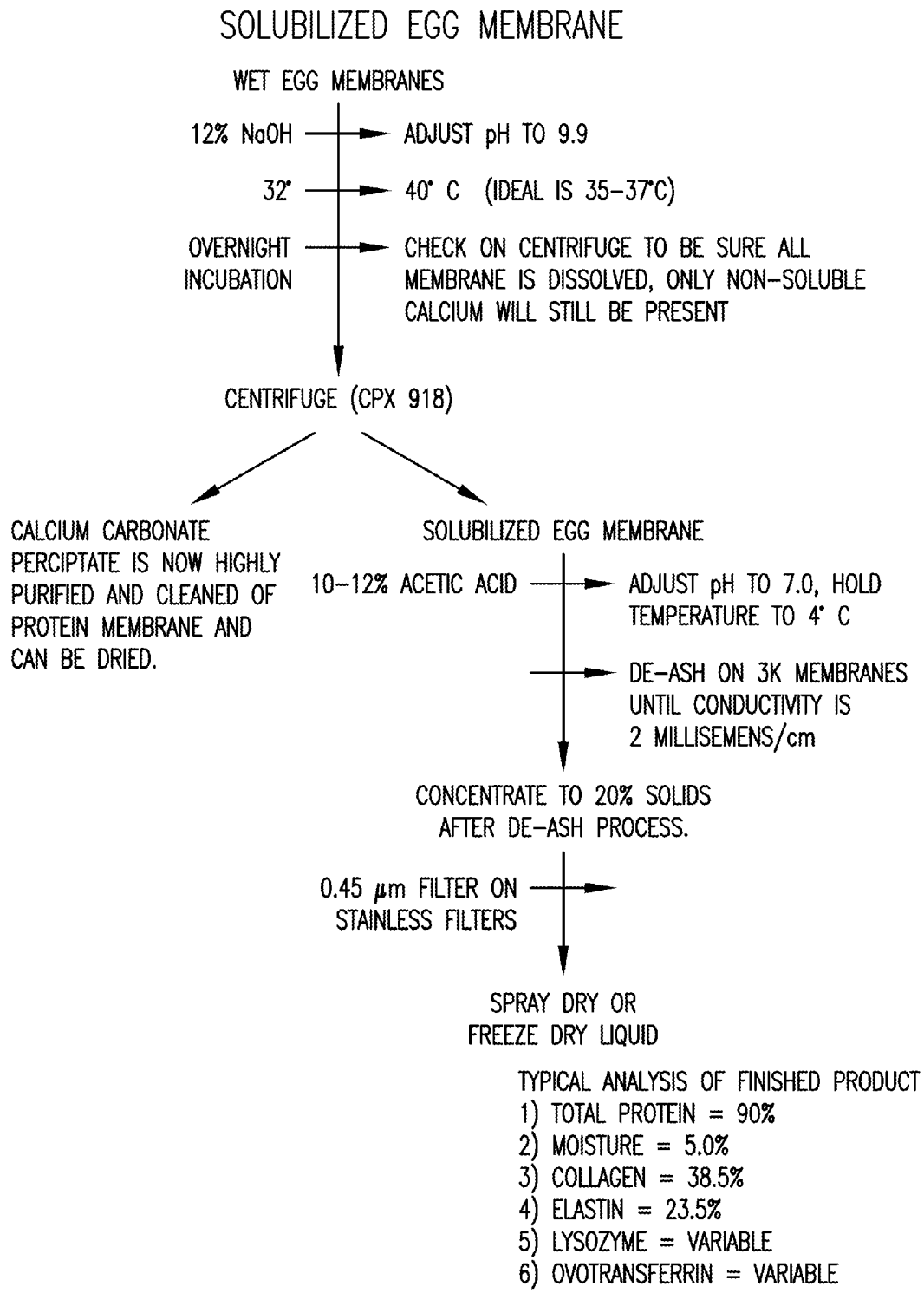

FIG. 2 is a flow chart for one embodiment of a process for solubilizing eggshell membranes.

Figure 3A:
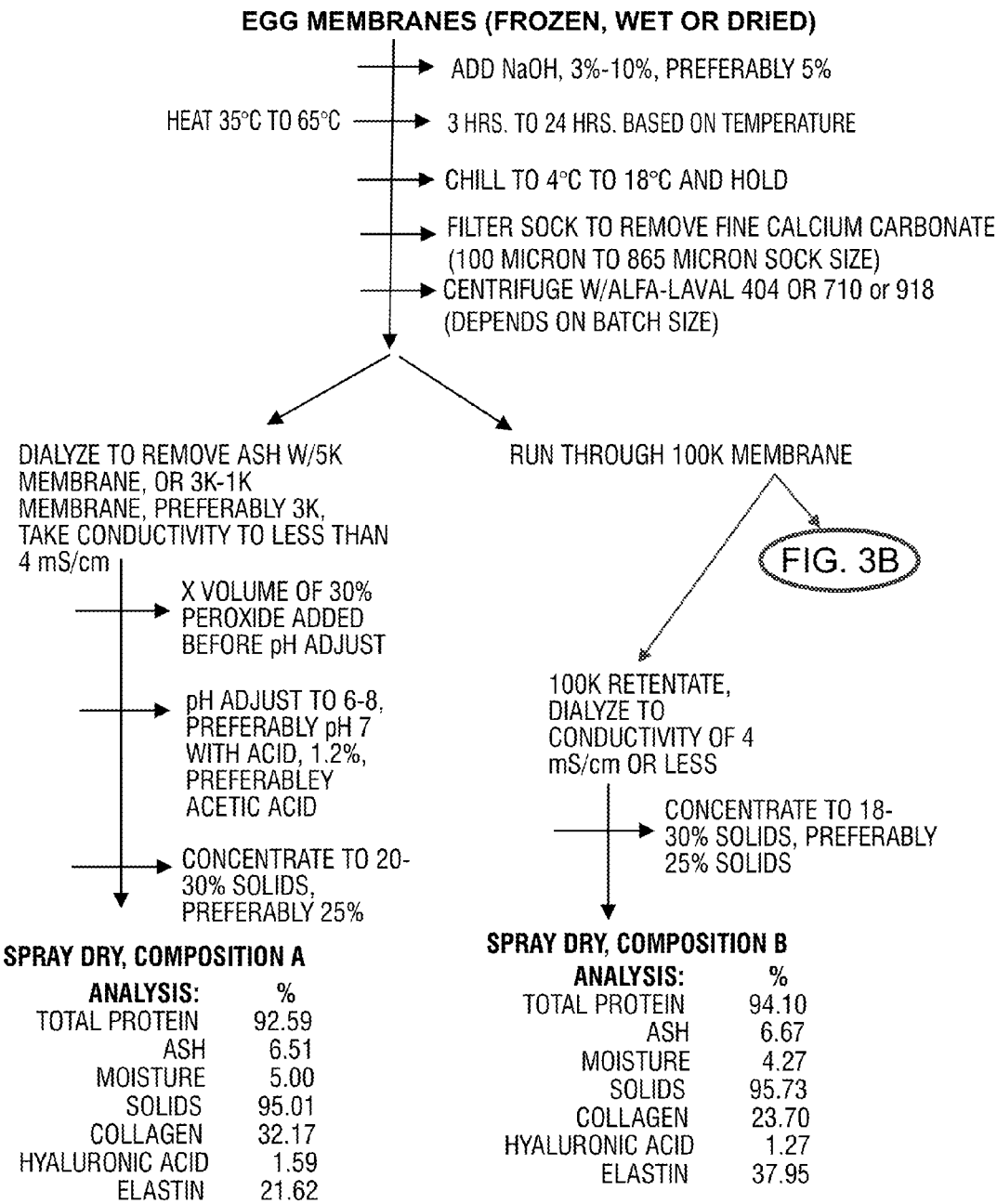
Figure 3B:
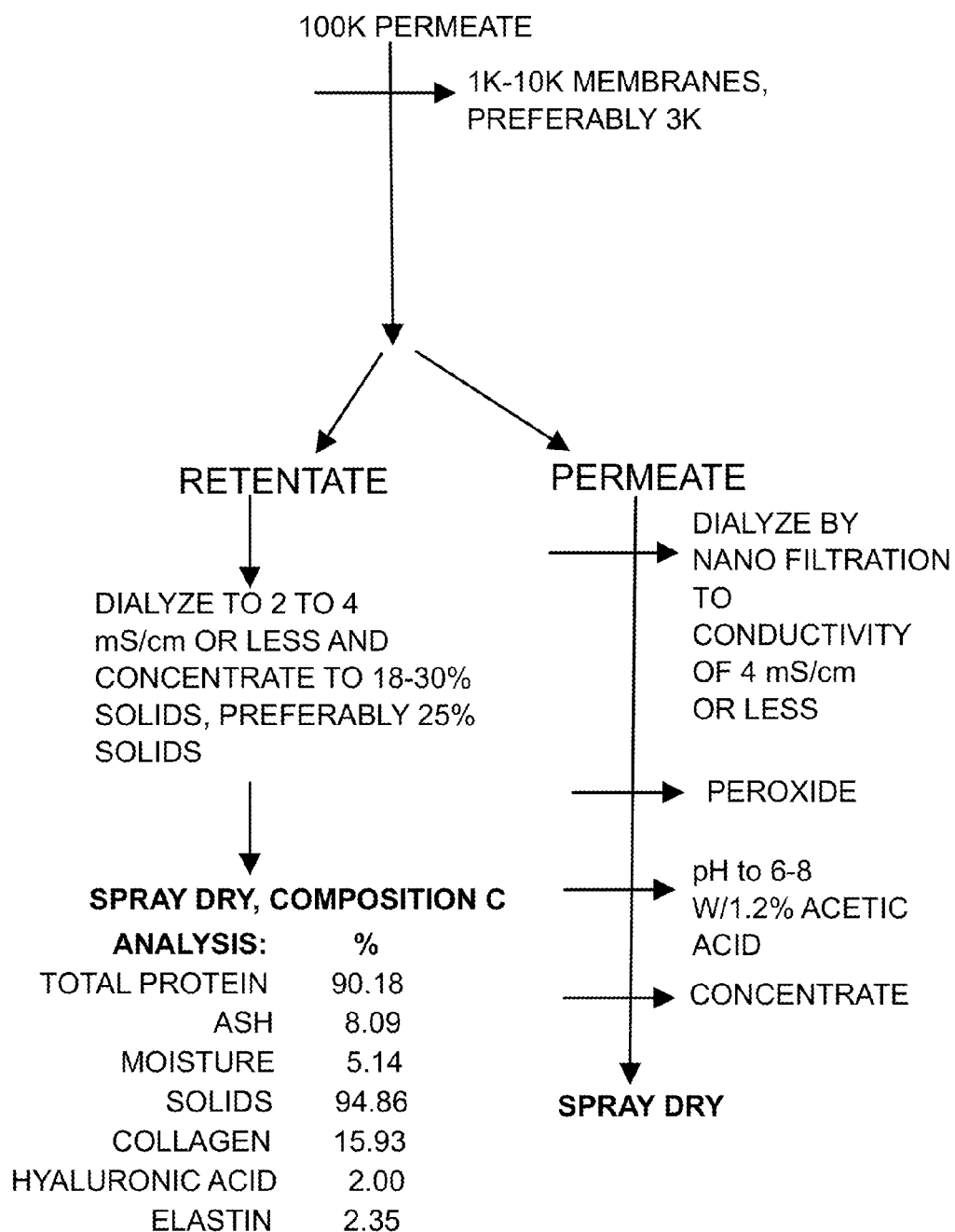

FIGS. 3A and 3B are flow charts for one embodiment of a process for solubilizing eggshell membranes.

Figure 4:
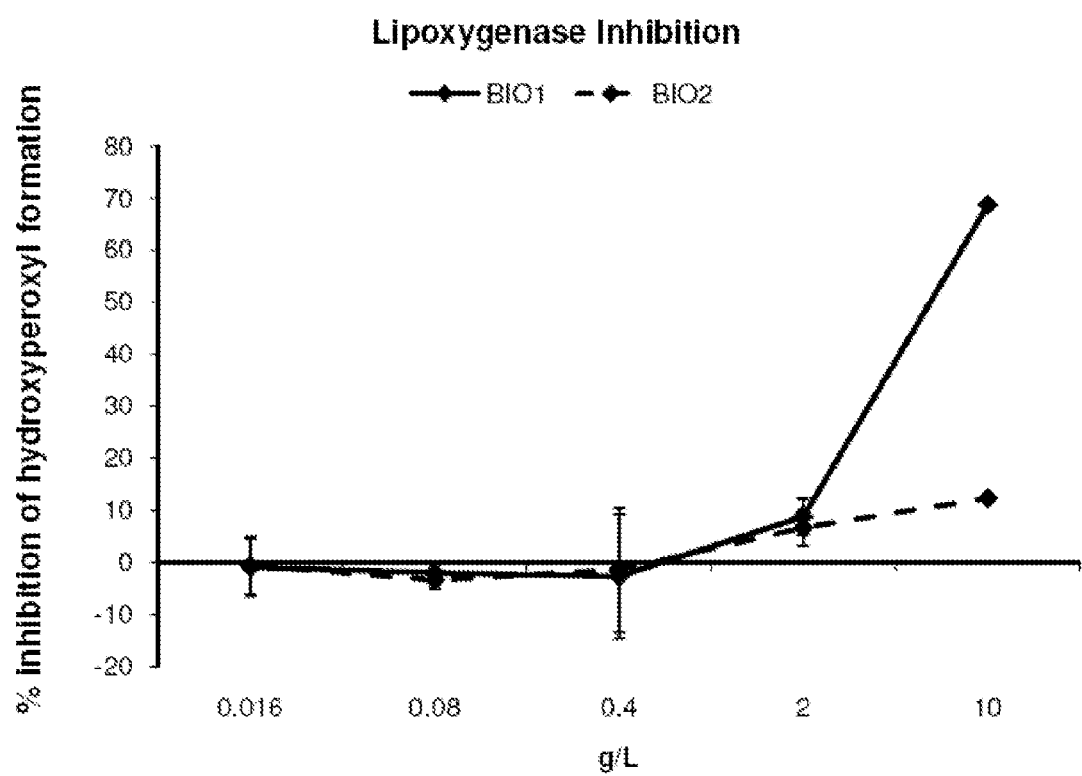

FIG. 4 is a graph showing the ability of the BIO1 and BIO2 fractions to inhibit the peroxyl free radical production by the enzymatic activity of Lipoxygenase.

Figure 5A:
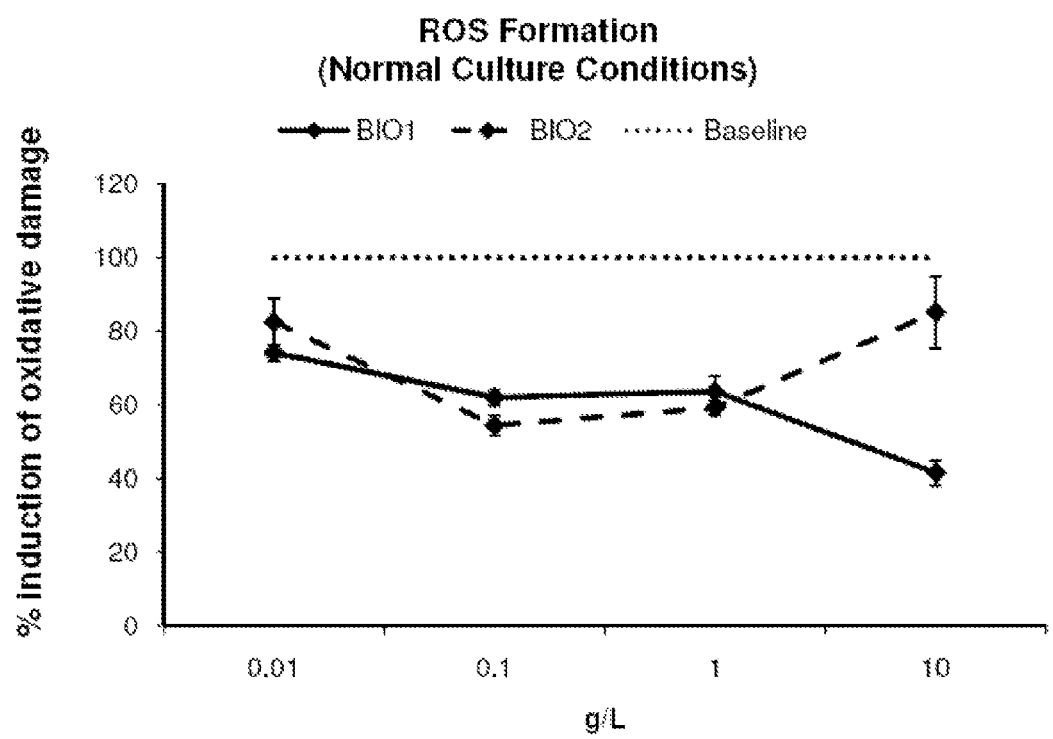
Figure 5B:
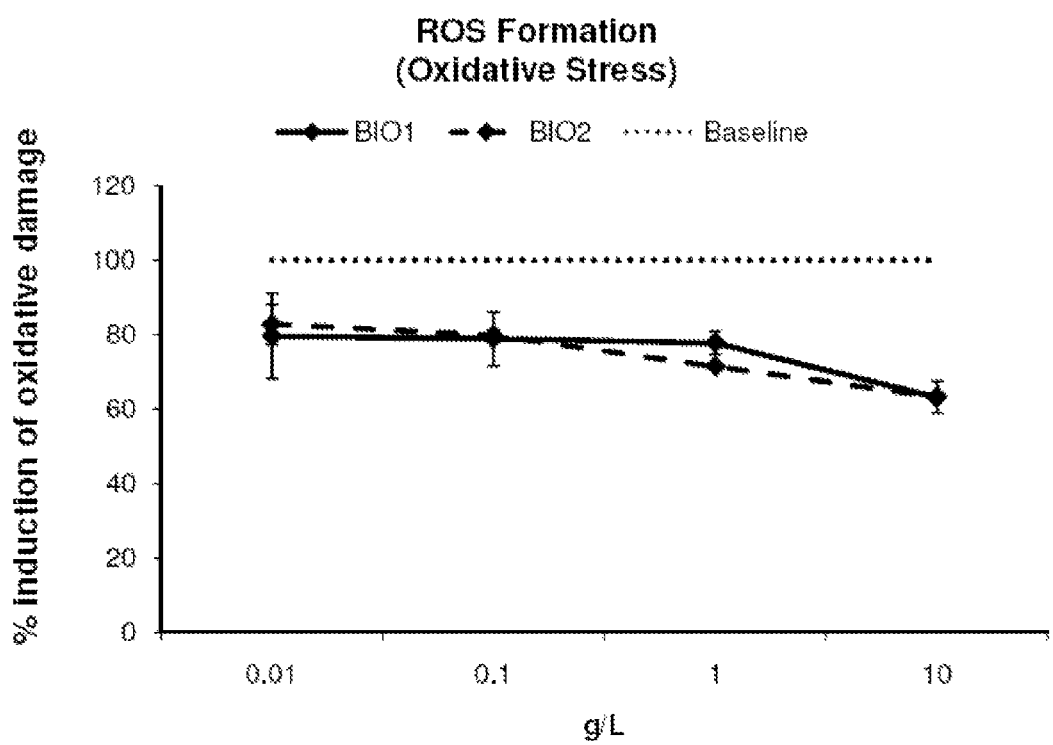

FIGS. 5A and 5B are graphs showing the ability of the BIO1 and BIO2 fractions to inhibit formation of Reactive Oxygen Species (ROS) in human PMN cells under normal culture conditions (5A) and under conditions of oxidative stress (5B).

Figure 6A:
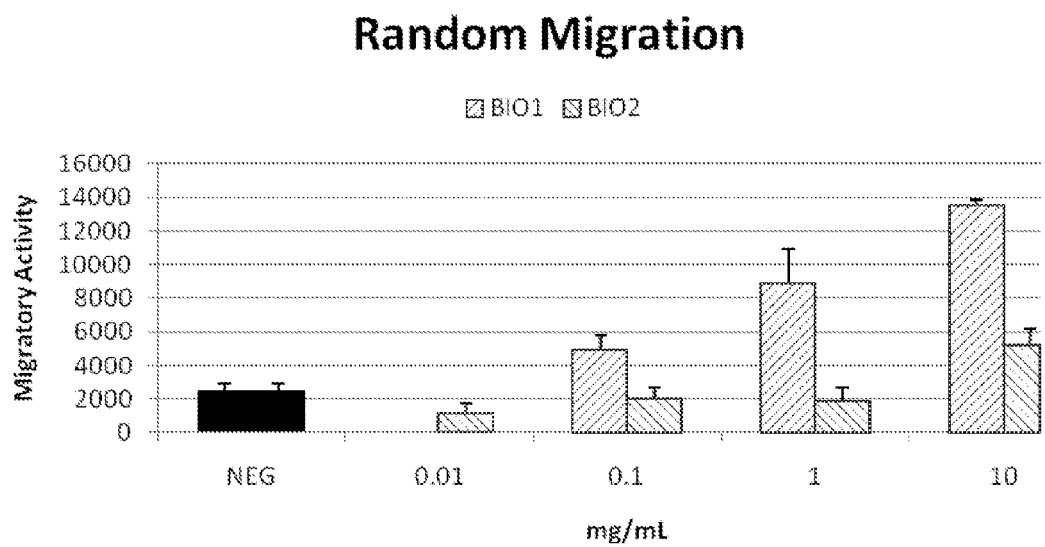
Figure 6B:
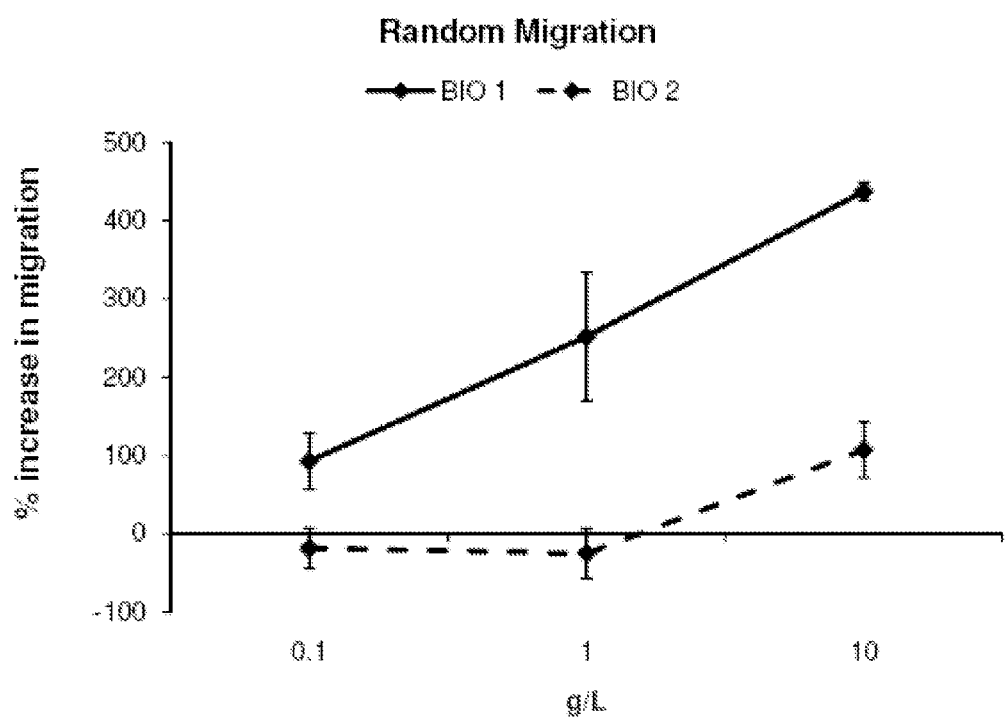
Figure 6C:
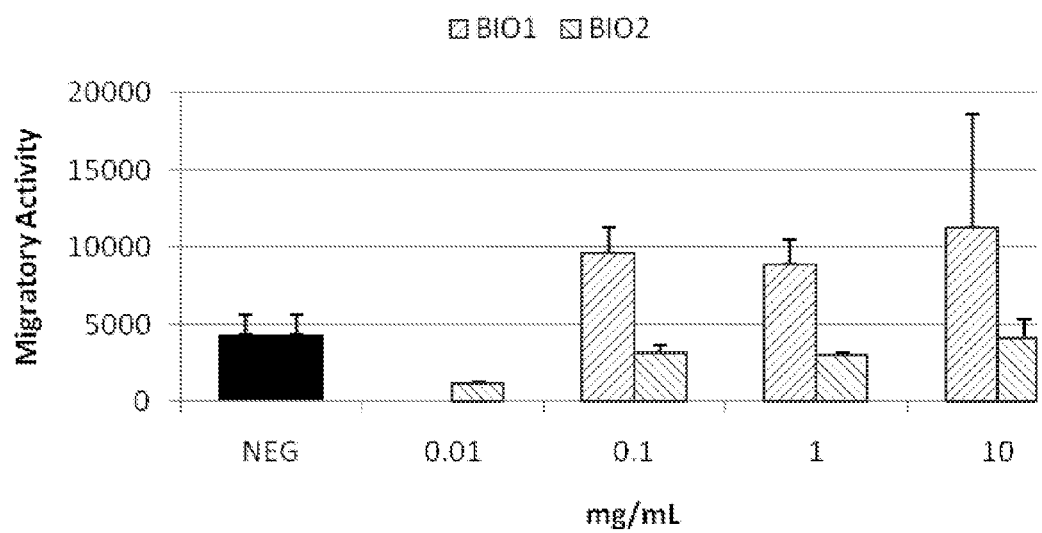
Figure 6D:
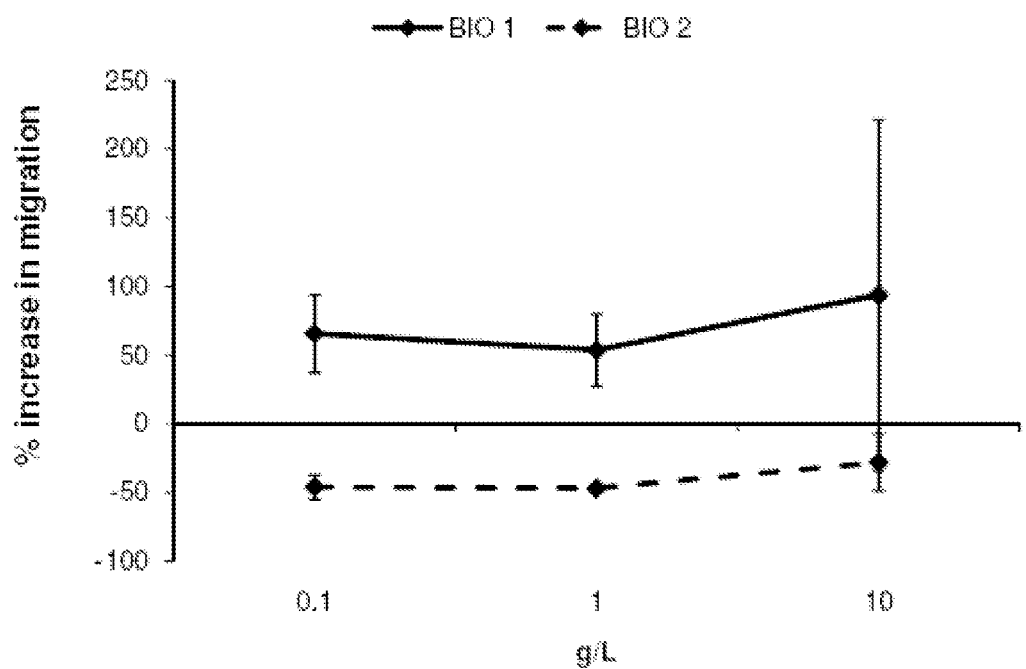

FIGS. 6A and 6B are graphs showing the ability of the BIO1 and BIO2 fractions to support random migration behavior of human PMN cells. *BIO2 was tested at one more serial dilution, due to extra plate space in all migration experiments*

FIGS. 6 C and 6D are graphs showing the ability of the BIO1 and BIO2 fractions to inhibit the directed migration of PMN cells towards the inflammatory chemoattractant Leukotriene B4 (LTB4). *BIO2 was tested at one more serial dilution, due to extra plate space in all migration experiments*

Figure 6E:
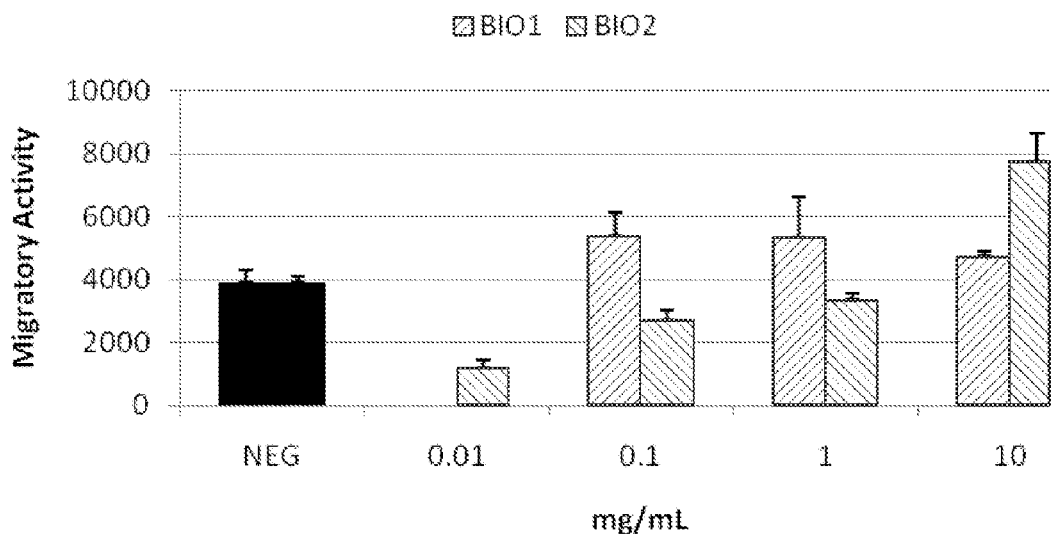

FIG. 6E is a graph showing the ability of the BIO1 and BIO2 fractions to inhibit the directed migration of PMN cells towards the inflammatory chemoattractant Interleukin-8 (IL-8). *BIO2 was tested at one more serial dilution, due to extra plate space in all migration experiments*

Figure 6F:
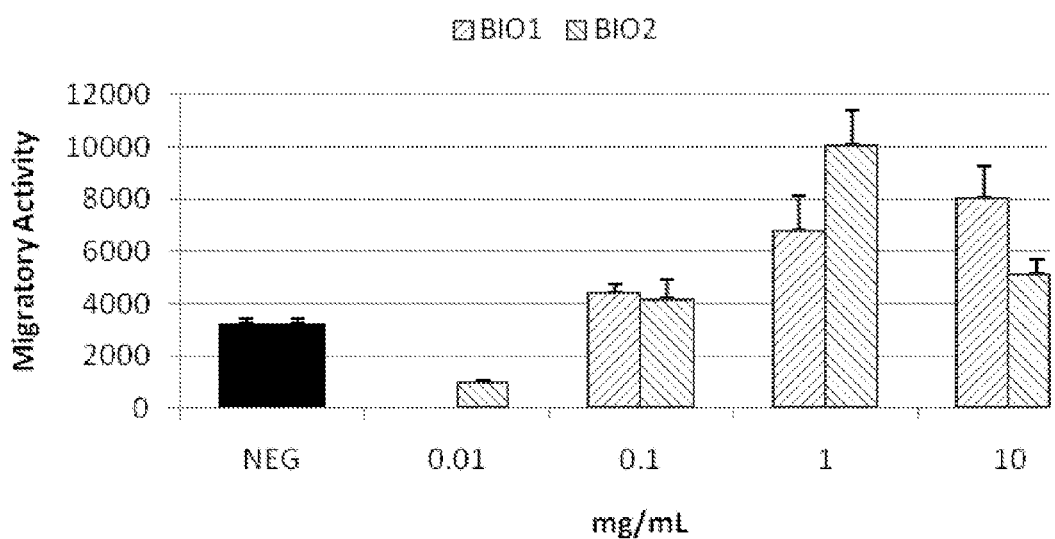

FIG. 6F is a graph showing the ability of the BIO1 and BIO2 fractions to inhibit the directed migration of PMN cells towards the inflammatory chemoattractant f-MLP. *BIO2 was tested at one more serial dilution, due to extra plate space in all migration experiments*

Figure 7A:
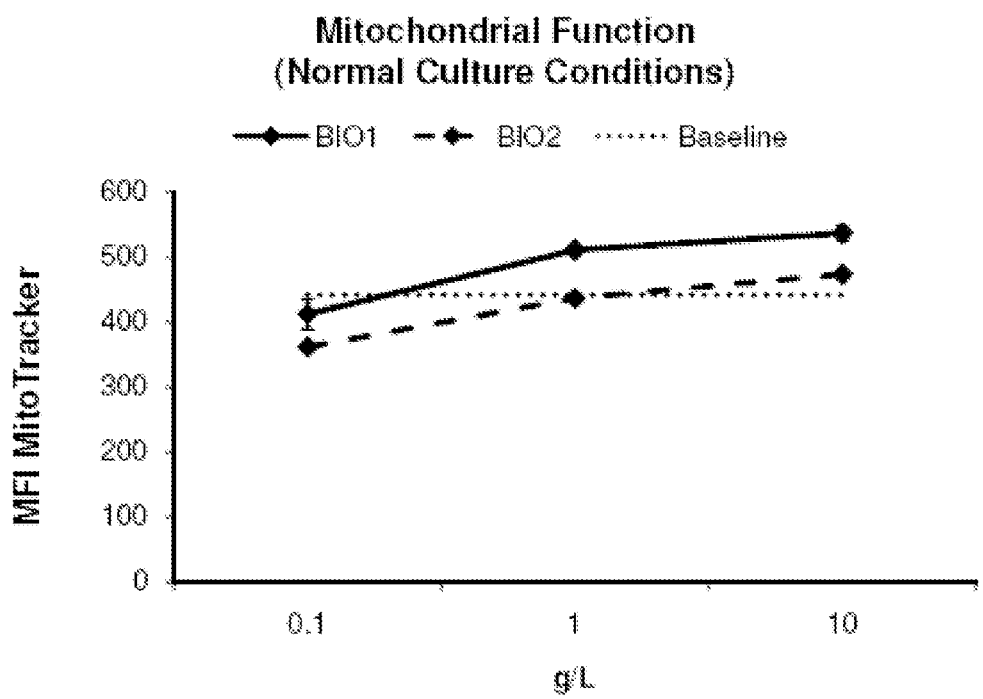
Figure 7B:
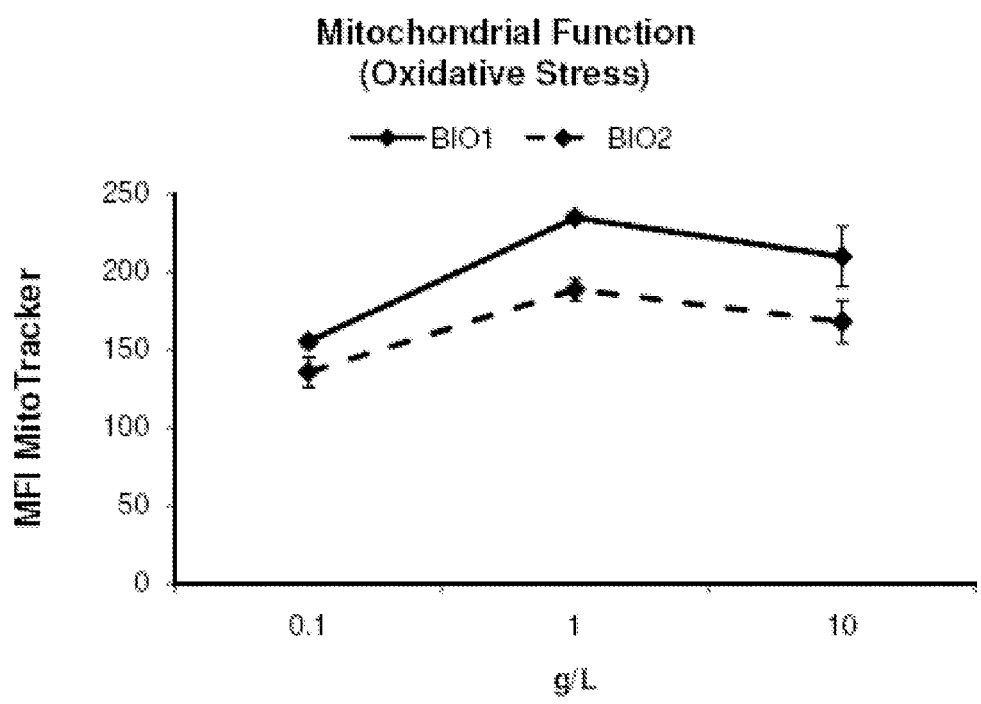

FIGS. 7A and 7B are graphs showing the ability of the BIO1 and BIO2 fractions to support mitochondrial function under normal culture conditions (A) and under conditions of oxidative stress (B). The testing was performed where each testing condition, including each serial dilution of test product, was performed in triplicate. The experiment was repeated three times using PBMC from different blood samples.

Figure 8A:
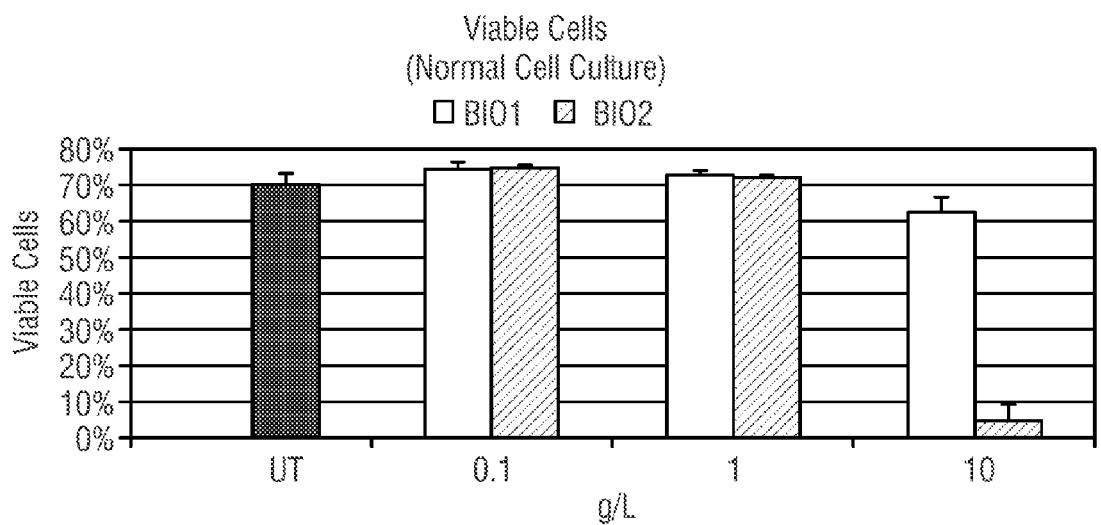
Figure 8B:
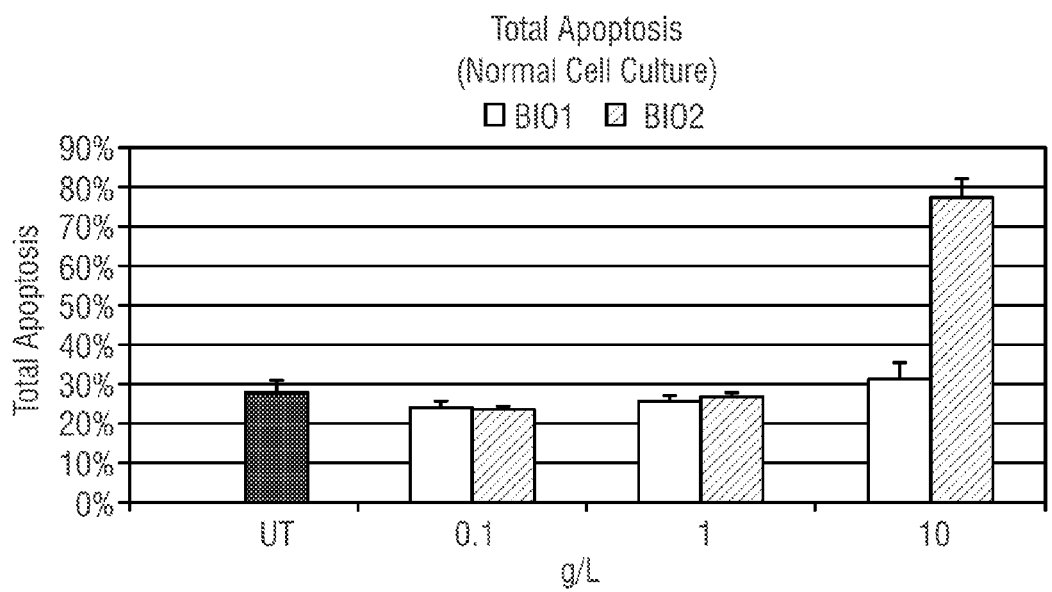
Figure 8C:
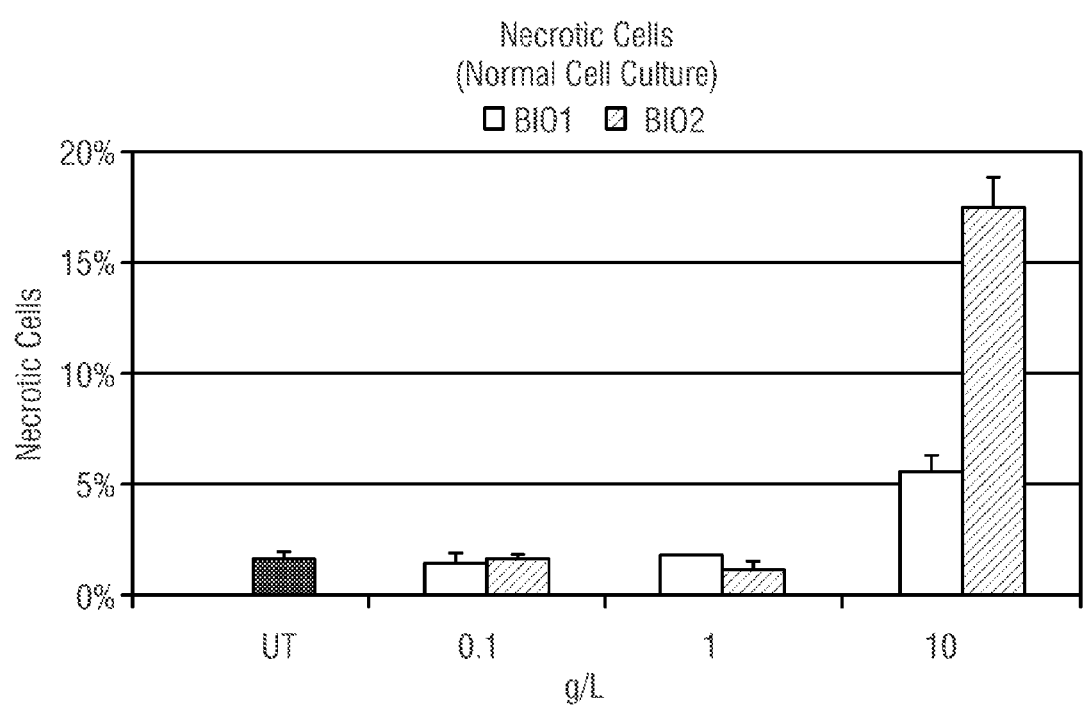

FIGS. 8A, 8B, and 8C are graphs showing the viability of cells under normal culture conditions (8A) in the presence of BIO1 and BIO2, and the ability of the BIO1 and BIO2 fractions to protect human PBMC from necrotic (8C) and apoptotic (8B) cell death under normal cell culture conditions.

Figure 9A:
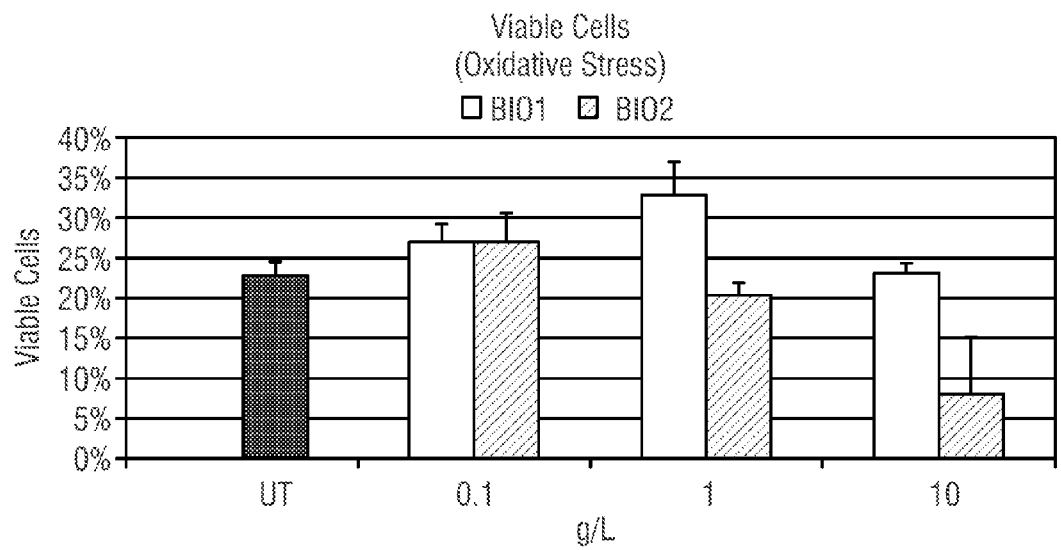
Figure 9B:
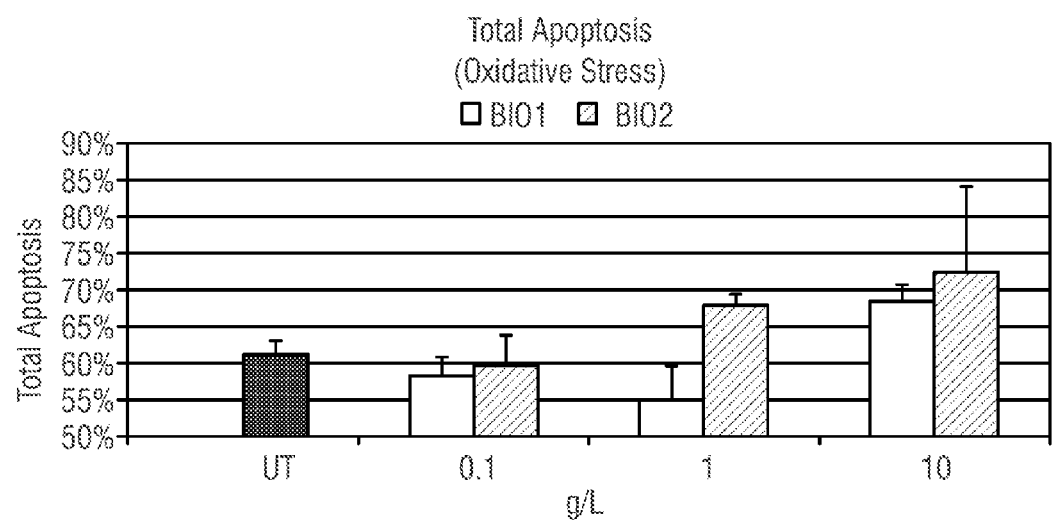
Figure 9C:
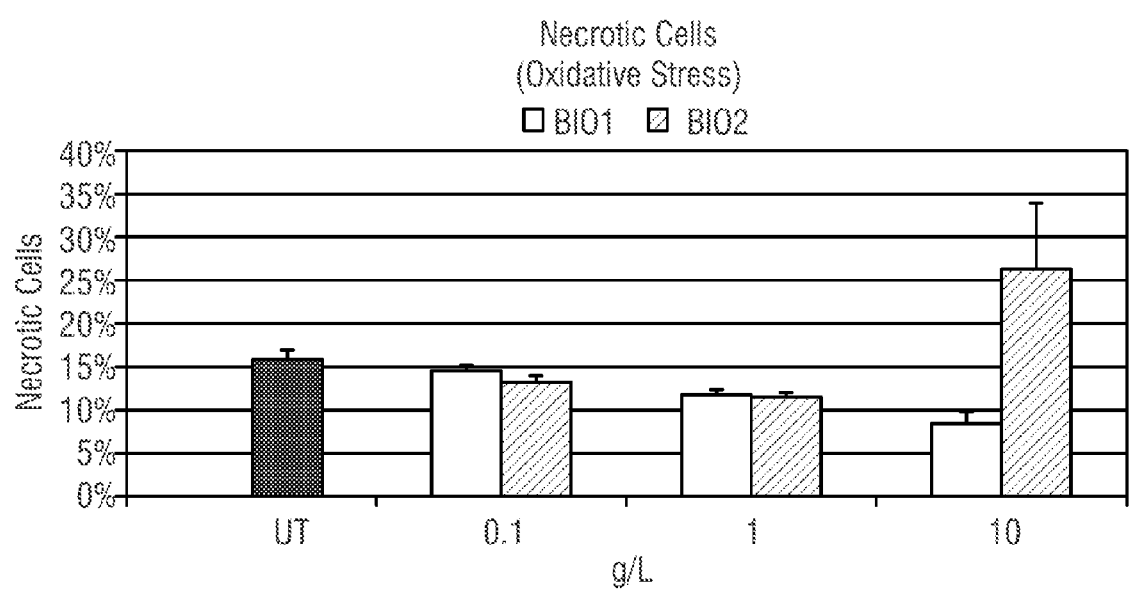
Figure 10A:
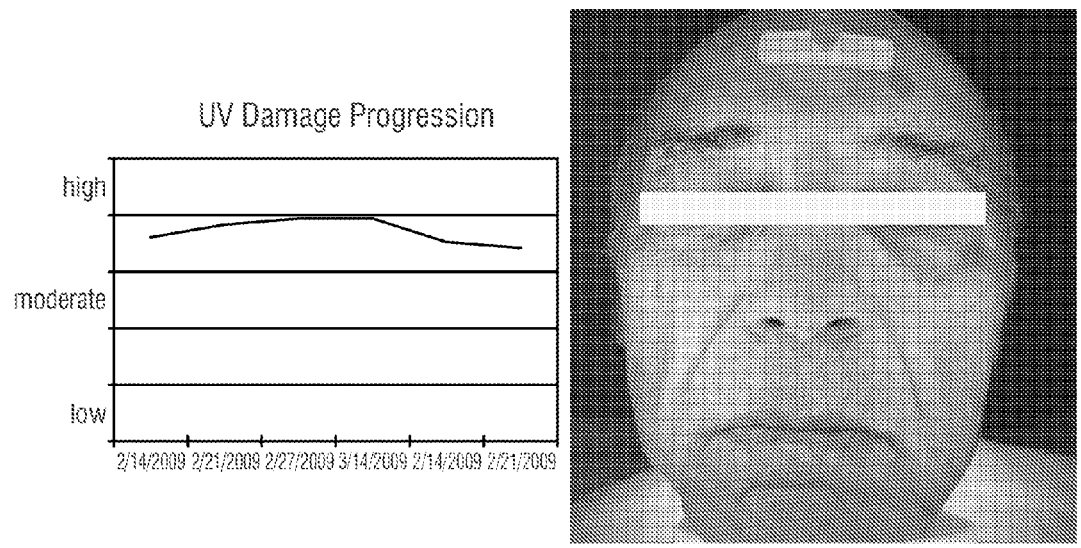
Figure 10A:
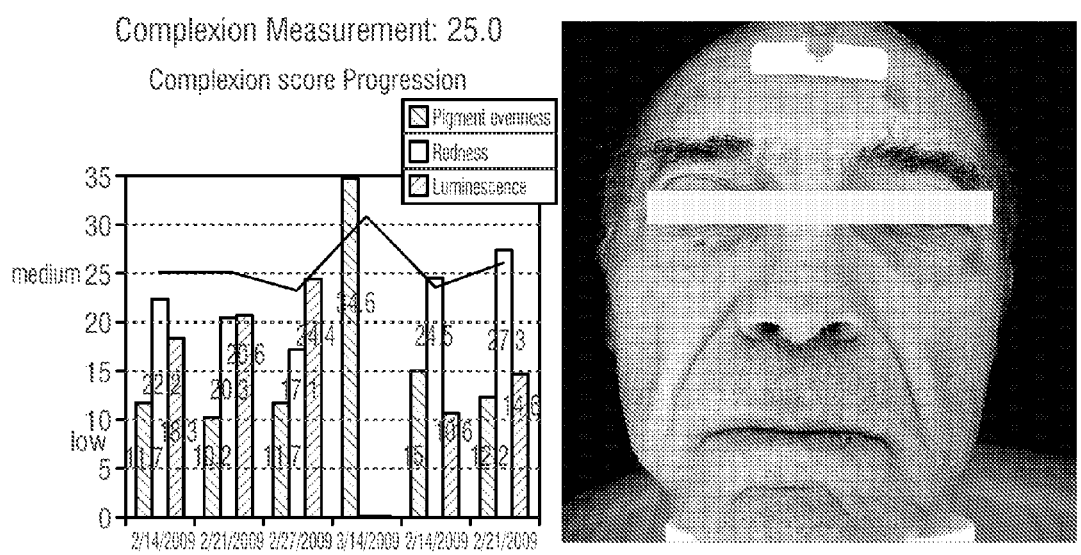
Figure 10B:
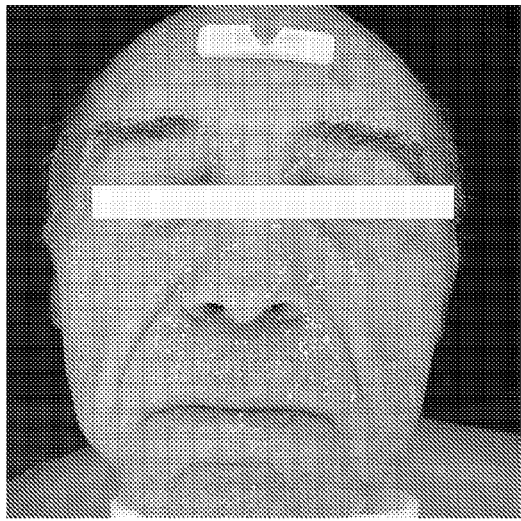
Figure 10B:
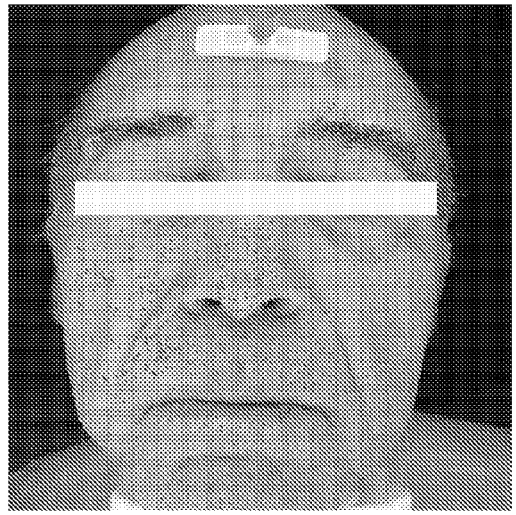
Figure 10B:
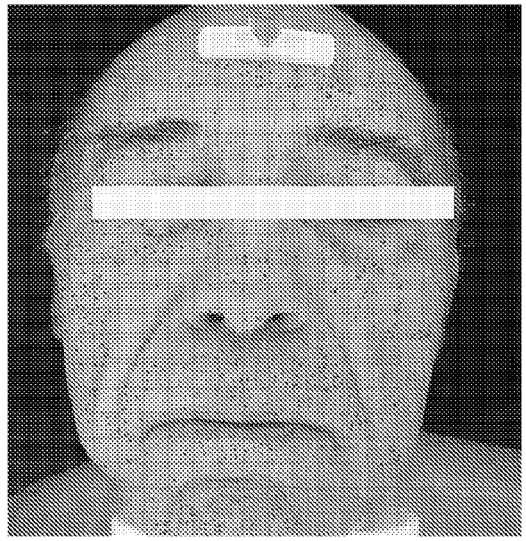
Figure 10B:
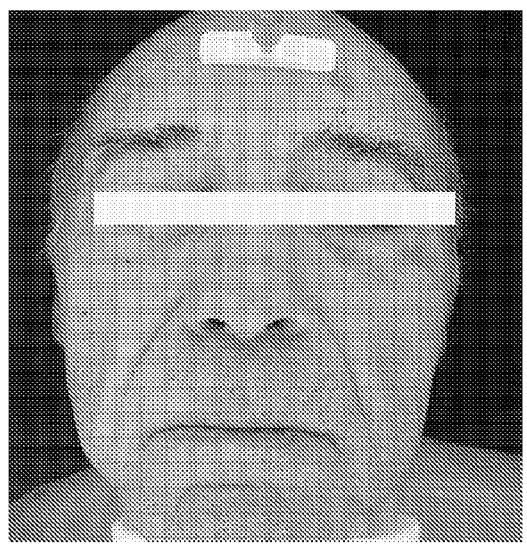
Figure 10C:
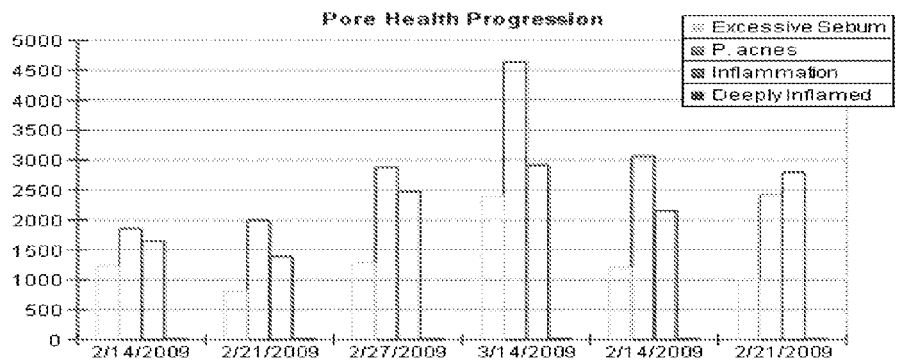
Figure 10C:
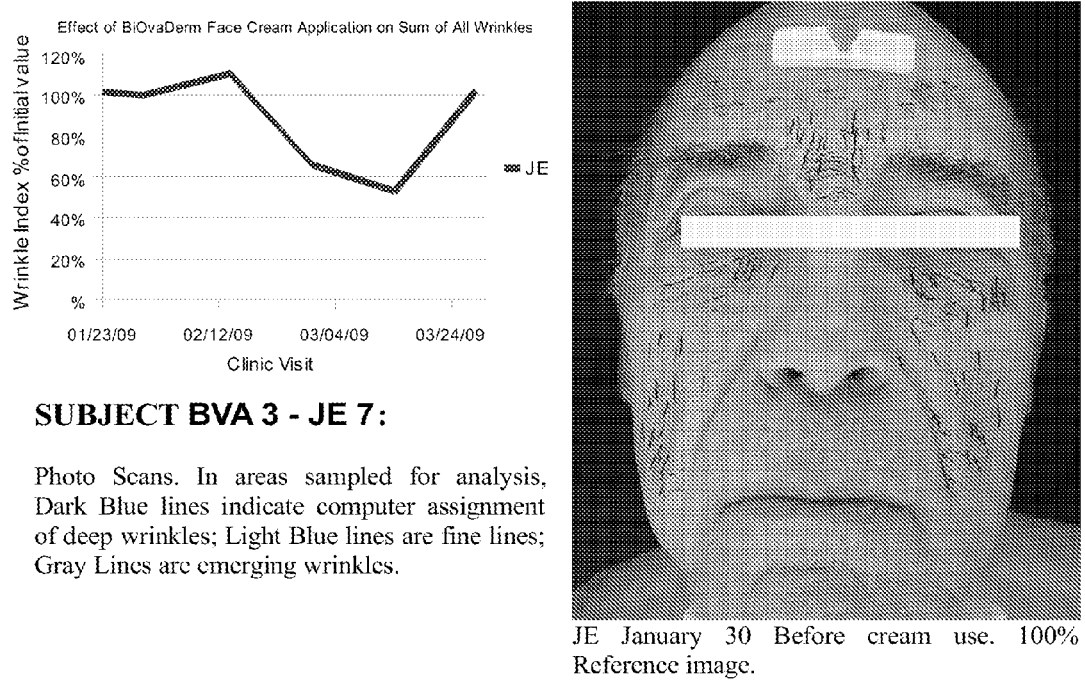
Figure 10D:
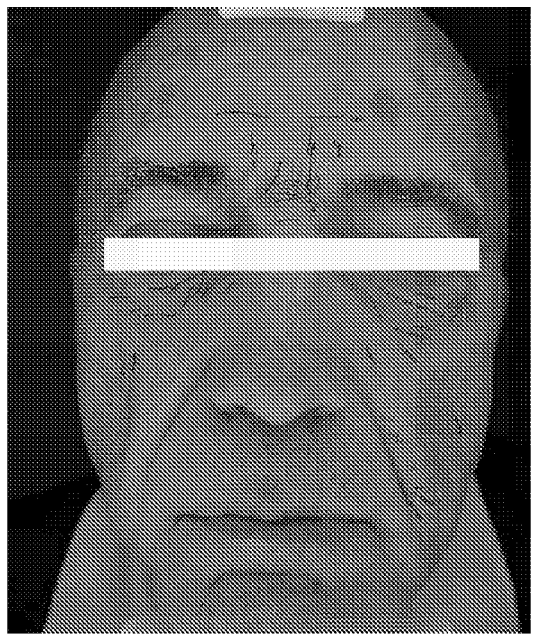
Figure 10D:
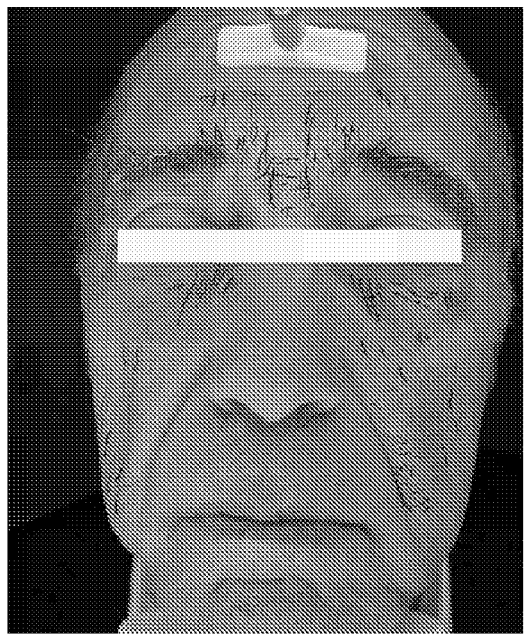
Figure 10E:
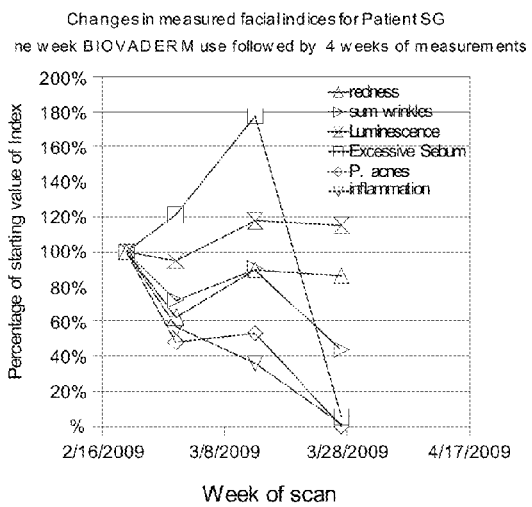
Figure 10E:
Figure 10F:
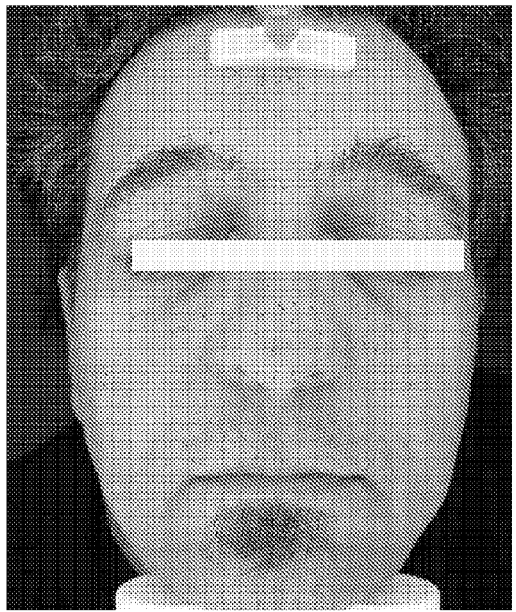
Figure 10F:

FIGS. 9A, 9B, and 9C are graphs showing the viability of cells under oxidative stress (9A) in the presence of BIO1 and BIO2, and the ability of the BIO1 and BIO2 fractions to protect human PBMC from necrotic (9C) and apoptotic (9B) cell death under oxidative stress.

FIG. 10A-F shows examples of data output from the Moritex/BTBP Skin Analyzer. A dataset illustrated by the example above was collected at each time point (clinic visit) and a progression of values was recorded. It was therefore possible to accurately quantify the changes in several skin parameters measured in response to the daily application of BiOvaDerm™ Cream.

Figure 11:
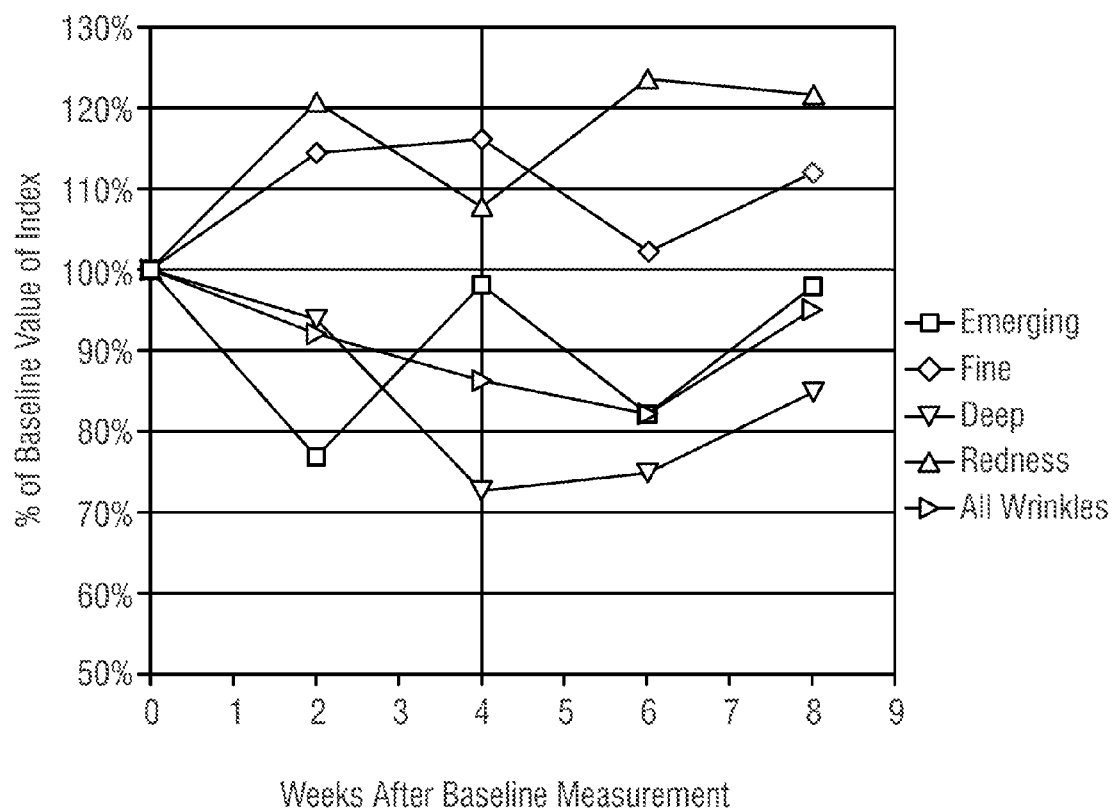

FIG. 11 is a graph depicting the average percentage change from baseline wrinkle measurements for 8 subjects who used the cream for 4 weeks and were followed an additional four weeks after stopping use.

Figure 12:
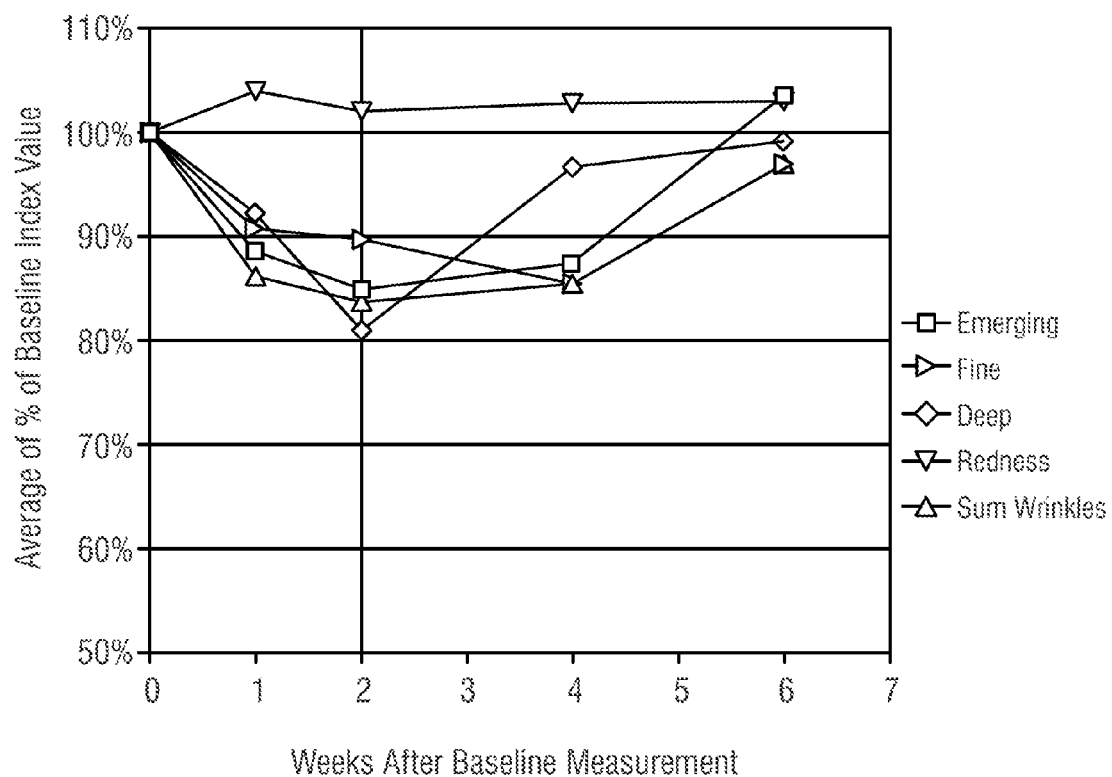

FIG. 12 is a graph showing the Effect of 2 weeks Daily BiovaDerm Use on Wrinkles and Redness.

Figure 13:
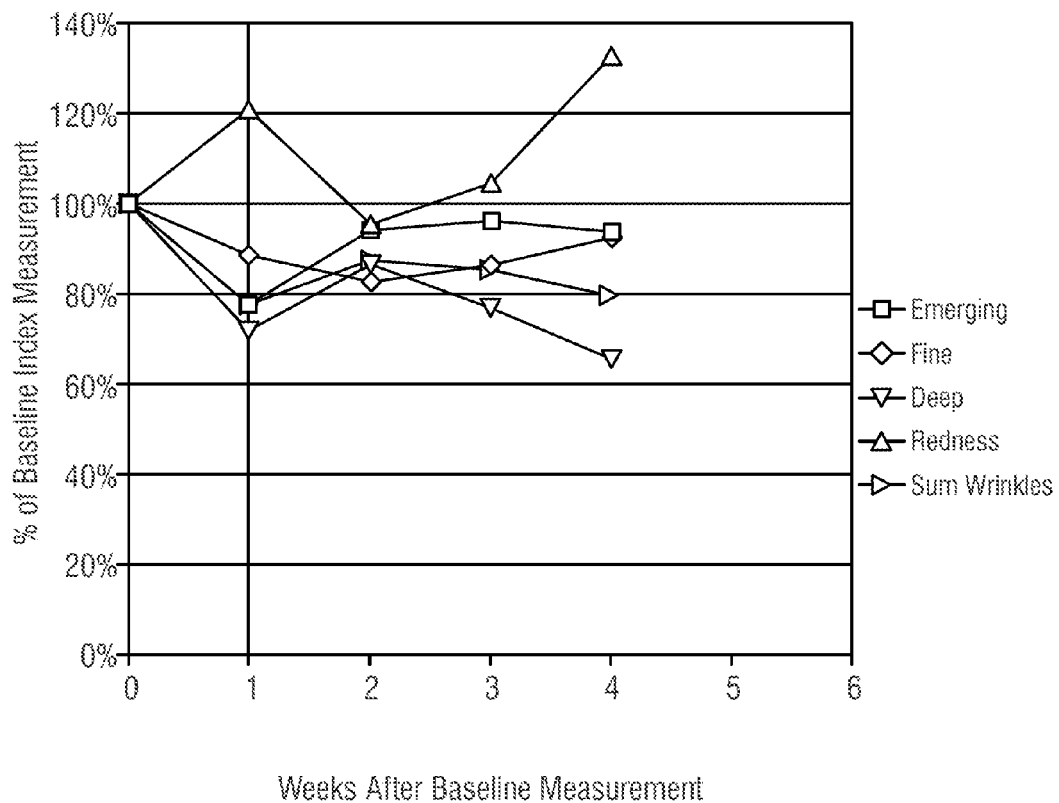

FIG. 13 is a graph showing the average percentage change from baseline wrinkle measurements for 6 subjects who used the cream for 1 weeks and were followed for another four weeks after stopping use.

Figure 14:
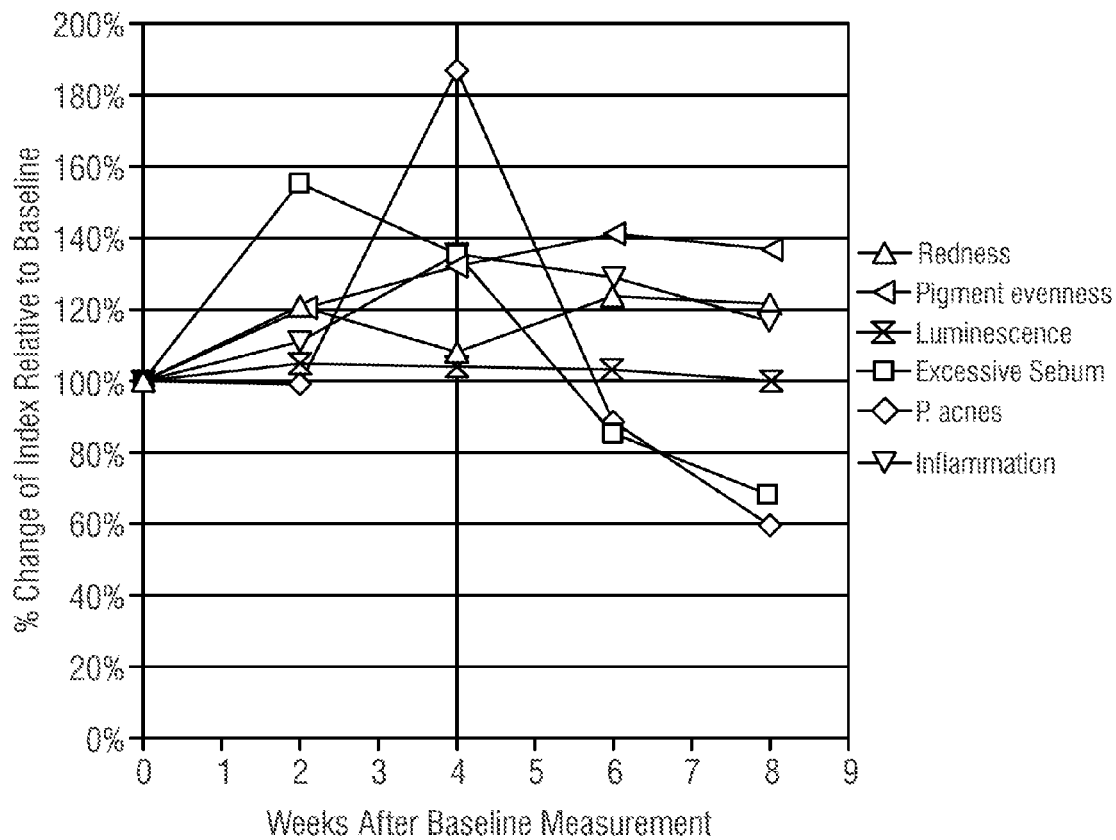

FIG. 14 is a graph showing the Pore Health and Complexion related measurements over 4 weeks. [Read from "0" baseline to the vertical line which represents the stopping point]

Figure 15:
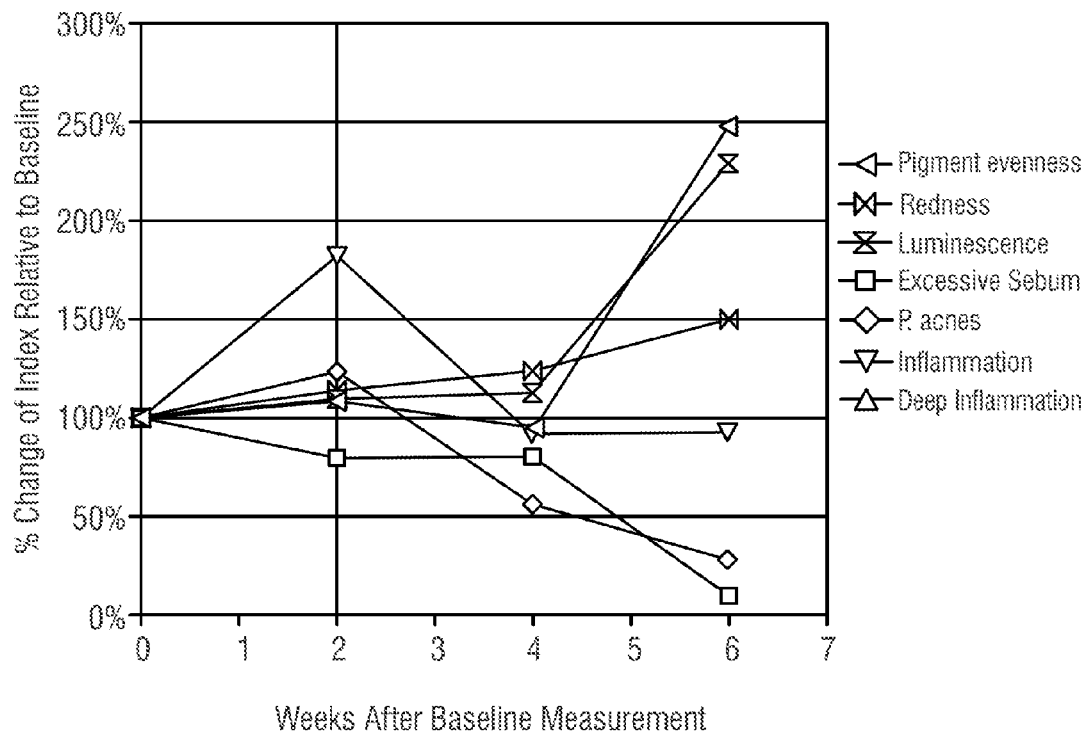

FIG. 15 is a graph showing the Pore Health and Complexion related measurements over 2 weeks. [Read from "0" baseline to the vertical line which represents the stopping point]

Figure 16:
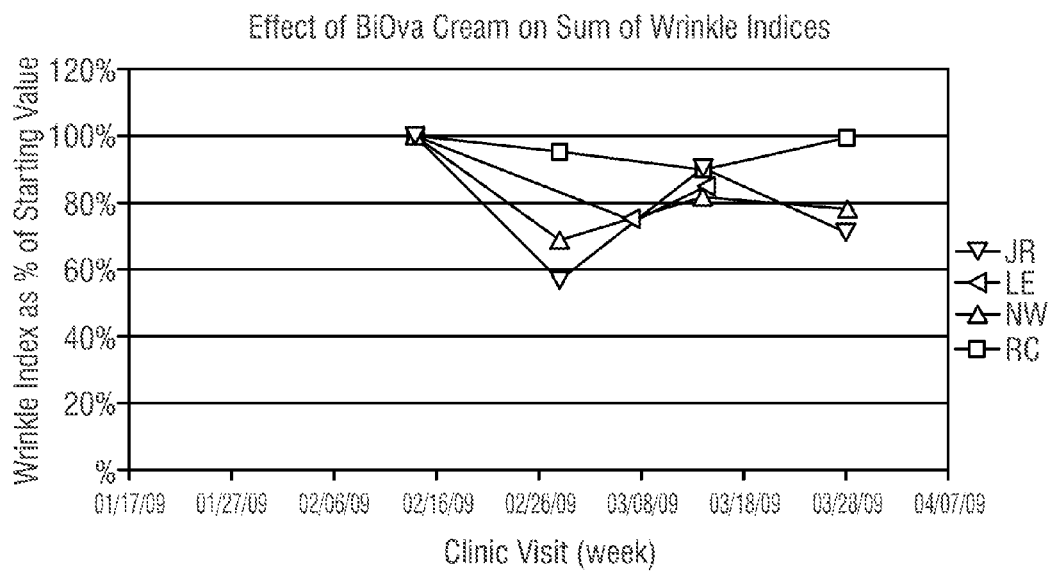

FIG. 16 is a graph showing the Sum of wrinkle measurements (Deep+Fine+Emergent) for six subjects expressed as percentage of initial pre-use value. Cream use was started day 1 and discontinued after 2 weeks Group 2. An overview of the effects of the treatment can be seen in the graph of Total Wrinkles index (Deep+Fine+Emergent) over the course of the study. The wrinkle data are plotted as percentages of the value calculated for the baseline scan taken during first visit 1 for this group (i.e. before the subjects started the treatment). Subjects were asked to discontinue use of creams at 2 weeks to test effect of non-use after daily application. The data for later visits represent wrinkles analysis after product use had been discontinued. In this group, use of the cream resulted in a reduction of wrinkles that was detected after 2 weeks of daily use and varied from 5% to 63% reduction among the subjects. KEY: JR, LE, NR, RC=Initials of study subjects.

Figure 17:
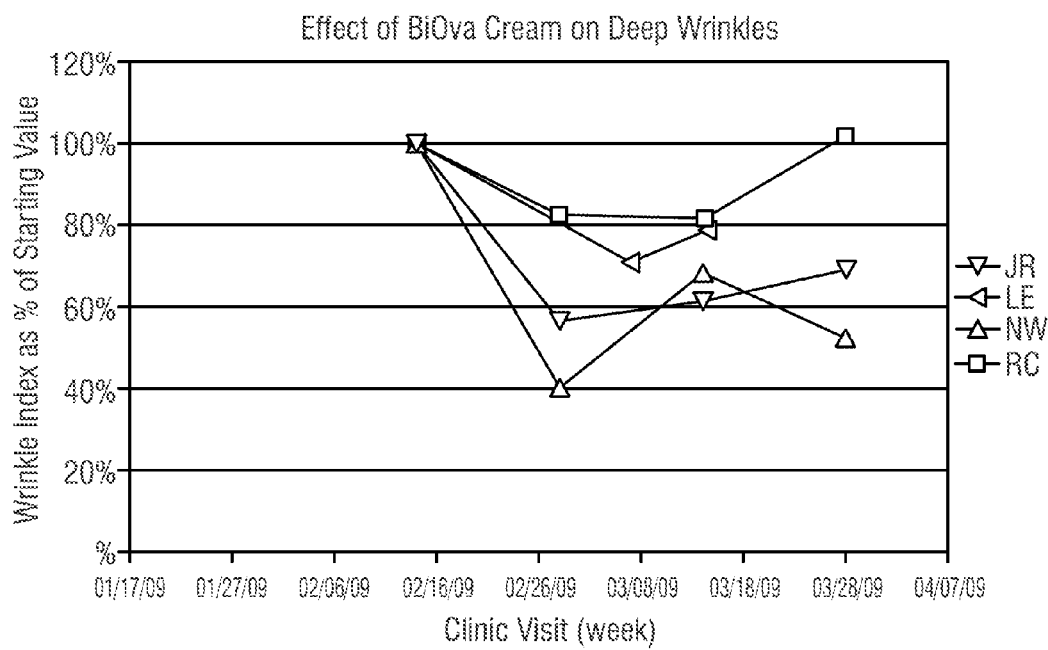

FIG. 17 is a graph showing the wrinkle measurements (Deep). Four subjects expressed as percentage of initial pre-use value. Cream use started day 1 and discontinued at 2 weeks. In these subjects, use of the cream resulted in reduction of deep wrinkles detected after 2 weeks of daily use and varied 20% to 60% reduction among the subjects. When cream was discontinued, the skin started to revert to its pre-treatment state was seen over the following 4 weeks.

Figure 18:
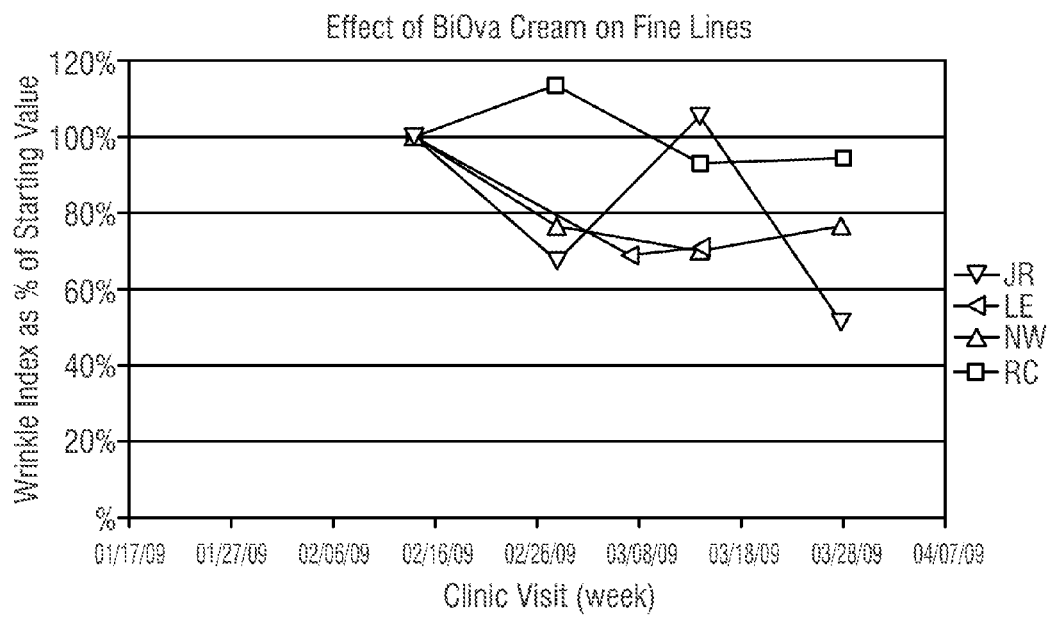

FIG. 18 is a graph showing the Wrinkle measurements (Fine) for four subjects expressed as percentage of initial pre-use value.

Figure 19:
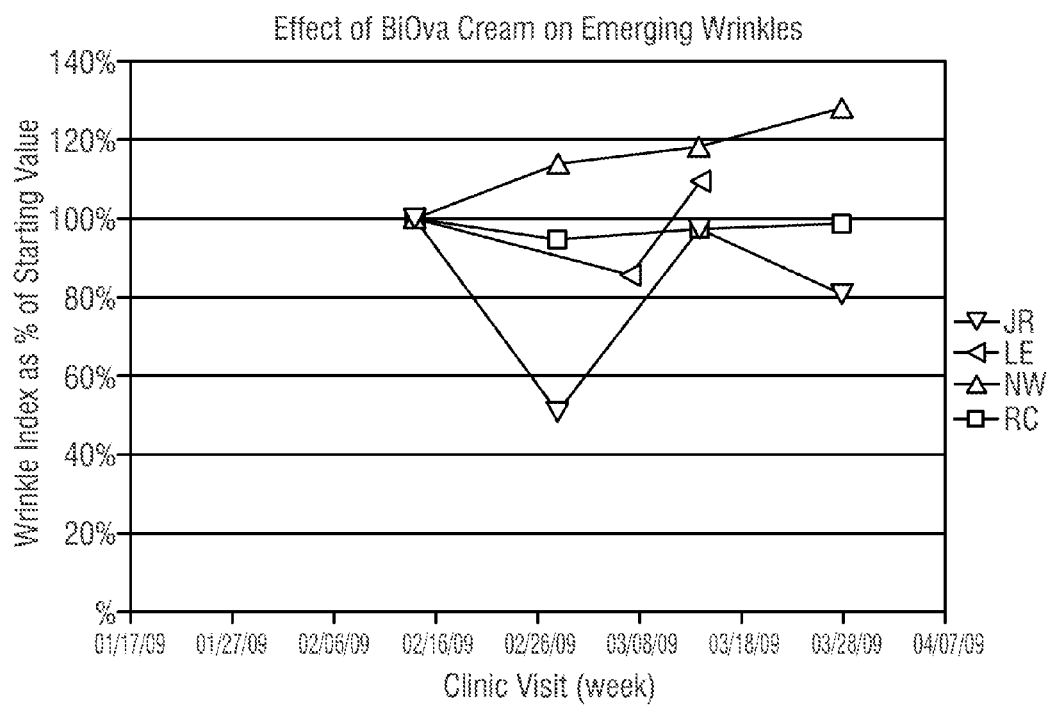

FIG. 19 is a graph showing the Wrinkle measurements (Emerging) for four subjects expressed as percentage of initial pre-use value.

FIG. 20 is a Joint Study Table which is further described in Example 14 herein.

DETAILED DESCRIPTION OF THE PREFERRED EMBODIMENT

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, processes and examples are illustrative only and not limiting. The following is presented by way of illustration and is not intended to limit the scope of the invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims.

To date, a composition containing proteins solubilized from eggshell membrane has not been obtainable on a commercial scale due to lengthy procedures, low yield of proteins and polysaccharides, or lack of bioactivity of isolated proteins. There is no known process for the preparation of a composition from eggshell membrane that overcomes current technical difficulties and produces a high yield, solubilized protein composition which is highly pure and undenaturated. The solubilized composition obtained by the process of the present invention has surprising levels of proteins, polysaccharides, and amino acids, is essentially free of odor, and can be efficiently prepared. Advantageously, since proteolytic enzymes or cross-linking agents are not used, processes of the present invention are also more economic than those of current practices.

The process of the invention is suited for solubilization of protein from various proteinaceous materials. Any suitable proteinaceous material may be employed in the practice of the present invention. As used herein, the term "proteinaceous material" is used to describe a material comprising proteins, polypeptides or peptides. Proteinaceous materials may be obtained and prepared from any number of resources. Examples include but are not limited to connective tissues, such as the combs of roosters, avian eggshell membranes, skin, fishscale, flesh, or cartilage. As used herein, the term "eggshell membrane" refers to any part of the eggshell membrane, for example, the inner eggshell membrane, the outer eggshell membrane or both. The eggshell membrane also includes the eggshell membrane in its various forms, for example, frozen, raw (wet) or dried.

Avian eggshell membranes are conventionally considered a waste product due in part to both the difficulties encountered in separating the eggshell membrane from the eggshell and further in the difficulties in processing the eggshell membrane in a manner that will result in obtaining proteins, polypeptides or peptides of interest. Various measures of the protein content of eggshell membranes are present in the prior art.

Examples of one measure of the amount of protein and individual amino acids known to be found in egg shell membranes are shown below from U.S. Pat. No. 6,899,294 to MacNeil.

| Protein And Individual Amino Acids in Eggshell Membranes | % |
| --- | --- |
| Protein | 85 |
| Lysine | 3.35 |
| Histidine | 3.48 |
| Arginine | 6.46 |
| Threonine | 4.60 |
| Glutamic Acid | 9.70 |
| Proline | 9.34 |
| Glysine | 4.94 |
| Cysteine | 8.50 |
| Valine | 6.30 |
| Methionine | 3.09 |
| Isoleucine | 3.19 |
| Leucine | 4.30 |
| Tyrosine | 1.73 |
| Phenylalanine | 1.65 |

Another measure of the typical amino acid composition of egg shell membranes is provided by U.S. patent application Ser. No. 10/797,747, Published Patent Application No. 2004/0180025 (Long et al.) and is set forth in the below table:

| Typical Amino Acid Composition of Eggshell Membrane Protein | % |
| --- | --- |
| Lysine | 2.88 |
| Tryptophan | 2.51 |
| Leucine | 3.85 |
| Aspartic Acid | 7.01 |
| Proline | 8.23 |
| Isoleucine | 2.01 |
| Threonine | 4.42 |
| Glycine | 3.99 |
| Histidine | 2.79 |
| Arginine | 5.33 |
| Tyrosine | 1.33 |
| Glutamic Acid | 8.23 |
| Cystine | 6.01 |
| Alanine | 2.00 |
| Methionine | 2.85 |
| Valine | 5.13 |
| Phenylalanine | 1.48 |
| Serine | 4.28 |

Another measure of the constituents of egg shell membranes (in percentage) is provided by Long et al and is set forth in the below table:

| Typical Constituents of Eggshell Membrane | % |
| --- | --- |
| Collagen | 35 |
| Glucosamine | 10 |
| Chondroitin | 9 |
| Hyaluronic acid | 5-10 |

Prior testing on avian egg shell membranes with a particular process is described in U.S. patent application Ser. No. 11/471,766, published patent application no. 20070017447 entitled Avian Eggshell Membrane Polypeptide Extraction Via Fermentation Process. That testing resulted in the following composition:

| Constituent | % |
| --- | --- |
| Protein | 90.08 |
| Aspartic Acid | 7.98 |
| Threonine | 5.19 |
| Serine | 5.05 |
| Glutamic Acid | 11.91 |
| Proline | 10.79 |
| Glycine | 5.43 |
| Alanine | 2.46 |
| Valine | 6.02 |
| Isoleucine | 2.91 |
| Leucine | 4.19 |
| Tyrosine | 1.57 |
| Phenylalanine | 1.60 |
| Lysine | 3.21 |
| Histidine | 3.38 |
| Arginine | 6.89 |
| Cystine | 6.72 |
| Methionine | 3.50 |
| Tryptophan | 3.64 |

Thus, there are numerous types of proteins, polypeptides, and peptides in eggshell membranes that can be extracted provided that the membranes can be solubilized. The eggshell membrane may be obtained from any number of resources, including an egg-breaking facility. The eggshell membrane may be separated from the egg white and eggshell using any suitable technique, for example mechanical or chemical methods or a combination of methods. For example, unseparated eggshells may be processed as described in U.S. patent application Ser. No. 11/333,697, U.S. Published Application No. 2006/0159816, herein incorporated by reference in its entirety. The eggshell membrane separation method includes placing the unseparated eggshells in a fluid tank containing a fluid mixture, such as a mixture of distilled water and acetic acid, and applying cavitation to thereby assist in separating the eggshell membranes from the eggshells. The eggshell membranes may then be recovered using any suitable technique, preferably the separation process does not damage or denature the proteins. The isolated eggshell membrane may be processed as described herein. For example, the eggshell membranes may be subjected to a solubilization process for solubilizing at least one type of polypeptide or polysaccharide from the eggshell membranes. Components of interest that may be solubilized include but are not limited to collagen, elastin, desmosine, lysozyme, glucosamine, chondroitin, ovotransferrin, B—N-acetylglucosaminidase, hyaluronic acid, amino acids or other components of interest. The collagen may be Type I collagen, Type V collagen, Type X collagen or combinations thereof. The components may be solubilized from the eggshell membrane and purified for numerous uses.

As shown in FIG. 1, in one embodiment, the process of the present invention includes subjecting a proteinaceous material such as eggshell membrane to a sufficient amount of a basic solution so that hydrolysis of the eggshell membrane occurs. The basic solution is added to the eggshell membrane to produce a supernatant having a basic pH. As used herein, the term basic refers to a pH greater than 7. The pH of the supernatant may be adjusted to a pH of from about 9.0 to a pH of from about 11.5, preferably from a pH range of from about 10.5 to about 11.5. Any suitable basic solution may be used including but not limited to sodium hydroxide, potassium hydroxide, and calcium hydroxide. The sufficient amount of basic solution to add to the proteinaceous material may be determined in any number of ways as appreciated by those skilled in the art. For example, the sufficient amount of the basic solution necessary to achieve a pH from about 9.0 to about 11.5 may be determined based on the total weight of the proteinaceous material, preferably based on the solid (dry) weight of the proteinaceous material, and the molarity of the basic solution. It is preferred that the temperature and pH be closely monitored, so that functional proteins, polypeptides and peptides are obtained rather than mostly amino acids. As used herein, a "polypeptide", "peptide" or "protein" are used interchangeably.

In one aspect, the process includes exposing the supernatant to the basic solution for a sufficient length of time and temperature for hydrolysis to occur. One skilled in the art will appreciate that the time needed for the hydrolysis reaction of the proteinaceous material to proceed will vary in part based on the temperature selected. Accordingly, hydrolysis of the proteinaceous material may be carried out at any suitable temperature for any suitable length of time, for example, the temperature may be from a range of about 30° C. to about 65° C., preferably from a temperature of about 45° C. to about 60° C., and more preferably from a temperature of at least about 50° C. The hydrolysis time can be as long as necessary to achieve the desired result. The length of time the proteinaceous material is subjected to hydrolysis may vary from as little as hours, such as 1 to 24 hours, to days depending on the temperature and other conditions used. For example, use of a higher temperature, for example of 50° C. compared to 30° C., and stirring the mixture of proteinaceous material/basic solution would reduce the length of time needed for hydrolysis reaction to occur. One skilled in the art can monitor the progress of the hydrolysis reaction using standard techniques such as trichloroacetic acid (TCA) protein precipitation and/or visualization methods. For example, one could take a sample of the supernatant, precipitate proteins out using TCA, and analyze the supernatant after TCA precipitation for levels of nitrogen (indicative of free amino acids). Alternately, hydrolysis may be monitored by using simple visualization methods over selected time intervals. Typically, measurements are performed about one to three hours after subjecting the proteinaceous material to the basic solution to assess hydrolysis of the proteinaceous material into soluble proteins. A sample may be taken from the proteinaceous material/basic solution mixture and the sample analyzed for the presence of insoluble proteins of the eggshell membrane. Samples are spun down using centrifugation and the contents visually analyzed for the presence of a yellow material of non-hydrolyzed eggshell membranes, i.e. insoluble eggshell membrane proteins. It is noted that spun down samples may also contain eggshell particulates which are white in color. If the yellow material of insoluble eggshell membrane proteins is observed then the hydrolysis reaction is allowed to proceed and samples from the mixture are taken at 15 to 20 minute intervals thereafter and evaluated. Typically, the reaction is allowed to proceed until the yellow insoluble proteins are no longer present in the spun down samples. Thus, one skilled in the art can determine whether the proteinaceous material has been substantially hydrolyzed, whether more time is needed or whether the reaction has proceeded too long as indicated by the hydrolysis of the proteins into amino acids.

In one aspect, the process of the invention includes cooling the supernatant. For example, the temperature of the supernatant comprising the hydrolyzed proteinaceous material may be adjusted to a temperature of from about 2° C. to about 18° C., more preferably to a temperature of about 2° C. to about 7° C.

In another aspect, the process includes the removal of particulates, such as eggshells or fine calcium from eggshells, from the supernatant containing the hydrolyzed proteinaceous material by any suitable separation technique. This may be accomplished in any number of ways, including, but not limited to centrifugation, ultra-centrifugation, filtration or microfiltration, or combinations of separation techniques. For example, centrifugation may be used to separate particulates from the supernatant containing the hydrolyzed proteinaceous material and the supernatant removed by decanting, pumping, and the like. Any number of filtration techniques may be used for the process of the present invention, including but not limited to gravity filtration, pressure filtration, vacuum filtration, batch filtration, membrane filtration, filter press, continuous filtration, or any suitable combination. Filtration may include the use of any suitable filter that is capable of removing particulates from the supernatant. A suitable filter may include but is not limited to a drum filter, a disk filter, filter press or a sock filter. Preferably, a filter sock with a 100 micron to 865 micron sock size is used. The filter may be made from a variety of materials such as, but not limited to, sintered-metal, cloth, polymeric fiber, natural fiber, paper such as a coffee filter, metal mesh, pulp, ceramic, or a combination of the foregoing materials, and the like. The pore size of the filter may be of any size so long as it filters out the desired particulates. The range of pore size may be from of 0.01 micrometers to 100-200 micrometers, or greater.

The resulting solubilized components in the supernatant can be further purified, isolated, and/or concentrated. For example, in one aspect, the process of the present invention includes removing salt (ash) or minerals from the supernatant. The relative amount of salts/minerals in the supernatant can be determined using any suitable technique including measuring the conductivity of the supernatant, using, for example, a meter to measure conductivity in milliSiemens (mS), ppm, ampre/volts, etc. The level of salt in the supernatant can be adjusted so that the final solubilized composition has the desired or acceptable level or percentage of ash, depending on the intended use for the resulting solubilized composition and the industry standards.

For example, with respect to the solubilization of avian eggshell membranes, a conductivity of a supernatant that is at or above 5 milliSiemens/cm may be considered to be a high level of salt/mineral. If the salt/mineral content in the supernatant is not reduced, it will become ash in the resulting solubilized composition. Ash is undesirable because it is potentially perceived as a "filler" in the consumed product. Additionally, many health conscious consumers may desire to limit their consumption of salt. The reduction in the amount of ash in the supernatant increases the percentage of protein content in the recovered solubilized composition.

If the supernatant has a conductivity that would result in the solubilized protein composition having an ash content that is unacceptable, salts/minerals may be removed from the supernatant until an acceptable level of salt is present in the supernatant. In some cases, a supernatant having less than 5 milliSiemens/cm (mS/cm) is acceptable, preferably 4 or less mS/cm, more preferably from about 2 to about 4 mS/cm.

The salt/minerals may be removed from the supernatant using any suitable process, for example, filtration, dialysis or ion exchange. The process may include separating the hydrolyzed proteins in the supernatant from salt and if desired, specific molecules, using a membrane. The separation may be performed using any suitable technique, such as the use of a membrane. This also allows for the concentration of a composition that has high levels of solubilized proteins. The composition may also contain polysaccharides. Any process that allows for concentration may be used, although, preferably the concentration process maintains the biological activities of the composition or of the individual components in the composition. Typically, the supernatants are passed through a membrane having the desired nominal molecular weight cut-off value, leaving solubilized proteins and other solubilized components having a molecular weight larger than the cut-off value behind. In one embodiment, a membrane with a nominal molecular weight cut-off value of about 1000-3000 Daltons is used, resulting in a composition that has high amounts of solubilized proteins, but allowing amino acids and other small molecules to pass through. For example, a membrane having a nominal molecular weight cut-off value of about 3 kilodaltons may be used to isolate solubilized proteins larger than 3 kilodaltons (BIO2, SKU309, Ovacore, Ovaflex, Ova-Derm, 3 kDa retentate) and solubilized proteins that are less than 3 kilodaltons (BIO1, SKU313, SKU314, NF retentate) such as small molecular weight peptides in the range of 3,000 daltons to 400 daltons, which is the typical NF membrane molecular weight cutoff. If desired, the amino acids may be recovered from the supernatant or retentate, such as a retentate produced by using a nanofilter, for use in any number of applications, such as consumable products and compositions such as cosmetic, dermatological and pharmaceutical compositions.

Depending on the size of membrane used, the composition obtained from the retentate and/or permeate may also contain in addition to the solubilized, hydrolyzed proteins and amino acids: acid glycosaminoglycans including but not limited to dermatan sulfate, chondroitin-4-sulfate (Picard, et. al., isolated and characterized sulfated glycoproteins from eggshell membrane), glycoproteins including but not limited to hexosamines, hexoses, fucose; glucosamine, hyaluronic acid, ovotransferrin, desmosine, isodesmosine, lysyl oxidase, and/or lysozyme and the like.

Solubilized components may be isolated in any manner that is convenient. As appreciated by those ordinarily skilled in the art, the selection of membrane size can be used to obtain a composition enriched for a particular size of protein or population of proteins. For example, use of a membrane having a nominal molecular weight cut-off value of about 100 kDa may be used to isolate elastin and other solubilized proteins larger than 100 kDa and proteins that are less than 100 kDa such as collagen and desmosine. Desmosine, an anti-oxidant of four amino acid residues of lysine, may be released when the elastin is solubilized, and if desired, may be further concentrated using a membrane having a nominal molecular weight cut-off value of less than 500 molecular wt. Any suitable membrane size may be used such as 3, 6, 10, 50, 100, and greater.

Advantageously, filtering and/or performing dialysis of the supernatant may remove sulfur compounds from the supernatant, thereby reducing the sulfur odor of the supernatant. In another aspect, the process of the invention may include removing odor causing components from the supernatant, for example, by using a filter with an odor-absorbing compound such as a charcoal filter or an activated carbon filter. Additionally, an odor-reacting compound that is an oxidizing agent, such as hydrogen peroxide, may be added to the supernatant to reduce sulfur odors. The process may also include reducing the number of microorganisms in the supernatant by subjecting the supernatant to filtration, for example, a 0.8 micrometer filter.

In another aspect, the process includes adjusting the pH of the supernatant or permeate comprising the hydrolyzed proteins so that the supernatant or permeate has a pH from about 6.0 to about 8.0, preferably to a pH of about 7.0. The pH may be adjusted using any suitable acidic solution that has a pH of less than 7, including but not limited to a solution of acetic, oxalic, phosphoric, chloroacetic, citric, formic, benzoic, oxalic, succinic, acetic, propionic hydrochloric, nitric, sulfuric, hydrotropic, hydrologic, perchloric, chloric, phosphoric, or sulfurous acid or combinations thereof. In one embodiment, the pH and the temperature of the supernatant or permeate are lowered simultaneously or consecutively, although it is preferred that the supernatant be cooled prior to addition of the acidic solution.

In a preferred embodiment, the removal of salts, for example, by dialysis, pH adjustment of the supernatant or permeate from a basic pH to a pH of about 7.0, and removal of sulfur odor using hydrogen peroxide are performed simultaneously. As appreciated by one skilled in the art, these steps may be performed consecutively, in a different order, or omitted and still yield a composition of solubilized proteins.

The solubilized composition resulting from the process of the present invention may be prepared in any number of forms or formulations. In one embodiment, the composition of solubilized protein is prepared as a protein powder using any suitable technique, including but not limited to lyophilization, vacuum drying, freeze drying, spray drying, drum drying, paddle-drying, super critical fluid processing, air drying, or other forms of evaporative drying. The drying step may be carried out any suitable temperature, for example, with respect to freeze drying, a preferred temperature range is from about 23° C. to about 40° C., with 27° C. being the more preferred temperature.

The present invention is advantageous in that multiple components are efficiently and economically solubilized from the eggshell membrane at the same time. Additionally, if desired, one or more specific components may be isolated from the solubilized eggshell membrane, such as elastin, collagen or desmosine. Thus, the present invention allows for the production of a composition of a specific component or combination of selected components in amounts suitable for use in a particular application. Thus, the composition may be customized for use in a particular product, for example, a cosmetic product or a dietary supplement. Advantageously, the compositions of the present invention are essentially odor-free.

Once the proteinaceous material or source is solubilized, one skilled in the art would be able to readily use standard biochemistry techniques such as membrane filtration or chromatography to isolate a protein of interest. Accordingly, the process of the invention may also include isolating from the supernatant or dried solubilized composition various proteins and polysaccharides of interest depending on the source of the starting proteinaceous material. For example, proteins of interest that may be isolated from solubilized avian eggshell membrane include but are not limited to elastin, desmosine, lysozyme, ovotransferrin, B—N-acetylglucosaminidase, collagen such as Type I collagen, Type V collagen, Type X collagen, or combinations thereof or other products of interest. Polysaccharides of interest that may be isolated include but are not limited to hyaluronic acid, glucosamine, and chondroitin.

In one embodiment, a soluble protein composition may be obtained from methods of the present invention. In one aspect, the protein composition may include elastin, desmosine, ovotransferrin, B—N-acetylglucosaminidase, collagen such as Type I collagen, Type V collagen, and/or Type X collagen, amino acids or combinations thereof. The amino acids present in the composition may include tryptophan, cystine, methionine, aspartic acid, threonine, serine, glutamic acid, proline, glutamic acid, proline, glycine, alanine, valine, isoleucine, tyrosine, phenylalanine, lysine, histidine, arginine, hydroxyproline and the like. The composition may also include hyaluronic acid, glucosamine, and chondroitin. In one aspect, the composition is more than 50%, 55%, 60%, 65%, 70%, 75%, 80%, 85%, 90% or 95% protein per weight of composition. In one aspect, the composition includes at least 10%, 15%, 20%, 25%, 30%, 35%, 40%, 45%, 50%, 55%, 60%, 65%, 70%, 75% or 80% collagen and/or least 1% elastin. Of the collagen present, the collagen may be 5%, 10%, 15%, 20%, 25%, 30%, 35%, 40%, 45%, 50%, 55%, 60%, 65%, 70%, 75%, 80%, 85%, 90% or 95% of Type I collagen. The composition may include 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or 95% of Type V collagen. The collagen of the composition may be 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90% or 95% of Type X collagen. The amount of elastin in the composition may vary depending on the size of membrane used to isolate the solubilized proteins. As shown in FIGS. 2 and 3, the composition may contain at least 10%, 15%, 20%, 25%, 30%, 35% or even 40% elastin. In one embodiment, the invention includes an isolated, soluble protein composition that is at least 10%, 15%, 20%, 25%, 30%, 35%, 40%, 45%, 50%, 55%, 60%, 65%, 70%, 75%, 80%, 85%, 90%, 95%, 96%, 97%, 98% or 99% soluble. The composition or protein is "soluble" or "solubilized" if at least at least 10% (by weight) of the protein or composition dissolves or does not aggregate in distilled water. Preferably, solubility of the protein or composition is assessed in distilled water, for example, at a concentration of 1 gram of the protein or composition per 9 grams of distilled water. The composition may be 10%, 15%, 20%, 25%, 30%, 35%, 40%, 45%, 50%, 55%, 60%, 65%, 70%, 75%, 80%, 85%, 90% or 95% (by weight) water soluble. As discussed and shown elsewhere herein, the protein composition may also contain other eggshell membrane components including but not limited to acid glycosaminoglycans including but not limited to dermatan sulfate, chondroitin-4-sulfate, glycoproteins including but not limited to hexosamines, hexoses, fucose; glucosamine, hyaluronic acid, ovotransferrin, desmosine, isodesmosine, lysyl oxidase, and/or lysozyme and the like.

The failure to develop a commercially feasible process of solubilizing various components from eggshell membrane is due in part to failure by others to demonstrate high yields of a product in a highly purified, soluble form and that has retained bioactivity. As used interchangeably herein, a "bioactivity", "biological activity" or "native activity", refers to a function exerted by an intact, non-denatured protein, polypeptide or peptide as determined in vivo, or in vitro, according to standard techniques. The protein, polypeptide or peptide may be hydrolyzed. As described herein, the compositions of the present invention may be obtained from eggshell membranes without the use of proteolytic enzymes or cross-linking agents. Accordingly, the hydrolyzed, solubilized protein compositions are believed to be substantially pure, undenatured and retain biological activity.

A method of the present invention includes treating an animal or human in need of a component solubilized from eggshell membrane, e.g. protein, peptides, or amino acids, by administering a composition of the present invention. As described elsewhere herein, the composition, fraction thereof, or component thereof may exhibit one or more of the following activities: (1) antioxidant activity, (2) anti-inflammatory activity, (3) decreasing ROS formation, (4) maintaining mitochondrial function under conditions of ROS, (5) decreasing apoptosis under condition of oxidative stress, (6) decreasing necrosis under condition of oxidative stress, (7) maintaining cell viability under condition of oxidative stress, (8) increasing PMN migration, (9) decreasing PMNB cell migration toward inflammatory mediator leukotriene B4, (10) anti-wrinkling activity, (11) wound healing, (12) bone healing, (13) muscle regeneration, and (14) recovery after trauma. Accordingly, the compositions, fractions or components, e.g. proteins or polysaccharides isolated thereof, may be used in any number of applications, including but not limited to products or services in the cosmetic industry, see, for example, U.S. Pat. No. 7,169,379 to Kouzuki; products in the health industry, for example, products for use in joint health; and products in the medical industry, such as for wound healing, see U.S. Pat. No. 7,041,868 to Greene. Such applications are known in the art as well as the appropriate techniques for inclusion in such applications.

Accordingly, the invention also provides a method of treating a variety of diseases, disorders, and conditions that benefit from an effective amount of a composition of one or more components obtained from solubilized eggshell membrane, e.g. a hydrolyzed, water-soluble protein composition from the eggshell membrane, a composition of one of more fractions thereof such as a retentate fraction or permeate fraction of components having the desired molecular mass (kDa), or a composition comprising individual components, e.g. proteins or polysaccharides, thereof. As used here, the term "effective amount," means that amount of the composition that provides a therapeutic benefit in the treatment, prevention, or management of one or more conditions, symptoms, diseases, and/or disorders. As used herein, unless otherwise defined in conjunction with specific diseases or disorders, the term "treating" refers to: (i) preventing a disease, disorder or condition from occurring in an animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition. Beneficial or desired clinical results can include, but are not limited to, alleviation or amelioration of one or more symptoms or conditions of the disease, disorder or condition, diminishment of extent of disease, stabilized (i.e. not worsening) state of disease, disorder or condition, preventing spread of disease, delay or slowing of disease progression. "Treating" can also mean prolonging survival as compared to expected survival if not receiving treatment.

In general, the present invention provides compositions that have numerous beneficial effects and a broad range of uses. For example, provided herein are methodologies for prophylactically treating, as well as for therapeutically treating a variety of diseases, disorders, or conditions. In some embodiments, the diseases, disorders, or conditions are associated with oxidative stress. As used herein, "oxidative-stress-associated disease, disorder, or condition" refers to a pathological condition of an individual that results at least in part from the production of or exposure to reactive oxygen species (ROS), including but not limited to apoptosis-induced oxidative stress, necrosis-induced oxidative stress, inflammation induced by oxidative stress, mitochondrial function modulated by oxidative stress. The term "oxidative-stress associated disease" encompasses pathological states that are recognized in the art as being conditions wherein damage from free radicals or reactive oxygen species is believed to contribute to the pathology of the disease state, or wherein administration of a ROS inhibitor (e.g., antioxidant such as beta carotene), is shown to produce a detectable benefit by decreasing symptoms, increasing survival, or providing other detectable clinical benefits in treating or preventing the pathological state.

Oxidative-stress-associated diseases, disorders, or conditions include but are not limited to stroke, neurodegenerative diseases (such as Alzheimer's Disease, Parkinson's Disease, Huntington's Disease, spinocerebellar ataxias), trauma (such as spinal cord injuries, skeletal or cardiac muscle injuries, kidney injuries, or liver injuries), muscular disorders (such as mitochondrial myopathy, lactic acidosis), diabetes, ischemia-reperfusion tissue injury, hypoxic-induced tissue damage, migraines, congenital mitochondrial diseases (such as MELAS, LHON, Kearns-Sayres Syndrome, MERRF, NARP, Leigh's Syndrome), neuromuscular degenerative disorders (such as Friedreich's Ataxia, Duchenne muscular dystrophy, Multiple Sclerosis), epilepsy, neuropathy, neurological and neuropsychological developmental delays, amyotrophic lateral sclerosis (Lou Gehrig's Disease), renal tubular acidosis, and aging related diseases or disorders (such as cognitive and motor disorders, progeria, cancer). For example, the compositions may be useful in slowing down manifestations and symptoms of degenerative aging, the pre-onset of Parkinson's disease, Alzheimer's disease, diabetes, and cancer. When the condition being treated in an individual is an inflammatory condition, the compositions may be useful in reducing any of the symptoms associated with inflammation, including, but not limited to, inflammation, redness, pain, swelling, lameness, and loss of mobility.

The invention also provides a method for treating the effects of oxidative stress due to the production of harmful oxygen-derived species which comprises administering an effective amount of a composition of the present invention to a mammal or human susceptible to oxidative stress. Such stress includes that due to oxidizing agents, increased oxygen exposure, oxygen-induced degeneration or disease, reperfusion injury, ionizing radiation, carcinogenic, chemotherapeutic, or mutagenic agents, aging, or arthritis and the like.

The present invention also provides methods for therapy and prophylaxis of oxidative-stress associated diseases, disorders or conditions comprising administering to a patient a therapeutically-effective amount of a composition of the present invention. Exemplary disease or conditions states associated with oxidative-stress include without limitation ischemic reperfusion injury, inflammatory diseases, systemic lupus erythematosus, myocardial infarction, stroke, traumatic hemorrhage, brain and spinal cord trauma, Crohn's disease, autoimmune diseases (e.g., rheumatoid arthritis, diabetes), cataract formation, uveitis, emphysema, gastric ulcers, oxygen toxicity, neoplasia, undesired cell apoptosis, radiation sickness, and other pathological states disclosed herein, such as toxemia and acute lung injury), cerebral ischemia, retinal ischemia, myocardial infarction, chronic heart failure, post-surgical cognitive dysfunctions, peripheral neuropathy, spinal cord injury, head injury, and surgical trauma. Such diseases, disorders or conditions can include "apoptosis-related ROS," which refers to reactive oxygen species (e.g., $O_2^-$, HOOH) which damage critical cellular components (e.g., lipid peroxidation) in cells stimulated to undergo apoptosis, such apoptosis-related ROS may be formed in a cell in response to an apoptotic stimulus and/or produced by non-respiratory electron transport chains (i.e., other than ROS produced by oxidative phosphorylation). Methods of the invention include treating cells that are apoptotic or otherwise undergoing programmed cell death, or at risk to undergo such programmed cell death by administering an effective amount of a composition of the present invention such as solubilized eggshell membrane, fractions thereof or components, e.g. proteins or polysaccharides isolated thereof. Exemplary cells include but are not limited to ventricular cells and neuronal cells. For example, an individual suffering from or susceptible to heart failure can be treated in accordance with the invention. Methods for treating a disease, disorder, or condition resulting in part from apoptosis-induced by oxidative stress such as from ROS are provided. Therefore, one aspect of the present invention relates to a method of decreasing oxidative stress-induced injury and/or death of a cell in an individual, for example, as compared to a control not administered a composition of the invention.

Additionally, a subject suffering from a condition involving programmed cell death of neuronal cells can be treated in accordance with the invention, particularly to treat a subject suffering from stroke, spinal cord injury or a neurodegenerative disease such as Alzheimer's disease, Parkinson's disease, Huntington's disease, Amyotrophic Lateral Sclerosis, Down's Syndrome, Korsakoffs disease, cerebral palsy, age-dependent dementia, diabetes, including treatment of pancreatic beta cells, apoptosis of which can be involved with a subject suffering from diabetes. Treatment methods of the invention include administration to a mammal in need of such treatment a therapeutically effective amount of one or more compositions of the invention. The invention also includes treatment of diabetes, including treatment of pancreatic beta cells. The invention also provides a method for inhibiting cell necrosis which can be used to treat any condition wherein it is desirable to prevent cell death through necrosis, especially under conditions of oxidative stress.

Accordingly, the present invention also provides a method of treating or preventing a condition associated with oxidative stress-induced injury and/or death. The methods described herein may include administering a composition of the present invention or a pharmaceutical, cosmetic, medical or dermatological product comprising the composition. In some cases, the individual has a condition associated with oxidative stress-induced cellular injury and/or death or may be at risk for developing an oxidative stress-induced cellular injury and/or death. Conditions to be treated or prevented in accordance with this aspect of the present invention are any condition, disease, disorder, or dysfunction that implicates ROS in the etiology of the condition, disease, disorder, or dysfunction. Exemplary conditions, diseases, disorders, and dysfunctions include, without limitation, an inflammatory condition, an allergic condition or an auto-immune condition, inflammatory pulmonary disease or reactions (e.g., asthma, allergic rhinitis, chronic obstructive pulmonary disease, and adult respiratory distress syndrome), inflammatory musculoskeletal disease or reaction (e.g., soft tissue rheumatism, exercise-induced injury, rheumatoid arthritis, psoriatic arthritis, osteoporosis and osteoarthritis), inflammatory gastrointestinal disease or urogenital reaction (e.g., enterocolitis, gastritis, Crohn's disease, interstitial cystitis, vaginitis, and ulcerative colitis), autoimmune disease or reactions (e.g., inflammatory bowel disease, and psoriasis), transplantation rejection reactions, ischemia, cataract, corneal pathology, glaucoma, retinal degeneration, vitreal degeneration, atherogenesis, hypertension, diabetes mellitus, hypercholesterolemia, cigarette smoking, degenerative diseases of aging and cancer, immune deficiency, hyperimmunity, autoimmunity, neurodegeneration, aging, glomerular nephritis, respiratory distress syndrome, asthma, coronary thrombosis, burns, sunlight exposure, psoriasis, dermatosis, trauma, Parkinson's disease, neurotoxins, dementia, rheumatoid arthritis, diabetes, pancreatitis, endotoxemia, intestinal eschemia, cataracts, retinopathy, retinal degeneration, arteriosclerosis, Fanconi's anemia, malaria, inflammation, ischaemia-reperfusion, drug toxicity, iron overload, nutritional deficiency, alcohol, radiation, cancer, aging, HCV infection and AIDS. Machoado-Joseph disease, multiple sclerosis, muscular dystrophy, senility, muscular atrophy, stroke, hepatopathies, systemic lupus erythematosus, mixed connective tissue disease, multiple sclerosis or diabetes, stroke, neurodegenerative diseases (such as Alzheimer's Disease, Parkinson's Disease, Huntington's Disease, spinocerebellar ataxias), trauma (such as spinal cord injuries, skeletal or cardiac muscle injuries, kidney injuries, or liver injuries), neuromuscular degenerative disorders (such as Friedreich's Ataxia, Duchenne muscular dystrophy, Multiple Sclerosis), epilepsy, neuropathy, neurological and neuropsychological developmental delays, amyotrophic lateral sclerosis (Lou Gehrig's Disease), muscular disorders (such as mitochondrial myopathy, lactic acidosis), diabetes, ischemia-reperfusion tissue injury, hypoxic-induced tissue damage, migraines, congenital mitochondrial diseases (such as MELAS, LHON, Kearns-Sayres Syndrome, MERRF, NARP, Leigh's Syndrome), renal tubular acidosis, and aging related diseases or disorders (such as cognitive and motor disorders, progeria, cancer). While the above list is merely illustrative, a more complete list of mitochondrial diseases or disorders that can be treated in accordance with the present invention is provided in United States Patent Application 2001/0005719 by Von Borstel, which is hereby incorporated by reference in its entirety.

In some cases oxidative stress is due to the production of harmful oxygen-derived species. Any disease, disorder, condition or physiological and/or pathological situation leading to overproduction of ROS may be treated using the compositions and methods of the present invention. Numerous studies suggest that the aging process and various disease-related degenerative processes are caused, at least partly, by the free-radical-mediated oxidative stress and/or the oxidative shift in the thiol/disulfide redox state (Beckaman and Ames, Physiol. Rev. 78 (1998) 547-581; Droge, Physiol. Rev. 2002, in press). Oxidative stress has also been implicated in the development of neurodegenerative diseases, especially Alzheimer's disease (Montine et al., J. Neuropathol. Exp. Neurol. 56 (1997) 866-871; Sayre et al., J. Neurochem 68 (1997) 2092-2097; Lovell et al., Neurobiol. Aging 18 (1997) 457-461; Multhaup et al., Biochem. Pharmacol. 54 (1997) 533-539; Pratico et al., FASEB J. 12 (1998) 1777-1783; Behl et al., Cell 77 (1994) 817-827; Kaltschmidt et al., Proc. Natl. Acad. Sci. USA 94 (1997) 2642-2647), and amyotrophic lateral skelarosis (Rosen et al., Nature 362 (1993) 59-62; Tu et al., Lab. Invest. 76 (1997) 441-456). Moreover, studies on primates revealed a massive age-related increase in oxidative stress in the skeletal muscle tissue (Zainal et al.; FASEB J. 14 (2000) 1825-1836), arid clear manifestations of oxidative stress were also seen in gene expression profiles of skeletal muscle tissue and brain tissue from old mice as detected by oligonucleotide arrays (Lee et al., Science 285 (1999) 1390-1393; Lee et al., Nature Genet. 25 (2000) 294-297. Exemplary diseases and disorders that may be treated with a composition of the invention include but are not limited to neurodegenerative diseases (such as Alzheimer's Disease, Parkinson's Disease, Huntington's Disease, spinocerebellar ataxias) and/or dementia.

In some cases, the oxidative stress may in part result from normal mitochondrial function. For example, in mammals, the cellular levels of reactive oxygen species ("ROS") produced by normal mitochondrial function increase throughout the aging process (Passos et al, Mitochondria and ageing: winning and losing in the numbers game, BioEssays 29:908-917, 2007). In other cases, oxidative stress may result from abnormal mitochondrial function causing disorders such as Mitochondrial Encephalomyopathy Lactic Acidemia and Stroke-like episodes MELAS, Myoclonic Epilepsy with "Ragged Red" (muscle) Fibers) (MERRF), Neurogenic muscle weakness, Ataxia, and Retinitis Pigmentosa (NARP), Leber's Hereditary Optic Neuropathy (LHON), Leigh's Syndrome (Subacute Necrotizing Encephalomyopathy), Progressive External Opthalmoplegia (PEO), and Kearns-Sayres Syndrome, pigmentary retinopathy, ataxia, and heart-block. Mitochondrial dysfunction is diabetes, type II diabetes mellitus, cardiomyopathy, Parkinson's disease, Huntington's disease, and premature aging and the like. Accordingly, the invention also provides a method for treating an individual having oxidative stress associated with normal or abnormal mitochondrial function by administering an effective amount of a composition of the present invention. In a preferred embodiment, mitochondria-containing cells are contacted in vitro or in vivo with a composition of the present invention. Exemplary cells include, without limitation, neuronal cells, muscle cells (preferably skeletal or cardiac muscle cells), liver cells, and/or kidney cells.

Oxidative stress and mitochondrial function can be determined in any number of ways, for example, measuring mitochondrial DNA damage including mitochondrial protein production, changes in mitochondrial oxidative phosphorylation or changes in mitochondrial ATP production would accomplish the same goal. See also, for example, U.S. Pat. No. 7,288,374 to Pincemail, et al. and U.S. Pat. No. 7,267,946 to Runge et al. describing different methods for the detection of oxidative stress in an individual.

Inflammation may result in part from oxidative stress. Accordingly, further provided are methods for decreasing in an individual at risk for or having inflammation or an inflammatory response inflammation or an inflammatory response. The method includes administering to the individual a composition comprising an effective amount of a composition of the present invention sufficient to reduce inflammation or an inflammatory response. Accordingly, the invention provides compositions and methods of inflammatory diseases or reactions. In some embodiments, these inflammatory diseases are disorders of the bone joint such as osteoarthritis, osteoporosis, rheumatoid arthritis, and soft tissue rheumatism. The methods of the present invention can also be used to prevent and/or treat inflammatory skin diseases (e.g., atopic dermatitis, eczema, contact dermatitis, allergic dermatitis), skin irritation, inflammatory pulmonary disease or reactions (e.g., asthma, allergic rhinitis, chronic obstructive pulmonary disease, and adult respiratory distress syndrome), inflammatory musculoskeletal disease or reaction (e.g., soft tissue rheumatism, exercise-induced injury, rheumatoid arthritis, psoriatic arthritis, osteoporosis and osteoarthritis), inflammatory gastrointestinal disease or urogenital reaction (e.g., enterocolitis, gastritis, Crohn's disease, interstitial cystitis, vaginitis, and ulcerative colitis), autoimmune disease or reactions (e.g., inflammatory bowel disease, and psoriasis), muscle fatigue, osteoarthritis, rheumatoid arthritis, inflammatory bowel syndrome or disorder, skin inflammation, such as atopic dermatitis, contact dermatitis, allergic dermatitis, xerosis, eczema, rosacea, seborrhea, psoriasis, atherosclerosis, thermal and radiation burns, acne, oily skin, wrinkles, excessive cellulite, excessive pore size, intrinsic skin aging, photo aging, photo damage, harmful UV damage, keratinization abnormalities, irritation including retinoid induced irritation, hirsutism, alopecia, dyspigmentation, inflammation due to wounds, scarring or stretch marks, loss of elasticity, skin atrophy, gingivitis, and transplantation rejection reactions. The inflammation or inflammatory response may be chronic or acute. The inflammatory response is at least in part mediated by an antibody or at least in part mediated by cellular immunity. The treatment results in a reduction in severity of a symptom of inflammation (e.g., swelling, pain, headache, fever, nausea, skeletal joint stiffness, or tissue or cell damage). In yet another aspect, the treatment results in inhibition of antibody production or lymphoid cell proliferation. The composition may be formulated in any suitable form that is suitable for delivery, e.g. a pharmaceutically acceptable form with a carrier, excipient or adjuvant. In another embodiment, a composition is formulated for topical application for local prevention of inflammation and/or tissue damage consequent to inflammation (e.g., psoriasis, atopic dermatitis, etc.). As will be readily apparent to those of skill in the art, the compositions of the present invention can be used on their own to treat inflammation or an inflammatory response or alternatively, they can be used in combination with other known anti-inflammatory agents.

A variety of steroidal and nonsteroidal anti-inflammatory agents can be combined with a composition of the present invention and used to treat inflammation. Examples of suitable steroidal anti-inflammatory agents include, but are not limited to, corticosteroids, such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluocinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fluradrenolone acetonide, medrysone, amcinafel, amcinafide, betamethasone and the balance of its esters, chloroprednisone, chloroprednisone acetate, clocortolone, clescinolone, dichlorisone, difluprednate, flucloronide, flunisolide, fluoromethalone, fluperolone, flupreclnisolone, hydrocortisone valerate, hydrocortisone cyclopentylpropionate, hydrocortamate, pammethasone, prednisolone, prednisone, triamcinolone, and mixtures thereof may be used.

Examples of suitable nonsteroidal anti-inflammatory agents include, but are not limited to, piroxicam, isoxicam, tenoxicam, sudoxicam, CP-14,304, aspirin, disalcid, benorylate, trilisate, safapryn, solprin, diflunisal, fendosal, diclofenac, fenclofenac, indomethacin, sulindac, tolmetin, isoxepac, furofenac, tiopinac, zidometacin, acemetacin, fentiazac, zomepirac, clidanac, oxepinac, felbinac, mefenamic, meclofenamic, flufenamic, niflumic, tolfenamic acids, ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, tiaprofenic, phenylbutazone, oxyphenbutazone, feprazone, azapropazone, trimethazone and the like. Mixtures of these nonsteroidal anti-inflammatory agents can also be employed, as well as the pharmaceutically-acceptable salts and esters of these agents. Of the nonsteroidal anti-inflammatory agents, ibuprofen, ketoprophen, naproxen, flufenamic acid, mefenamic acid, meclofenamic acid, piroxicam and felbinac are preferred and ibuprofen, naproxen, and flufenamic acid are most preferred.

In preferred embodiments, the methods and compositions of the invention are used for treating (1) a skin disease, disorder, or condition such as aged skin related wrinkles, sun damaged skin, blocked pores, uneven pigmentation, skin roughness, acne, perfusion, and/or wounds, (2) musculoskeletal pain, musculoskeletal stiffness, decreased motion range, reduced mobility, (3) inflammation, (4) neurological damage such as Parkinson's disease or Alzheimer's disease, (5) cardiac tissue necrosis resulting from cardiac ischemia, (6) autoimmune neurodegeneration (e.g., encephalomyelitis), (7) acute lung injury such as in sepsis and endotoxemia, (8) neuronal damage resulting from ischemia (e.g., stroke, drowning, brain surgery) or trauma (e.g., concussion or cord shock), (9) muscle tissue damage, muscle regeneration, muscle fatigue, (10), radiation-induced damage and/or (11) cystic fibrosis. For example, in one embodiment of the present invention, a method of treating an oxidative stress condition in an individual with cystic fibrosis comprises the administering a composition an effective amount of a composition of the present invention by any suitable delivery method or formulation.

In another embodiment, the invention includes a method of increasing or maintaining the joint health of an individual, in some cases, under conditions of oxidative stress. Another aspect includes the treatment of joint diseases, disorders or conditions associated with inflammation, for example, synovitis, swelling, pain, headache, fever, nausea, skeletal joint stiffness, or tissue or cell damage, osteoarthritis, joint effusion, joint inflammation and pain, post operative arthroscopic surgery, osteochondrosis dessicans (OCD), traumatic injury, fractures, degenerative joint disease (DJD), rheumatoid arthritis, psoriatic arthritis, synovitis, lameness, post operative arthroscopic surgery, deterioration of proper joint function, the inhibition of metabolic activity of chondrocytes, and septic arthritis. Use of any of the compositions of the present invention may diminish the inflammatory response in the affected area so that joint health of an individual is restored or the affects of inflammation alleviated. In one embodiment, about 150 mg of BIO2 is administered three times a day for effective treatment of musculoskeletal pain, musculoskeletal stiffness, decreased motion range, reduced mobility.

Other dosages of composition administered is from about 100 mg/day to about 1000 mg/day. Thus it is contemplated that one may use, ranges from about 100 mg/day, 150 mg/day, 200 mg/day, 250 mg/day, 300 mg/day, 350 mg/day, 400 mg/day, 450 mg/day, 500 mg/day, 550 mg/day, 600 mg/day, 650 mg/day, 700 mg/day, 750 mg/day, 800 mg/day, 850 mg/day, 900 mg/day, 950 mg/day to about 1000 mg/day. The dosage may be taken once a day or 2, 3, 4, or more as appropriate to treat the disease, disorder or condition. It will be understood that the exact method of administration and dosages of administration will be decided and adjusted at the time of administration, depending on the individual needs of a subject, taking into consideration factors such as, age, disease, gender, performance status, etc., and such adjustments will be made by a trained physician. Therefore, the invention is in no way limited by the doses set forth.

According to another aspect of the invention, compositions of the invention may be used for general care, as well as treatment and prevention of diseases, disorders, and conditions of the skin. The compositions according to the present invention may be used for treatment of any disease, disorder or condition that affects the skin for example, wrinkles, including both fine superficial wrinkles and coarse deep wrinkles, skin lines, facial frown lines, expression lines, rhytides, dermatoheliosis, photodamage, premature skin aging, crevices, bumps, pits, large pores (e.g., associated with adnexal structures such as sweat gland ducts, sebaceous glands, or hair follicles), "orange-peel" skin appearance, dryness, scaliness, flakiness and/or other forms of skin unevenness or roughness; blemishes such as acne, pimples, breakouts; excess skin oil problems such as over production of sebum, oiliness, facial shine, foundation breakthrough; abnormal desquamation (or exfoliation) or abnormal epidermal differentiation (e.g., abnormal skin turnover) such as scaliness, flakiness, keratoses, hyperkeratinization; inadequate skin moisturization (or hydration) such as caused by skin barrier damage, environmental dryness; loss of skin elasticity (loss and/or inactivation of functional skin elastin) such as elastosis, sagging (including puffiness in the eye area and jowls), loss of skin firmness, loss of skin tightness, loss of skin recoil from deformation; non-melanin skin discoloration such as undereye circles, blotching (e.g., uneven red coloration due to, e.g., rosacea), sallowness (pale color), discoloration caused by telangiectasia or spider vessels; melanin-related hyperpigmented (or unevenly pigmented) skin regions such as age spots (liver spots, brown spots) and freckles; post-inflammatory hyperpigmentation such as that which occurs following an inflammatory event (e.g., as an acne lesion, in-grown hair, insect/spider bite or sting, scratch, cut, wound, abrasion, and the like); atrophy such as, but not limited to, that associated with aging or steroid use; other histological or microscopic alterations in skin components such as ground substance (e.g., hyaluronic acid, glycosaminoglycans, etc.), collagen breakdown and structural alterations or abnormalities (e.g., changes in the stratum corneum, dermis, epidermis, the skin vascular system such as telangiectasia or spider vessels); tissue responses to insult such as itch or pruritus; and alterations to underlying tissues (e.g., subcutaneous fat, cellulite, muscles, trabeculae, septae, and the like), especially those proximate to the skin, smoothing uneven or rough skin, soothing itchy, inflamed or irritated skin, improving skin atrophy, skin blemishes, acne erythema, acne, photodamage, atopic dermatitis, restoring or rejuvenating aged skin, damaged, scarred skin, lightening hyper-pigmented skin, increasing the rate of healing of wounds in or on the skin, as well as skin changed or damaged by extrinsic factors such as sunlight, radiations, air pollution, wind, cold, dampness, heat, chemicals, smoke, cigarette smoking. The compositions may be used for the treatment and prevention of various cosmetic conditions and dermatological disorders, for example, inflammation of the skin such as atopic dermatitis, contact dermatitis, allergic dermatitis, skin irritation, wrinkles, thin-skinning and the like. The term "wound" includes skin cuts, tears, lacerations, ulcers, abrasions, burns, punctures and the like in or on the skin. As shown in Example 11, the composition of BiovaDerm™ (BIO2) provide numerous benefits in the treatment of various cosmetic conditions and dermatological disorders such as wrinkles, sun damaged skin, blocked pores, uneven pigmentation, skin roughness, acne, and perfusion.

The compositions of the invention may also be applied to the skin, hair or nails for the treatment of changes associated with aging of skin, nail and hair; uneven and rough surface of skin; acne; irritation; dermatoses; eczema; psoriasis; itchy scalp and skin; warts; herpes; age spots; lentigines; melasmas; blemished skin; mottled skin; hyperkeratosis; hyperpigmented skin; skin thickening due to elastosis of photoaging; abnormal or diminished syntheses of collagen, glycosaminoglycans, proteoglycans and elastin as well as diminished levels of such components in the dermis; stretch marks; skin lines; fine lines; wrinkles; thinning of nail plate and hair; loss or reduction of nail and hair resiliency, elasticity and recoilability; lack of skin, nail and hair lubricants and luster; dull and older-looking nail and hair; fragility and splitting of nail and hair; and the like.

Thus in one aspect, the invention provides a method for regulating a skin condition by administering to the individual in need of treatment thereof a composition of the present invention in an effect amount to treat the condition. Regulating a skin condition includes prophylactically regulating and/or therapeutically regulating skin condition, including visible and/or tactile discontinuities in skin such as, but not limited to, regulating visible and/or tactile discontinuities in the texture of skin, reducing post-inflammatory hyperpigmentation, regulating non-melanin discoloration of skin, regulating moisturization and barrier properties of skin, regulating epidermal differentiation of skin, regulating exfoliation of skin, thickening of skin to reduce skin atrophy, regulating the elasticity of skin, reducing oily skin, regulating cellulite in skin, regulating pruritus in skin, and promoting wound healing in skin and decreasing scarring. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, discontinuities in skin. "Regulating the signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign). As used herein, prophylactically regulating such signs includes delaying, minimizing and/or preventing signs of skin aging. As used herein, therapeutically regulating such signs includes ameliorating, e.g., diminishing, minimizing and/or effacing signs of skin aging.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage (e.g., sunlight, UV, smoke, ozone, pollutants, stress, etc.). These signs may result from processes which include, but are not limited to, the development of textural discontinuities.

The compositions used in the methods of the invention may be "personal care products" such as health and cosmetic beauty aid products generally recognized as being formulated for beautifying and grooming the skin and/or hair. For example, personal care products include anti-wrinkle cream or acne products (e.g., lotions, skin creams, etc.), cosmetics, toiletries, and over-the-counter pharmaceutical products intended for topical or oral usage.

As described elsewhere, the composition of the present invention can be formulated for topical application. In a preferred embodiment, a composition of the present invention is added to a topical cosmetic formulation to diminish wrinkles and/or treat acne. In one embodiment, one FTU of about 10% weight cream of BIO2 is administered topically, preferably twice a day to treat wrinkles, aged skin, blocked pores, uneven pigmentation, skin roughness, acne, and/or perfusion. Other dosages of composition administered is from about 5% weight to about 10% or 15% weight of the composition of the invention in the carrier. Thus it is contemplated that one may use, ranges from about 5% weight, about 10% weight, about 15% weight, 20% weight, about 25% weight, about 30% weight, 35% weight, 40% weight, about 45% weight, about 50% weight, to about 60% weight of the composition of the invention to the carrier such as a cream. The dosage may be taken or applied once a day or 2, 3, 4, or more as effective to treat the disease, disorder or condition. It will be understood that the exact method of administration and dosages of administration will be decided and adjusted at the time of administration, depending on the individual needs of a subject, taking into consideration factors such as, age, disease, gender, performance status, etc., and such adjustments can made by one skilled in the art. Therefore, the invention is in no way limited by the doses set forth.

Agents can be added to the topical formulation for such secondary purposes as treating skin dryness, providing protection against light; other medications for treating dermatoses, preventing infection, reducing irritation, inflammation and the like. For example, products of the invention may include, in addition to a composition of the invention, other dermatologically active compounds and materials, including without limitation, sunscreen ingredients, alpha hydroxy acids, retinoids, beta hydroxy acids, anti-inflammatories, antibacterials, antifungals, antioxidants hydroxyacids, ketoacids and related compounds; phienyl alpha acyloxyalkanoic acids and derivatives thereof N-acetyl-aldosamines, N-acetylamino acids and related N-acetyl compounds; those that improve or eradicate age spots, keratoses and wrinkles; local analgesics and anesthetics; antiacne agents; antibacterials; antiyeast agents; antifungal agents; antiviral agents; antidandruff agents; antidermatitis agents; antihistamine agents; antipruritic agents; antiemetics; antimotionsickness agents; anti-inflammatory agents; antihyperkeratolytic agents; antiperspirants; antipsoriatic agents; antiseborrheic agents; astringents; cleansing agents; hair conditioners and hair treatment agents; antiaging and antiwrinkle agents; sunblock and sunscreen agents; skin lightening agents; depigmenting agents; vitamins; corticosteroids; tanning agents; hormones; retinoids; topical cardiovascular agents; corn, callus and wart removing agents; and other.

When the compositions according to the present invention are used for treating skin wounds, for example in aiding the healing of skin cuts, tears, lacerations, burns, punctures, and other wounds, examples of suitable cosmetic or other agents that may be combined with one or more oligosaccharide aldonic acids or related compounds include: hydroxyacids, ketoacids and related compounds; phenyl alpha acyloxyalkanoic acids and derivatives thereof N-acetyl-aldosamines, N-acetylamino acids and related N-acetyl compounds; analgesics and anesthetics; wound cleansers; antibacterials; antiyeast agents; antifungal agents; antiviral agents; anti-inflammatory agents; skin lightening agents; depigmenting agents; vitamins; burn relief agents; and corticosteroids. The administration of one or more compositions or agents, in accordance with the methods of the invention may occur together, concurrently, separately, sequentially, or a combination thereof. One skilled in the art is well versed in the art of testing for wound healing. See, Shimamura K, Nakatani T, Ueda A, Sugama J, Okuwa M. Relationship between lymphangiogenesis and exudates during the wound-healing process of mouse skin full-thickness wound. Wound Repair Regen. 2009 July-August; 17(4):598-605.

The compositions of this invention may be delivered topically by any means known to those of skill in the art that is suitable for delivery of the composition. The composition of this invention may further include a pharmaceutically, dermatologically, or cosmetically acceptable vehicle capable of functioning as a delivery system to enable the penetration of the composition into the skin or wound. Thus, any composition of the invention may be formulated in the form of a solution, suspension cream, oil, gel, liquid, emulsion, ointment, salve, a powder, a spray or other forms known to those of ordinary skill in the art such as a wound dressing, an adhesive-containing bandage, a dermal patch, a cotton roll bandage and the like. Preparation of such topical formulations are well described in the art of pharmaceutical formulations as exemplified, for example, by Remington's Pharmaceutical Science, Edition 17, Mack Publishing Company, Easton, Pa.

The compositions of this invention may also be administered by other routes as described elsewhere herein, for example, orally. Preferably, the compositions of the invention are applied to the skin over a period of time sufficient to affect skin-related processes, e.g., reduce wrinkles or repair sun-damaged skin. The methods of application in the present invention will depend on the ultimate intended use of the compositions. Generally, the effects of the application and use of the compositions of this invention become visible after approximately 4 weeks of treatment. It is preferable to apply the compositions of this invention in an effective amount once or twice per day. In one specific embodiment of the present invention, the topical cosmetic composition of the present invention can be formulated as a night cream or a night repair serum, which can be applied to the face of an individual before sleep or a period of bodily rest. In another specific embodiment of the present invention, the composition of the present invention is formulated as a facial mask, which can be applied to the face before sleep or bodily rest, left thereon for a sufficiently long period of time (e.g., overnight), and then rinsed off. The topical cosmetic compositions can be applied locally to selected skin areas in need of treatment. The topical cosmetic compositions can also be applied generally to facial skin or other parts of the human body to achieve the desired effects in such parts. The topical cosmetic compositions of the present invention may be applied to the skin on an as-needed basis, or according to a pre-set schedule. The topical cosmetic compositions of the present invention may be applied directly to clean skin, before application of any moisturizer, foundation, make-up, etc. Alternatively, such compositions can be applied over moisturizer, and optionally over foundation and/or make-up. The amount applied each time, the area of application, the duration of application, and the frequency of application can vary widely, depending on the specific need of the user. For example, the topical cosmetic compositions can be applied for a period of days to months or even years, and at a frequency ranging from about once per week to about five times per day. For another example, the compositions can be applied for a period of about six months and at a frequency ranging from about three times a week to about three times per day, and preferably about once or twice per day.

In some cases, such as strenuous exercise or injury, the level of reactive oxygen species (ROS) produced in muscle tissue may be elevated to a level that causes damage to muscle tissue such as skeletal muscle. Provided by the invention are methods for reducing or inhibiting muscle tissue damage resulting from oxidative stress, for example, from ROS.

The method includes administering to a subject/individual a composition comprising an effective amount of at least one composition of the present invention. Further provided are methods of preserving mitochondrial function in muscle tissue exposed to oxidative stress comprising the administration to a subject a composition comprising an effective amount of at least one composition of the present invention. In one example, an effective amount can inhibit or decrease the formation of reactive oxygen species and slow the progression of oxidative stress in muscle tissue that are exerted or are afflicted by a disorder. In another aspect, an effective amount can reduce, decrease, inhibit or abrogate muscle tissue damage due to reactive oxygen species (ROS), preserve mitochondrial function in muscle tissue exposed to ROS; and/or improve, prevent or rectify motor performance and/or muscle endurance in physiological conditions where such functions are compensated or a combination of these activities. Detection of ROS and RNS production muscle cells can be performed by various techniques including electron spin resonance, fluorescent assays, cyotchrome c reduction, chemiluminescence, hydroxylation of salicylate, and assays to measure nitration of phenylalanine or arginine.

The invention includes treating diseases, disorders, or conditions such as muscle injuries, muscular dystrophies, neuromuscular diseases, myasthenia gravis, multiple sclerosis, amyotrophic lateral sclerosis, age-related sarcopenia, muscle fatigue, decreased muscle endurance, loss of muscle function and the like in an individual in need of such treatment by administering an effective amount of a composition of the present invention. The methods may also be used to restore muscle health, for example, from muscle damage from injury or exercise, or to retain muscle health. In another aspect, the methods may be used for enhancing motor performance and/or muscle endurance in an individual comprising administering to a subject an effective amount of at least one composition of the present invention. Examples of such condition include muscular dystrophies, muscle injuries, neuromuscular disorders such as myasthenia gravis, multiple sclerosis, amyotrophic lateral sclerosis, age-related sarcopenia, muscle tissue wasting, decreased energy and immune impairment and the like. One skilled in the art would be familiar with techniques for evaluating the compositions effectiveness in treating these diseases, disorders, or conditions. See, for example, Moresi V, Garcia-Alvarez G, Pristerà A, Rizzuto E, Albertini M C, Rocchi M, Marazzi G, Sassoon D, Adamo S, Coletti D. Modulation of caspase activity regulates skeletal muscle regeneration and function in response to vasopressin and tumor necrosis factor. PLoS One. 2009; 4(5):e5570. Epub 2009 May 18.

Several routes for administration of the composition are contemplated and these include but are not limited to oral, intramuscular, parenteral, or intrathecal. Other suitable routes are described elsewhere herein. For example, the compositions may be consumed as a food, beverage, supplement, including sports food and/or drinks and feed for animals including pet food. Exemplary forms include but are not limited to bars, tablets, gels, pills or capsules. In addition to nutritional products suitable for consumption of humans, it is also possible to use at least one composition in feed for animals, such as livestock or companion animals.

In some embodiments, the dosage of composition administered is from about 100 mg/day to about 1000 mg/day. Thus it is contemplated that one may use, ranges from about 100 mg/day, 150 mg/day, 200 mg/day, 250 mg/day, 300 mg/day, 350 mg/day, 400 mg/day, 450 mg/day, 500 mg/day, 550 mg/day, 600 mg/day, 650 mg/day, 700 mg/day, 750 mg/day, 800 mg/day, 850 mg/day, 900 mg/day, 950 mg/day to about 1000 mg/day. Intermediate ranges are also contemplated, for example one may use 110 mg/day, or 270 mg/day, or 365 mg/day or 576 mg/day and so on. It will be understood that the exact method of administration and dosages of administration will be decided and adjusted at the time of administration, depending on the individual needs of a subject, taking into consideration factors such as, age, disease, gender, performance status, etc., and such adjustments will be made by a trained physician. Therefore, the invention is in no way limited by the doses set forth.

Upon formulation, solutions will be administered in a manner compatible with the dosage formulation and in such amount as is diagnostically or therapeutically effective. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. Local or regional administration, with respect to an inflamed muscle, also is contemplated. Finally, systemic administration may be performed. Delivery via syringe or catherization is also contemplated.

Embodiments of the invention also relate to methods for treating and/or preventing tissue and cell damage caused by reactive oxygen species (ROS) in mammals. More specifically, embodiments of the invention relate to the prevention and/or reduction of bone tissue and bone cell damage through the administration of a composition of the present invention.

In some embodiments, the invention described herein relates to methods for treating and/or preventing bone tissue and cell damage caused by reactive oxygen species in mammals, including humans. More specifically, the disclosure relates to the prevention of bone cell death and bone resorption through the administration of a composition of the present invention. In other embodiments, the invention relates to methods for reducing or preventing cell death or apoptosis in bone cells.

Bone cells include, for example, osteoclasts, osteoblasts, and osteocytes. In one embodiment, a method for treating or preventing reactive oxygen species (ROS)-mediated oxidative damage to bone cells and tissues of a subject is provided, comprising the step of administering a composition of the present invention that reduces the amount of ROS to a subject suffering from or at risk for a bone disease caused or exacerbated by ROS-mediated oxidative damage. In some embodiments the ROS-mediated damage is enzymatically produced damage. In alternative embodiments, the ROS-mediated damage is cellular derived, such as osteoclast-derived damage. In some embodiments, the amount of ROS is reduced by inhibiting the production or release of ROS. Although the compositions and methods are applicable to any bone disease, they are particularly relevant to the treatment of bone diseases selected from the group consisting of osteoporosis, including, but not limited to, type I and type II osteoporosis, age-related osteoporosis, disuse osteoporosis, diabetes-related osteoporosis, and steroid-related osteoporosis, periodontal disease, osteopenia, osteomalacia, osteolytic bone disease, primary and secondary hyperparathyroidism, multiple myeloma, metastatic cancers of the bone, for example, of the spine, pelvis, limbs, hip, and skull, osteomyelitis, osteoclerotic lesions, osteoblastic lesions, fractures, osteoarthritis, infective arthritis, ankylosing spondylitis, gout, fibrous dyplasia, and Paget's disease of the bone.

Subjects suffering from or at risk for bone loss can be identified by methods known in the art, such as, for example, by radiographic measurement of bone density, by evaluation of biochemical markers such as alkaline phosphatase, osteocalcin, urinary calcium, and urinary hydroxyproline, by bone biopsy with pathological assessment, and by assessment of family history. Examples of bone density techniques include, for example, single- and dual photon absorptiometry, quantitative computed tomography, dual x-ray absorptiometry, and ultrasonography. Preferred sites of analysis include the hip, wrist, and vertebrae. Other detection methods include low level x-ray on a finger or wrist, ultrasound of the heel, and CT scan of the spine. In still another embodiment of the invention, a method of reducing bone tissue damage associated with ROS includes administering an effective amount of a composition of the present invention to an individual. The amount of ROS related damage by inhibits the production of reactive oxygen species. In some embodiments, the ROS-mediated damage causes or exacerbates a bone disease. Examples of such bone diseases include, but are not limited to osteoporosis, including type I osteoporosis, type II osteoporosis, age-related osteoporosis, disuse osteoporosis, diabetes-related osteoporosis, and steroid-related osteoporosis, periodontal disease, osteopenia, osteomalacia, osteolytic bone disease, primary and secondary hyperparathyroidism, multiple myeloma, metastatic cancers of the bone, for example, of the spine, pelvis, limbs, hip, and skull, osteomyelitis, osteoclerotic lesions, osteoblastic lesions, fractures, osteoarthritis, infective arthritis, ankylosing spondylitis, gout, fibrous dyplasia, and Paget's disease of the bone.

Recent work has indicated that these and other bone diseases may be exacerbated by ROS. ROS can have direct effects on various cells within the bones leading to apoptosis. Another possible mechanism by which these molecules can damage bone cells and tissue may be related to the role of ROS in bone resorption. For example, ROS produced by osteoclasts may effectively suppress bone formation and bone healing. One skilled in the art would be familiar with assays to determine various aspects of bone healing. See, for example, Gadi Pelled, Ayelet Ben Arav, Colleen Hock, David G Reynolds, Cemal Yazici, Yoram Zilberman, Zulma Gazit, Hani Awad, Dan Gazit, Edward Schwarz. Tissue Engineering Part A. Online Ahead of Editing: Jul. 21, 2009.

One embodiment of the invention relates to compositions and methods for treating and/or preventing cellular and tissue damage caused by reactive oxygen species released by osteoclasts in the process of bone resorption. In some embodiments, the compositions and methods of the invention reduce ROS-mediated damage by inhibiting the production or release of ROS.

A variety of reactive oxygen metabolites (ROMs) are produced in the monovalent pathway of oxygen reduction. These ROMs are enzymatically produced by osteoclasts and phagocytes such as monocytes and polymorphonuclear neutrophils (PMNs) and frequently released in a respiratory burst. Neutrophils also produce ROMs constitutively. The constitutive production may contribute to ROS-mediated cellular damage. Hydrogen peroxide and other ROS play an important role in a host's immunological defenses. Nevertheless, ROS produced in excessive amounts or at inappropriate times or locations, act to damage a host's cells and tissues, and thus can be detrimental to the host.

Examples of environmental and industrial toxins which cause damage to bone tissue include, without limitation, cigarette smoke, caffeine, alcohol, detergents, petroleum products, radiation, diethanoloamine, sodium laurel sulfate, propylene glycol, pesticides such as DDT and mirex, food additives and preservatives, heavy metals, organic solvents such as formaldehyde and bromobenzene, and solvents such as dioxins, flurans, TCE, PCE, DCE, tetrachloroethylene, carbon tetrachloride, and vinyl chloride. As will be described in greater detail below, toxins also include many common drugs, such as steroids, chemotherapy drugs, hormones, and anticonvulsants. Damage to bone tissue results, at least in part, by the detrimental release of ROS within a host or subject in response to such insults. Accordingly, compositions and methods for treating damage to bone tissue caused by exposure to toxic substances are provided. In one example, the administration of a ROS production and formation inhibiting composition of the present invention is useful for the reduction in trauma to bone cells and tissues following exposure to industrial and/or environmental toxins.

Numerous medications have been associated with damage to the bones. Such drugs include any substance or substances which act upon the bones to cause tissue damage. Examples of medications that have been associated with bone loss include, without limitation, corticosteroids, such as betamethasone, budesonide, cortisone dexamethasone, hydrocortisone, methylprednisolone, prednisolone, prednisone, and triamcinolone; cancer treatments, such as hormone therapy, including, for example, androgen deprivation in prostate cancer, orchiectomy, hormone therapy such as reduced estrogen and/or progesterone for breast cancer or metastatic breast cancer; thyroid hormone, such as thyroxine, for hyperthyroidism; anticonvulsants, such as barbituates, phenoarbital, phenyloin, and benzodiazepines; and lupus and Crohn's disease treatments.

Accordingly, a composition of the present inventions can be administered to an individual who is concurrently taking a drug or drugs which cause toxic side effects to mitigate bone loss caused by the drug. The administration of a composition of the invention is likewise useful for ameliorating damage to bone tissue caused or exacerbated by bacterial, or viral infections. *Staphylococcus aureus, Streptococcus pyogenes, Haemophilus influetazae, Myobacterium tuberculosis*, salmonellas and coliform bacteria, *Pseudomonas aeruginosa, Treponema pallidum*, and *Escherichia coli* are just a few examples of a species of pathogenic bacteria which invades the bones and causes tissue damage.

Accordingly, in one embodiment, a composition of the present invention and methods for minimizing damage to bone tissue associated with bacterial, fungal, or viral infections are provided. A composition of the present invention may be administered alone or in combination with an antibiotic. The administration can be by either local or by systemic delivery and any other suitable method known to one skilled in the art. Other methods of administration may also be suitable, such as oral administration.

For oral administration, the composition of the present inventions can be in powder form or incorporated into a tablet, aqueous or oil suspension, dispersible powder or granule, microbead, emulsion, hard or soft capsule, syrup or elixir. Administration of the composition of the present inventions can also be accomplished via parenteral delivery through subcutaneous, intravenous, intraperitoneal, or intramuscular injection, intraocular, oral, transdermal, intranasal, or rectal and can utilize direct hypodermic or other injection or infusion means, or can be mediated by a controlled release mechanism or any suitable method known to one skilled in the art.

The present invention also relates to any pharmaceutical, dermatological, medical, nutritional or cosmetic compositions comprising a composition, fraction thereof or component obtained from eggshell membrane using a process of the present invention. The composition may include an effective amount of at least one or more components obtained from solubilized eggshell membrane. In one aspect, the composition is a hydrolyzed, water-soluble protein composition from the eggshell membrane, one of more fractions thereof such as a retentate fraction or permeate fraction of components having the desired molecular mass (kDa), or individual components, e.g. proteins or polysaccharides, thereof. The composition can be any dose or effective amount of the composition that is safe and efficacious to achieve the desired result. As the diseases, disorders or conditions that would benefit from these compositions are well known, the compositions may be designed such that they contain appropriate levels effective for treatment of the particular disease, disorder or condition. The compositions may generally be used in any formulation that is effective for treatment and the intended mode of administration. For example, compositions of elastin or collagen such as Type I collagen, Type V collagen, and/or Type X collagen, for use in dermatological, medical or cosmetic treatments may be formulated in topical, oral or injectable forms and the like. Compositions comprising solubilized proteins for use in nutritional or medical applications may be formulated in any suitable form, e.g. aqueous or dried, and administered by any effective route, such as orally or intramuscularly. As appreciated by one skilled in the art, compositions of the present invention can be administered in a variety of ways including oral, enteral, parenteral, topical, sublingual, by inhalation spray, rectal and other appropriate routes of administration, such as oral, subcutaneous, transdermal, transmucosal, iontophoretic, intravenous, intramuscular, intraperitoneal, intranasal, subdural, rectal, and the like.

In other preferred embodiments, formulations of this invention are pharmaceutical compositions suitable for administration via various routes, preferably orally or topically, and for therapeutic and/or prophylactic administration.

A composition of the present invention, such as a pharmaceutical composition, may comprise different types of acceptable carriers depending on whether it is to be administered in solid, liquid or aerosol form, and whether it needs to be sterile for such routes of administration as injection. A composition of the present invention, such as a pharmaceutical composition, can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 18th Ed. Mack Printing Company, 1990, incorporated herein by reference). A number of suitable formulations for use in the present invention are found in Remington's Pharmaceutical Sciences (Mack Publishing Company, Philadelphia, Pa., 17th ed., 1985) and in Dermatological Formulations: Percutaneous absorption, Barry (Ed.), Marcel Dekker Inc., 1983, both incorporated herein by reference. Moreover, for a brief review of methods for drug delivery, see Langer, Science 249:1527-1533, 1990, which is also incorporated herein by reference.

The compositions or products of the invention can be applied to any affected part of the body. It will be appreciated that the present methods of treatment can be applied alone or in combination with treatments for these conditions. The compositions useful in the present methods can be administered one time or multiple times, depending on the composition, the severity of the disease, disorder, or condition, and the initial response of the condition to the treatment, for example, alleviating a symptom. For example, the compositions can be administered 1, 2, 4, or more times per day, and can be administered every 1, 2, 4, 7, or more days. Such treatments can be administered for a limited duration, or indefinitely until the condition has resolved. The compositions can be applied locally as a "leave on" product, meaning that the composition is applied to the individual and allowed to remain indefinitely at the site of application, or as a "wash off" product, meaning that the composition is allowed to remain at the site of application for a limited amount of time, e.g., for a certain number of seconds, minutes, hours, etc, and then removed.

Compositions containing solubilized components from eggshell membranes of the present invention may be in any form suitable for the intended mode of administration, including, for example, a powder, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents. The compositions of the present invention may be administered orally, parenterally, sublingually, by inhalation spray, rectally, or topically in dosage unit formulations containing conventional nontoxic pharmaceutically acceptable or physiologically acceptable carriers, adjuvants, and vehicles as desired. Topical administration may also involve the use of emulsions, creams, ointments, transdermal patches or ionophoresis devices. The term parenteral as used herein includes subcutaneous injections, intravenous, intramuscular, intrasternal injection, or infusion techniques.

As described elsewhere herein, the compositions useful in the present methods can be administered to an individual using a variety of routes, such as oral or parenteral, and formulations. One skilled in the art will be well versed in selecting the appropriate formulation and route in which to administer a composition of the invention to an individual, such as a human, mammal, animal, companion animals or farm animals. In some cases, any of the present compositions are administered to an individual at the local site of the disease, disorder or condition, whether by local injection, topical administration, or any other suitable method. As such, administration of the compositions can be achieved in various ways, including by topical application of the composition to the site of the disease or condition, i.e., direct application of a formulation to the affected skin. If desired, compositions can be formulated for injection and injected locally at the site of the disease or condition, e.g., local subcutaneous injection at the site of the disease, for example, to treat a joint disorder.

For any composition used in a method of the invention or product of the invention, a therapeutically effective amount or dose can be estimated initially in vitro or in vivo data. Initial dosages can also be formulated by comparing the effectiveness of the compounds used in the methods of the present invention in model assays with the effectiveness of known compounds. One having ordinary skill in the art could readily determine an effective dosage in humans or other mammals and animals.

Dosage amount and interval may be adjusted individually to provide levels of the composition which are sufficient to achieve and/or maintain their desired effect. One having skill in the art will be able to optimize therapeutically or prophylactically effective amounts or dosages without undue experimentation.

This invention can be better understood by reference to the following non-limiting examples. It will be appreciated by those skilled in the art that other embodiments of the invention may be practiced without departing from the spirit and the scope of the invention as herein disclosed and claimed.

EXAMPLE

The present invention is further defined in the following Examples, in which parts and percentages are by weight and degrees are Celsius, unless otherwise stated. The disclosure of each reference set forth herein is incorporated herein by reference in its entirety.

Example 1

Shown below is data resulting from the analysis of various samples of the resulting protein composition obtained by solubilizing avian eggshell membrane using a process of the present invention.

As indicated below, the solubilized protein composition was spray dried (SD), freeze dried (FD), or paddle dried (PD). Paddle dried is a common technique used by some egg breaking facilities to dry eggshells on a commercial scale.

The total protein (TP) concentration of the solubilized protein composition was measured using Leco instruments (St Joseph, Mich.) following the Association of Analytical Chemists (AOAC) protein by combustion method 990.03. The solubilized protein composition was determined "as is" in its current physical state as well as on a "dry basis".

The ash content was determined using AOAC method 942.05. The percent solubility of the resulting protein composition was determined using standard techniques. The percent collagen, elastin and sulfated glycans were determined using various commercially available assays, for example, colorimetric kits such as Sircol, Fastin, Blyscan assays (Biocolors Ltd, Northern Ireland). Percent hyaluronic acid was determined by measuring uronic acid by a carbazole method. The amino acid profile was performed by Eurofins Scientific, Inc. (Des Moines, Iowa). A Standard Plate Count (SPC) procedure was used to determine the presence of bacteria in each of the samples, as indicated below by SPC.

The measurement of color was determined using the Hunter L, a, b standard color scale, which is described below. Hunter L, a, b values are standard color scale values that indicate differences in brightness, hue and saturation using a standard color system which relates lightness as L values, and hue and croma as a combination of a and b values on a coordinate scale, where a represents redness-greenness and b represents yellowness-blueness. L values describe the degree of darkness, where a value of 100 equals white and that of 0 equals black. a-values describe the degree of redness, which increases with an increasing a-value. b-values describe the degree of yellowness, which increases with increasing b-value. L, a, b and opacity theory and measurement are further described in the Hunter Lab Instruction Manual Hunter. L, a, b and color scale values and opacity may be measured using a colorimeter available from Hunter Associate Laboratory, Inc. of Reston, Va., U.S.A. or the Color Machine Model 8900 available from Pacific Scientific.

As shown in FIG. 2, wet, dry or frozen membranes were put into a stainless (316) tank and 12% NaOH was added and the mixture was incubated at 32-40° C. overnight. After hydrolysis the mixture was cooled to 38-45° F. to slow continued hydrolysis. The mixture was centrifuged to separate eggshells from solubilized proteins. The centrifuged solubilized proteins were then dialyzed through 3,000 MWCO membranes until ash was reduced to a conductivity reading of 2-4 mS/cm. The proteins were then pH adjusted with 12% acetic acid to a pH of 6.8-8. The pH adjusted protein mixture was then concentrated to a solids content of 25% to 30% at which time it could be spray dried or freeze dried. Tables 1 and 2 below show the percent analysis of samples from the resulting composition.

TABLE 1

Percent analysis of sample compositions.

| Sample | Type (SD, FD, PD) | Leco TP % as-is | Leco TP % dry basis | Ash % as-is | Ash % dry basis | Moist % | Solids % | Solubility % | Collagen % |
|---|---|---|---|---|---|---|---|---|---|
| 1 | FD | 90.45 | 94.50 | 6.67 | 6.97 | 4.29 | 95.71 | 95.40 | 16.96 |
| 2 | FD | 91.56 | 95.64 | 6.96 | 7.27 | 4.27 | 95.73 | 92.26 | 18.49 |
| 3 | FD | 90.25 | 92.61 | 7.35 | 7.54 | 2.55 | 97.45 | 99.70 | 17.62 |
| 4 | SD | 91.66 | 100.03 | 6.22 | 6.79 | 8.37 | 91.63 | 98.16 | 15.44 |

TABLE 2

Percent analysis of sample compositions.

| Sample | Hyaluronic Acid % | Elastin % | Sulfated Glycans % | SPC's (cfu's/g) | Salmonella (neg/25 g) | Color (L) | Color (a) | Color (b) |
|---|---|---|---|---|---|---|---|---|
| 1 | 0.13 | 29.52 | ND | <100 | neg | 63.41 | 2.41 | 18.88 |
| 2 | 0.17 | 24.20 | ND | <100 | neg | 63.78 | 3.35 | 20.64 |
| 3 | 0.15 | 22.50 | 0.01 | 1,800 | neg | 57.47 | 0.57 | 15.42 |
| 4 | 0.20 | 24.52 | ND | <1,000 | neg | 86.37 | −0.48 | 11.08 |

As shown in FIG. 3, various soluble protein compositions may be obtained using various membrane sizes in accordance with the methods of the present invention. A typical test analysis of the compositions obtained from processing 600 pounds of eggshell membranes obtained from eggs from chicken (*Pullus*) using various sized membranes are shown in Tables 3-6.

Example 2

Process for Making the Product Referred to as Composition A in FIG. 3A

The process for making the product referred to as Composition A includes adding eggshell membranes (wet, dry or frozen) to a jacketed 316 stainless tank followed by 5% sodium hydroxide. The tank contents were heated to 50° C. while stirring until hydrolysis was completed which is 3 to 4 hours. The tank stirrer was shut off after hydrolysis was complete and eggshell is allowed to settle out. (Approx. 30 min.) Hydrolysis was monitored until no membrane was visible and only the eggshell remains.

The hydrolyzed membrane was pumped through a 250-500 μm membrane and into the centrifuge for separation of eggshell fines from the supernatant liquid.

After centrifuging, the supernatant liquid was pumped into a 1,000 Dalton to 10,000 Dalton membrane system, where the ash was removed until it measures less than 4 milliSiemens/cm at which time the pH was adjusted to pH 6.8-7.6 with 0.5% acetic acid and dialyzed with one more volume of water. The dialyzed, pH adjusted supernatant was concentrated to 20-30% solids and then spray dried in a nozzle dryer to generate Composition A. FIG. 3A and Table 3 below shows the resulting composition.

TABLE 3

Percent analysis of components of Composition A.

| Composition A Analysis | % |
|---|---|
| Total protein | 92.59 |
| Ash | 6.51 |

TABLE 3-continued

Percent analysis of components of Composition A.

| Composition A Analysis | % |
|---|---|
| Moisture | 5.00 |
| Solids | 95.01 |
| Collagen | 32.17 |
| Hyaluronic Acid | 1.59 |
| Elastin | 21.62 |

Further analytical results indicate that the following amino acids are present in the following Composition A:

TABLE 4

Percent analysis of amino acid present in the Composition A.

| Amino Acid | (%) |
|---|---|
| Tryptophan | 3.53 |
| Cystine | 2.47 |
| Methionine | 3.79 |
| Aspartic Acid | 8.33 |
| Threonine | 3.08 |
| Serine | 3.30 |
| Glutamic Acid | 14.61 |

TABLE 4-continued

Percent analysis of amino acid present in the Composition A.

| Amino Acid | (%) |
| --- | --- |
| Proline | 9.85 |
| Glycine | 4.38 |
| Alanine | 2.25 |
| Valine | 7.51 |
| Isoleucine | 3.47 |
| Leucine | 4.72 |
| Tyrosine | 1.72 |
| Phenylalanine | 1.57 |
| Total Lysine | 5.99 |
| Histidine | 3.23 |
| Arginine | 6.58 |
| Hydroxyproline | 0.22 |

Example 3

Process for Making the Product Referred to as Composition B in FIG. 3A

Egg membranes (wet, dry or frozen) were added to a jacketed 316 stainless tank followed by 5% sodium hydroxide. The tank contents were heated to 50° C. while stirring until hydrolysis was completed which is 3 to 4 hours. The tank stirrer was shut off after hydrolysis was complete and eggshell is allowed to settle out. (Approx. 30 min.) Hydrolysis was monitored until no membrane is visible and only the eggshell remains.

The hydrolyzed membrane is pumped through a 250-500 μm membrane and into the centrifuge for separation of eggshell fines from the supernatant liquid.

After centrifuging, the hydrolyzed membrane was diafiltered through a 100,000 molecular weight cutoff membrane. The retentate was saved and conductivity was reduced from 140 milliSiemens/cm to 4 milliSiemens/cm and concentrated to 25-30% solids and spray dried. The results are shown in the following table and in FIG. 3A.

TABLE 5

Percent analysis of components of the Composition B composition.

| Composition B Analysis | % |
| --- | --- |
| Total protein | 94.10 |
| Ash | 6.67 |
| Moisture | 4.27 |
| Solids | 95.73 |
| Collagen | 23.70 |
| Hyaluronic Acid | 1.27 |
| Elastin | 37.95 |

Example 4

Process for Making the Product Referred to as Composition C in FIG. 3B

The permeate was collected from the 100,000 molecular weight cutoff membranes and dialyzed with 10,000 molecular weight membranes. Conductivity was reduced from 140 milliSiemens/cm to 4 milliSiemens/cm and concentrated to 25-30% solids and spray dried. The resulting composition is provided in FIG. 3B and Table 6 below.

TABLE 6

Percent analysis of components of the Composition C composition.

| Composition C Analysis | % |
| --- | --- |
| Total protein | 90.18 |
| Ash | 8.09 |
| Moisture | 5.14 |
| Solids | 94.86 |
| Collagen | 15.93 |
| Hyaluronic Acid | 2.00 |
| Elastin | 2.35 |

Example 5

Process for Making BIO1 and BIO2 Products and Composition Analysis

BIO1

As used herein, BIO1 refers to a an eggshell membrane composition obtained as a 3 kDa permeate using a 3 kDa membrane and nanofilter to generate a nanofilter retentate using the methods described herein. SKU313 and 314 refer to a spray dried form of BIO1 and freeze dried form of BIO1 respectively. The Bio1 composition has molecules and components lower than 3 kDa, but higher than 450 Da.

The process for making the product referred to as BIO1 includes adding eggshell membranes (wet, dry or frozen) to a jacketed 316 stainless tank followed by 5% sodium hydroxide. The tank contents were heated to 50° C. while stirring until hydrolysis was completed which is 3 to 4 hours. The tank stirrer was shut off after hydrolysis was complete and eggshell is allowed to settle out. (Approx. 30 min.) Hydrolysis was monitored until no membrane was visible and only the eggshell remains.

The hydrolyzed membrane was pumped through a 250-500 μm membrane and into the centrifuge for separation of eggshell fines from the supernatant liquid.

After centrifuging, the supernatant liquid was pumped into a 1,000 Dalton to 3,000 Dalton membrane system, where the ash was removed until it measures less than 4 milliSiemens/cm at which time the pH was adjusted to pH 6.8-7.6 with 1.2% acetic acid and dialyzed with one more volume of water. The permeate passing through the 3 Kda membrane was subjected to a nanofilter and the NF retentate was dialyzed, pH adjusted supernatant was concentrated to 20-30% solids and then spray dried in a nozzle dryer to generate BIO1 or freeze dried. The table below shows the resulting composition.

BIO2

As used herein, BIO2 refers to an eggshell membrane composition obtained as a 3 kDa retentate using a 3 kDa membrane using the methods described herein. SKU309, BiOvacore, Ovacore, Biova Flex, OvaFlex, BiovaDerm and Ovaderm all refer to a spray dried form of BIO2 and the terms are used interchangeably herein. The Bio2 composition has molecules and components higher than 3 kDa.

The process for making the product referred to as BIO2 includes adding eggshell membranes (wet, dry or frozen) to a jacketed 316 stainless tank followed by 5% sodium hydroxide. The tank contents were heated to 50° C. while stirring until hydrolysis was completed which is 3 to 4 hours. The tank stirrer was shut off after hydrolysis was complete and eggshell is allowed to settle out. (Approx. 30 min.) Hydrolysis was monitored until no membrane was visible and only the eggshell remains.

The hydrolyzed membrane was pumped through a 250-500 μm membrane and into the centrifuge for separation of eggshell fines from the supernatant liquid.

After centrifuging, the supernatant liquid was pumped into a 1,000 Dalton to 3,000 Dalton membrane system, where the ash was removed until it measures less than 4 milliSiemens/cm at which time the pH was adjusted to pH 6.8-7.6 with 1.2% acetic acid and dialyzed with one more volume of water. The 3 kDa retentate was dialyzed, pH adjusted supernatant was concentrated to 20-30% solids and then spray dried in a nozzle dryer to generate BIO2. The table below shows the resulting composition.

| Test | Result-SKU309 | Result-SKU313 |
|---|---|---|
| Total Protein | 91.90% | 83.71% |
| Ash | 7.39% | 16.40% |
| Moisture | 4.18% | 4.09% |
| Collagen | 25.85% | 3.07% |
| Hyaluronic Acid | 1.63% | 3.78% |
| Elastin | 22.11% | negligible |
| Chondroitins | 0.03% | none detected |
| Glucosamine | 0.82% | 0.44% |
| ORAC$_{hydro}$ | 423 μmoleTE/g | 829 μmoleTE/g |
| Aerobic Plate Count | <10,000 cfu/g | <10 cfu/g |
| Salmonella | negative/25 g | negative/25 g |
| Coliforms | <10 MPN/g | <3 MPN/g |
| E. coli | <10 MPN/g | <3 MPN/g |
| B. cereus | <3 MPN/g | <3 MPN/g |
| Yeast | <10 cfu/g | <10 MPN/g |
| Mold | <10 cfu/g | <10 MPN/g |
| S. aureus | <10 cfu/g | not tested |
| Arsenic | 0.03 ppm | <0.02 ppm |
| Lead | 0.05 ppm | 0.02 |
| Cadmium | <0.01 ppm | <0.01 |
| Mercury | <0.01 ppm | <0.01 |
| Bulk Density | 0.22 g/cc | not tested |
| Calcium | 0.35% | not tested |
| Water Activity | 0.1 | not tested |

Amino Acid Analysis:

| | SKU # | |
|---|---|---|
| Amino Acid (%): | 309 | 314 |
| Tryptophan | 4.12 | 2.37 |
| Cystine | 3.00 | 1.91 |
| Methionine | 4.18 | 3.56 |
| Aspartic Acid | 8.16 | 8.34 |
| Threonine | 2.94 | 2.40 |
| Serine | 3.06 | 3.54 |
| Glutamic Acid | 12.02 | 12.62 |
| Proline | 8.87 | 8.04 |
| Glycine | 4.91 | 7.41 |
| Alanine | 2.30 | 3.06 |
| Valine | 7.06 | 5.78 |
| Isoleucine | 3.30 | 2.72 |
| Leucine | 4.48 | 4.56 |
| Tyrosine | 1.88 | 1.53 |
| Phenylalanine | 1.65 | 1.46 |
| Total Lysine | 6.07 | 0.63 |
| Histidine | 3.37 | 3.01 |
| Arginine | 5.63 | 4.28 |
| Hydroxyproline | 0.33 | 1.50 |
| Lysine Available | 4.71 | 0.63 |
| Lysine Unavailable | 1.37 | 0.55 |
| Aspartic Acid (Free) | <0.01 | 0.08 |
| Threonine (Free) | <0.01 | 0.14 |
| Serine (Free) | <0.01 | <0.01 |
| Glutamic acid (Free) | <0.01 | 0.02 |
| Proline (Free) | <0.01 | 0.32 |
| Glycine (Free) | <0.01 | <0.01 |
| Alanine (Free) | <0.01 | 0.01 |
| Cystine (Free) | <0.01 | 0.06 |
| Valine (Free) | <0.01 | <0.01 |
| Methionine (Free) | <0.01 | 0.04 |
| Isoleucine (Free) | <0.01 | 0.08 |
| Leucine (Free) | <0.01 | <0.01 |
| Tyrosine (Free) | <0.01 | 0.16 |
| Phenylalanine (Free) | <0.01 | <0.1 |
| Lysine (Free) | <0.01 | <0.01 |
| Histidine (Free) | <0.01 | <0.01 |
| Arginine (Free) | <0.01 | <0.01 |

Example 6

Lipoxygensase Inhibition

Lipoxygenase is an enzyme involved in inflammation. A lipoxygenase inhibitor screening kit was obtained from Cayman Chemical, and used according to the guidelines of the manufacturer. In this assay, a purified 15-Lipoxygenase enzyme from soybean was mixed with the substrate arachidonic acid in the absence versus presence of each of the BIO1 and BIO2 fractions. The hydroxyperoxides that are produced as a result of the lipoxygenase reaction generated a colored product and the light absorbance was measured. FIG. 4 shows the dose-dependent inhibition of hydroxyperoxide formation by BIO1 versus BIO2. Both complementary fractions show activity.

As shown in FIG. 4, in the lipoxygenase inhibition assay, both products did well but BIO1 (1:10) had a 68% inhibition in which the data was highly statistically significant (P<0.0009). BIO2 (1:10) was still capable of inhibiting lipoxygenase by 12% at the highest dose tested; this data was highly statistically significant (P<0.0003).

Both the low-molecular weight composition of BIO1 and high-molecular weight composition of BIO2 fractions of eggshell membrane (ESM) contains compounds able to inhibit the generation of reactive oxygen species by the enzyme lipoxygenase.

Both the low-molecular weight composition of BIO1 and high-molecular weight composition of BIO2 fractions of ESM contained compounds able to interfere with the generation of hydroxyperoxyl free radicals generated by the enzymatic function of lipoxygenase.

Example 7

Inhibition of the Formation of ROS

The BIO1 and BIO2 fractions from ESM contains compounds able to inhibit the formation of Reactive Oxygen Species (ROS) by human polymorphonuclear (PMN) cells.

Freshly purified human polymorph nucleated cells (PMN) were used for testing ROS formation. This cell type constitutes approximately 70% of the white blood cells in humans. PMN produce high amounts of ROS upon certain inflammatory stimuli. PMN cells are complex and capable of reacting in several ways upon exposure to natural products as follows:
1. Passive absorption of antioxidants into the cells, leading to neutralization of ROS within the cells;
2. Active signaling by compounds in the natural product (for example glucans) leading to increased ROS production;

3. Active signaling by compounds in the natural product leading to a reduced inflammatory response by the cell and therefore a reduced production of ROS.

When PMN cells are exposed to a natural product, it is possible that an increase in spontaneous ROS formation may occur, if the product possesses immune activating properties, including a stimulation of PMN cell anti-bacterial activity. Alternatively, a decrease may be observed, which means the natural product reduced the PMN cell spontaneous ROS formation.

PMN cells were isolated by applying heparinized peripheral venous blood on top of a double-gradient of 3 ml Histopaque 1119 and 3 mL of Histopaque1077. This was centrifuged for 25 minutes at 2400 rpm. The plasma and PBMC was removed, and the PMN fraction harvested. The PMN cells were washed twice in phosphate-buffered saline without calcium or magnesium, and resuspended in RPMI 1640. Serial dilutions of BIO1 and BIO2 were added to PMN cells and the cells were incubated for 20 minutes. Subsequently, cells were washed twice to remove the ESM fractions, and the precursor dye DCF-DA was added. The PMN cells were incubated with DCF-DA for 1 hour, after which time unabsorbed DCF-DA was removed by two washes. Oxidative burst was then induced, either by adding $H_2O_2$ or by adding the bacterial peptide f-MLP for 45 minutes. Cells were washed, resuspended in RPMI 1640, and kept on ice until samples were acquired by flow cytometry. Oxidative damage, such as what happens during a reactive oxidative burst in PMN cells, transforms the DCF-DA precursor dye into a fluorescent dye. The fluorescence intensity of the cells is a measure of the intensity of the oxidative burst.

Freshly purified human PMN were exposed to the test products. During the incubation with the test products, any antioxidant compounds able to cross the cell membrane can enter the interior of the PMN cells. Then the cells were washed, loaded with the DCF-DA dye, which turns fluorescent upon exposure to reactive oxygen species. Oxidation is triggered by addition of $H_2O_2$. The fluorescence intensity of the PMN cells was evaluated by flow cytometry. The low fluorescence intensity of untreated control cells served as a baseline and PMN cells treated with $H_2O_2$ alone serve as a positive control. If the fluorescence intensity of PMN cells exposed to the extract, and subsequently exposed to $H_2O_2$, is reduced compared to $H_2O_2$ alone, this indicates that the test product has anti-inflammatory effects. In contrast, if the fluorescence intensity of PMN cells exposed to a test product is increased compared to $H_2O_2$ alone, this indicates that a test product has pro-inflammatory effects.

FIGS. 5A and 5B show that both products inhibited formation of ROS by PMN cells, both under normal culture conditions and under oxidative stress. As shown in FIG. 5A, In this case both products were capable at helping reduce the baseline level of ROS. BIO1 (1:10) helped reduce spontaneous ROS formation by 58%, this data was highly significant ($P<0.0000005$). BIO2 ($1:10^3$) was also capable at reducing spontaneous ROS formation by 46% and this data was highly statistically significant ($P<0.000002$). FIG. 5B illustrates the amount of protection a natural product can provide when a PMN cell has been exposed to oxidative stress, in this case by being treated with $H_2O_2$. In this case both products were capable at inhibiting ROS formation under conditions of oxidative stress across all dilutions tested. Both BIO1 (1:10) and BIO2 (1:10) reduced ROS formation by 37%; BIO1 data was highly statistically significant ($P<0.000003$) and BIO2 data was also highly statistically significant ($P<0.00002$).

Example 8

Migratory Behavior
3. Effect on PMN Cell Chemotactic Migration Towards Three Chemo-attractants.

The PMN cell is a highly active and migratory cell type. The migratory behavior of this cell type is divided into at least two types:
 a) random migration and
 b) directed migration.
Random migration is part of normal immune surveillance, whereas directed migration happens towards specific chemoattractants.

We have established a migration test where both types of migration are tested in parallel. Furthermore, the directed migration is tested towards three distinctly different chemotactic compounds:
 i) Bacterial peptide f-Met-Leu-Phe;
 ii) The inflammatory cytokine Interleukin-8 (IL-8); and
 iii) Leukotriene B4 (LTB4).
The migration towards f-MLP is a reflection of anti-bacterial immune defense mechanisms, whereas the migration towards IL-8 and LTB4 reflects mechanisms involved in the escalation of the inflammatory response.

We have found interesting evidence during evaluation of several natural products that some test products may specifically reduce directed PMN migration towards the inflammatory mediators IL-8 and/or LTB4 while allowing PMN migration towards bacterial peptide as part of the normal anti-bacterial immune defense.

The differential effect on PMN cell random migration as well as chemotactic migration towards three different inflammatory chemo-attractants: bacterial fmlp, IL-8, and Leukotriene B4 were tested.

Enhancement of PMN Cell Random Migratory Behavior

The migration of polymorphonuclear (PMN) cells was tested using dual chamber 96-well migration plates. PMN cells are plated in the top chambers. A filter separates the two chambers, and 3 micron pores allow migration of cells from top to bottom chamber. This in vitro assay is designed to mimic the migration of cells from blood (top chamber) into tissue (bottom chamber).

PMN cells were plated in the top chambers with and without BIO1. Control wells included cells un-exposed to product and without chemoattractant in the bottom wells. The random migration activity of PMN cells resulted in measurable amounts of PMN cells in the bottom chambers. The relative amount of cells was determined by staining of the cells in the bottom chambers using the CyQuant fluorescent probe. When BIO1 was added to PMN cells in the top chambers, the random migratory activity of the PMN cells was increased. BIO2 had a lesser effect.

Freshly purified PMN cells were set up in cultures in double-chamber migration plates, where the bottom chamber mimics tissue, and the top chamber mimics the blood stream. Cells are plated in the top chambers with and without test product, and the chemo-attractants will be present in the bottom chambers. Control wells included cells un-exposed to test products and without chemo-attractant in the bottom wells, and allow evaluation of baseline random migration. All assays were performed in triplicates, and repeated 3 times.

Inhibition of PMN Cell Migration Towards the Inflammatory Mediator Leukotriene B4

The migration of polymorphonuclear (PMN) cells was tested using dual chamber 96-well migration plates. PMN cells are plated in the top chambers and different chemotactic agents can be added to the bottom chamber. A filter separates the two chambers, and 3 micron pores allow migration of cells from top to bottom chamber. This in vitro assay is designed to mimic the migration of inflammatory cells from blood (top chamber) into tissue (bottom chamber), with inflammatory mediators as chemoattractants.

PMN cells were plated in the top chambers with and without serial dilutions of BIO1 or BIO2 and the inflammatory chemo-attractant Leukotriene B4 (LTB4) was present in the bottom chambers. Control wells included cells un-exposed to product and without chemoattractant in the bottom wells. The directed migration of PMN cells resulted in measurable amounts of PMN cells in the bottom chambers. The relative amount of cells was determined by staining of the cells in the bottom chambers using the CyQuant fluorescent probe. When BIO1 was added to PMN cells in the top chambers, the migration of the PMN cells towards LTB4 in the bottom chambers was reduced. BIO2 had a lesser effect.

FIGS. 6A and 6B show that both products were capable at increasing random migration cellular behavior linked to normal immune surveillance. BIO1 (1:10) increased immune surveillance by 81% and was highly statistically significant ($P<0.000003$). BIO2 (1:10) increased immune surveillance by 52% and was also statistically significant ($P<0.008$).

Higher doses of BIO1 and BIO2 increased migration towards the bacterial peptide f-MLP (FIG. 6F) implicating that an anti-microbial response was triggered. BIO1 (1:10) increased migration by 59% and this data was statistically significant ($p<0.002$). BIO2 ($10^2$) also increased migration by 67% and was highly statistically significant ($p<0.000006$). Surprisingly, the more BIO2 was diluted a decrease in migration was observed.

BIO1 treatment of PMN cells resulted in a mild increase of PMN cell migration towards IL-8. BIO1 ($10^3$) increased migration by 27% and the data was statistically significant ($P<0.01$). For BIO2 there were two different and interesting effects. At the highest dose of BIO2 tested, an increased migration was seen. However, when BIO2 is further diluted an anti-inflammatory effect was observed, as BIO2 treatment of PMN cells resulted in a reduction in the migration towards LTB4. BIO2 ($10^4$) decreased migration by 69% and was highly significant ($P<0.0002$). See FIG. 6E.

BIO2 was capable at reducing migration across all dilution sets and the strongest reaction ($10^4$) was shown to reduce migration by 72%, the data was statistically significant ($P<0.02$). BIO1 ($10^3$) was not able to reduce migration but did increase migratory activity by 55%; data was not significant. See FIGS. 6C and 6D.

Discussion:
Lipoxygenase inhibition: BIO1 strongly inhibited Lipoxygenase enzymatic activity, whereas BIO2 mildly inhibited Lipoxygenase enzymatic activity.
Inhibition of ROS formation: Both products performed equally well in inhibiting oxidative stress-induced ROS formation.
PMN cell migration:
BIO1 activated several aspects of PMN cell migratory behavior.
Both BIO1 and BIO2 elicited strong anti-microbial migratory behavior in PMN cells.
BIO2 showed the best data in terms of inhibiting PMN cell migration in response to the inflammatory mediators IL-8 and LTB4, with a particular strong and clear inhibition of LTB4-mediated migration.

Example 9

Evaluation of Protection of Cellular Viability (Protection from Programmed Cell Death (Apoptosis)) in the Absence Versus Presence of Oxidative Stress Oxidative damage can trigger premature cellular death by a mechanism called apoptosis (programmed cell death). This death pathway can be monitored by highly specific cellular markers. Protection from apoptosis can be monitored as delay or absence of these markers.

Apoptosis is a carefully regulated process of cell death that occurs as a normal part of cellular development. In contrast to necrosis, a form of cell death resulting from acute cellular injury, apoptosis is carried out in an ordered process.

The human vascular anticoagulant, annexin V, is a $Ca^{2+}$-dependent phospholipid-binding protein that has a high affinity for phosphatidylserine (PS). In normal viable cells, phosphatidylserine is located on the cytoplasmic surface of the cell membrane. However, in apoptotic cells, PS is translocated from the inner to the outer leaflet of the plasma membrane, thus exposing PS to the external cellular environment. Annexin V labeled with a fluorophore can identify apoptotic cells by binding to PS exposed on the outer leaflet. AnnexinV-FITC was used to label apoptotic cells. Co-staining with 7AAD, which only stains cells at a late phase of cell death where the cell membrane is compromised, allows analysis to distinguish early and late apoptosis. Cells staining only with 7AAD, without Annexin V, reflect necrotic cells.

Among freshly isolated human peripheral blood mononuclear cells, a proportion is already on an apoptotic path. When cultured in vitro, these cells will continue the apoptotic process. Early apoptosis is reversible. By culturing freshly purified human lymphocytes with and without test product, and then staining for apoptotic cells, we were comparing the ability of the test product to rescue cells already on the path to apoptosis.

In parallel, $H_2O_2$ was added to trigger oxidative stress-induced apoptosis, and assess whether the test product was able to protect the viability of cells that were under severe oxidative stress.

The testing was performed where each testing condition, including each serial dilution of test product, was performed in triplicate. The experiment was repeated three times using PBMC from different blood donors. Samples were stored dark and acquired by flow cytometry within 4 hours. Acquisition was performed using FACSCALIBUR™ flow cytometer and CELL-QUEST™ software. Analysis of fluorescence intensity of the markers was performed using FLOWJO™ software.

Results: Evaluation of Protection of Cellular Viability (Protection from Programmed Cell Death (Apoptosis)) in the Absence Versus Presence of Oxidative Stress.

When examining the effects of cell viability/death of an overnight incubation, six parameters were analyzed:
1. Percentage of viable cells under normal cell culture (FIG. 8A);
2. Percentage of viable cells under oxidative stress (FIG. 9A);
3. Percentage of total apoptosis under normal cell culture (FIG. 8B);
4. Percentage of total apoptosis under oxidative stress (FIG. 9B);
5. Percentage of necrotic cells under normal cell culture (FIG. 8C);
6. Percentage of necrotic cells under oxidative stress (FIG. 9C).

Viable cells (UT) are the percent of cells that exhibit very low staining for both Annexin V and 7AAD after an overnight incubation without product. This value is compared to cells that have been incubated overnight with serial dilutions of product.

In the absence of $H_2O_2$ treatment, both BIO1 and BIO2 increased the percentage of viable cells following overnight incubation. These mild changes were not statistically significant.

The decrease in percent viable cells seen with the highest doses of BIO1 and BIO2 (10 g/L) most likely reflect adverse effects of both products on cell viability at this high a concentration.

Under oxidative stress, BIO1 (1 g/L) increased the percent of viable cells by up to 30% above the untreated (UT) negative control samples. This increase was statistically significant (P<0.03 for 1 g/L). When cells were placed under the same oxidative stress but now in the presence of BIO2 (0.1 g/L), an increase of 15% viable cells was seen, however the data was not statistically significant. Once again at 10 g/L, BIO2 had an adverse effect on cell viability.

Total apoptosis is the combination of all cells involved in early apoptosis and late apoptosis. When cells were treated with BIO1 overnight in the absence of $H_2O_2$, BIO1 (0.1 g/L) reduced the amount of total apoptosis by 14% below that of the untreated (UT) negative control samples, however the data was not statistically significant. BIO2 (0.1 g/L) also reduced the amount of total apoptotic cells, however, this reduction was not statistically significant. At the 10 g/L dose, overnight treatment with BIO2 resulted in an increase in total apoptosis.

Under oxidative stress BIO1 (1 g/L) reduced the percent of total apoptotic cells by up to 9% below that of the untreated (UT) control samples (at 1 g/L), however the data was not statistically significant. The highest dose of BIO1 (10 g/L) increased the percentage of cells undergoing apoptosis in response to oxidative stress. BIO2 did not rescue cells from apoptosis under oxidative stress but rather had an adverse effect on cell viability at the 2 highest doses tested.

When cells were incubated overnight with BIO1 (0.1 g/L) necrotic cells were reduced by 10% below that of the untreated control samples, however this small change was not statistically significant. BIO2 at the 1 g/L dose reduced the percent of necrotic cells by 32%. This reduction only reached borderline statistical significance (P<0.07). At the highest dose tested (10 g/L), both products increased cell necrosis.

Cells undergoing oxidative stress induced by treatment with $H_2O_2$, were protected from necrosis in the presence of BIO1 in a clear dose-dependent manner. At 10 g/L BIO1 treatment resulted in a highly statistically significant reduction of 47% (P<0.0006).

When cells were treated with BIO2 (1 g/L) followed by exposure to $H_2O_2$ a 27% reduction in percent necrotic cells was observed and was statistically significant (P<0.005 at 1 g/L). The highest dose of BIO2 tested (10 g/L) had an adverse effect on cells leading to increased necrosis.

Under conditions of oxidative stress, BIO1 increased the percent of viable cells above the untreated (UT) negative control samples, both by reducing the percent of cells in apoptosis and of cells in necrosis. BIO2 also reduced the amount of total apoptotic and necrotic cells at some doses tested on cells.

Example 10

Protection of Mitochondrial Function Under Conditions of Oxidative Stress

Mitochondria are the intracellular organelles responsible for producing cellular energy. Decreased mitochondrial function has been associated with ageing, inflammatory conditions, and degenerative illnesses. This assay measures mitochondrial function, and examines whether a test product contains compounds capable of supporting healthy mitochondrial function, as well as protecting mitochondrial function in cells under oxidative stress.

Freshly purified human peripheral blood mononuclear cells (PBMC) were cultured in the absence versus presence of serial dilutions of test product, either without further treatment or in the presence of oxidative stress. After incubation, the level of mitochondrial function was measured by staining with the marker MitoTracker-Red, which becomes fluorescent as a result of, and in proportion to, mitochondrial function. Therefore, the resulting fluorescence intensity was proportional to mitochondrial function, and was evaluated by flow cytometry. A decrease in fluorescence intensity reflects a reduction of mitochondrial function, as mitochondria were damaged by oxidative stress. If the presence of test product protects mitochondrial function, then higher fluorescence intensities will be observed.

Mitochondrial function is measured through the use of a mitochondria-specific fluorescent dye. The mean fluorescence intensity (MFI) of the MitoTracker-Red dye reflects the number and functionality of mitochondria within a cell. When a cell is producing more mitochondria or the activity of mitochondria within the cell increases, an increase in the mean fluorescence will be seen.

FIG. 7 shows that when cells were treated overnight with BIO1 (10 g/L) an increase in mitochondrial function was observed. BIO2 also had an effect, even thought to a lesser degree. The protective effect was seen both under normal culture conditions and under conditions of oxidative stress.

Evaluation of protection of mitochondrial function in the absence versus presence of oxidative stress.

When cells were treated overnight with BIO1 (10 g/L) a 17% increase in mitochondrial function was observed (P<0.01). When BIO2 (10 g/L) was added to cells in an overnight incubation, mitochondrial function was increased by 6% above untreated cells, however the data was not statistically significant. See FIG. 7A.

When cells were cultured in the presence of product and $H_2O_2$ it was observed that BIO1 (1 g/L) increased mitochondrial function by 25% above cells treated with $H_2O_2$ in the absence of product. This increase was statistically significant (P<0.03). Under the same conditions, treatment with BIO2 (1 g/L) increased mitochondrial function by 6%, however the data was not statistically significant. See FIG. 7B.

Example 11

Anti-Wrinkle Effect of the BiOvaDerm™ (Bio2, 309) Fractions In Vivo. The effects of ESM fractions on facial wrinkles was measured.

A single-site open-label Pilot Study was conducted to evaluate the effectiveness of BiovaDerm™ in reducing aged skin related wrinkles and its impact on sun damaged skin. The composition described in this study is a topical skin cream, which was formulated with 10% of BiOvaDerm™ (Bio2) by weight suspended in a base cream "carrier" to facilitate application. Twenty three (23) subjects were enrolled and evaluated in three groups that differed in the length of time they followed a daily treatment regime:

Group 1 consisted of six (6) subjects that were instructed to apply study product for one (1) week. Group 1 used the cream daily for one week after which they were asked to return the cream and continue their normal regime observing the exclusion criteria. Subject evaluations were conducted at initial visit, at the end of week 1.

Subject evaluations continued to facilitate capture of "rebound" data for 4 weeks after product application had ceased.

Group 2 consisted of nine (9) subjects and they were instructed to apply study product for two (2) weeks. Group 2 used the cream daily for two weeks after which they were asked to return the cream and continue their normal regime observing the exclusion criteria. Subject evaluations were conducted at initial visit, week 2 and weeks 4 and 6. This again facilitated capture of "rebound" data four weeks after product application had ceased.

Group 3 contained eight (8) subjects and they were instructed to apply study product for four (4) weeks. Group 3 used the cream daily for four weeks after which they were asked to return the cream and continue their normal regime observing the exclusion criteria. Subject evaluations were conducted at initial visit, weeks 2 & 4, and again at weeks 6 and 8 to facilitate capture of "rebound" data four weeks after product application had ceased.

Daily application of the BiovaDerm™ has demonstrated:
28% reduction of deep wrinkles within 4 weeks in Group 3.
19% reduction of deep wrinkles within 2 weeks in Group 2.
30% reduction of deep wrinkles within 1 week in Group 1.
Effectiveness of treatment continued beyond two weeks from last product application.

The positive effect was long-lasting and continued after use of the cream was discontinued. 1-2 weeks after cessation of treatment the skin started to revert to its pre-treatment state. It was observed that measurable effect of the cream was still discernable after 4 weeks in wrinkle reduction, improved skin smoothness and luminance and reduced acne. Subject comments corroborated these clinical observations in detail. There were no negative/adverse observations from study subjects or clinical staff.

Treatments & Mode of Administration Topical-BiOvaDerm™: Hydrolyzed egg membrane powder of Bio2 in a cream base was applied to the face of Subjects who have aged and/or sun damaged skin. After skin has been cleaned and dried in the morning and evening (at least 8 hours between applications), subject removed 1FTU (finger tip unit) from one ounce jar, and applied dab of cream to face, covering temple to outward corner of eyes, and around lips and chin where fine lines are found.

Study Endpoints

The effectiveness endpoint was the week 2, 4, 6, and 8 measurements of facial skin wrinkles. The principal investigators utilized a Moritex/BTBP skin analyzer which scans the face and sends quantitative data to specialized software which calculates the number of, and extent of wrinkle severity and depth, Skin Complexion Health, Skin Texture and laxity/tone changes, and UV damage.

Effectiveness Analysis

The effectiveness of the treatment was assessed by measuring the change in the prevalence and depth of wrinkles, the complexion health; redness of the skin, and the smoothness and tone of the face before, during, and after use of BiOvaDerm™ (Bio2) Cream.

Subjects

Subjects 18 years of age or older who had aged and or sun damaged skin were qualified for participation in the trial, according to specific inclusion and exclusion criteria. Subjects who met all of the eligibility criteria were invited to participate. Study personnel (clinical investigator or research nurse/coordinator) explained the study to each subject, including procedures involved in the treatment, risk and benefits, alternative treatments and his/her rights as a study subject. The subject was given the consent form and allowed as much time as he or she required to read and decide on participation. Subject who decided to participate, were asked to sign the consent form. Subjects who signed the consent form and received study treatment were considered enrolled. Subjects who withdraw after signing the consent but before any study treatment were recorded on a dropout log.

Subjects Inclusion Criteria
1. Subject must be 18 years of age.
2. Subject must be available for and willing to attend all evaluation visits.
3. Subject must be able and willing to give informed consent.
4. Subjects should have aged and/or sun damaged skin, determined by subjective observation.
5. Subjects must be willing to use appropriate birth control for duration of trial.

Subjects Exclusion Criteria
1. Subjects should not be utilizing accutane, or other skin treatment drugs or topicals such as Isotretinoin, oral antibiotics, topical antimicrobials, (Azelaic acid, Benzoyl Peroxide, Clindamycin, Erythromycin, Sodium Sulfacetamide, or topical retinoids, like Adapalene, Tazarotene, or Tretinoin).
2. Subject has known allergy to eggs or egg products.
3. Pregnant and breastfeeding women.
4. Subject is unwilling to forgo dermatologic or Aesthetic skin treatments for the duration of the study.
5. Subject is involved in any other research study involving an investigational product (drug, device or biologic) or a new application of an approved product, within 30 days of screening.

Criteria for Evaluation

Subjects were given the face cream and instructed to apply it twice per day as a thin layer on the face in the morning and before bed at night. At two week intervals, the subjects attended the clinic at which time they were asked to wash their faces to remove any makeup, oil or cream and their faces were scanned with the Moritex/BTBP skin analyzer (Clarity Pro Face Scanning System) and data pertaining to skin and wrinkles was obtained. The analyzer measures facial wrinkles and quantifies deep wrinkles, fine wrinkles and emerging wrinkles in separate categories by computerized image analysis of wrinkle lines in very high resolution photographs, and skin color, smoothness tone, excessive oil, and UV damage of the face. The data was gathered by clinicians trained on the use of the face scanner. With few exceptions all data was gathered by the same clinician in the same clinic environment.

Summary Findings

Application of the BiOvaDerm™ (BIO2) cream resulted in a quite positive and sometimes dramatic reduction in wrinkles, and other skin conditions. (See charts below) The positive effect was long-lasting and continued even after use of the cream was discontinued.

After 1-2 weeks the skin started to revert to its pre-treatment state, but even after 4 weeks the effect of the cream was still discernible as a reduction in wrinkles, an improvement of skin smoothness and luminance and reduced acne. Subject comments corroborated these observations in detail.

There were no negative/adverse observations from Clinical staff, or comments from study subjects.

Adverse Effects & Safety Monitoring

Subjects were also instructed to record any changes in overall health, as well as any discomfort associated with the application of the cream. Subjects were asked to bring their diary to all evaluation visits for review with the investigators. The subject self-assessment diary was examined at each visit providing the opportunity to note and discuss with the subjects any discomfort or other adverse events that might have been recorded. In addition, at baseline, week 2, and week 6, blood chemistry, CBC, and other lab results were taken. Heart rate and blood pressure measurements were also taken and results were recorded. PI or Clinic staff noted any event or result which fell outside normal range, or expectation, (related or not related to study) the PI or Clinic staff were instructed that should an event be observed, they were to provide such information to the subject and recommended that they discuss the findings with their private physician.

Effectiveness Analysis

Topical cream Effectiveness scan evaluations occurred at week 2, week 4, and week 6 following initiation of treatment in each subject. At the evaluation visit the investigator conducted face scans and computerized analyses of aged and/or sun damaged skin to assess improvements in complexion health, pore & pigment health, redness, or areas where there was UV damage.

The clinician used a Moritex/BTBP Skin Analyzer (Moritex/BTBP, Inc., San Jose, Calif.) which scans the face using high resolution photography and derives highly quantitative data pertaining to above described conditions. By making one or two baseline scans per subject, it was possible to quantify future changes in facial skin for subjects applying the cream in the study.

Statistical Considerations

Subjects were not randomized. Subjects were recruited to participate who had aged and sun damaged skin, and who agreed to utilize the BiOvaDerm™ (Bio2) Topical skin treatment formulation. A smaller number of normal younger subjects were also recruited.

Results

A total of 23 subjects were recruited and enrolled in the trial. Clinician used a Skin Analyzer (Moritex/BTBP) which scans the face and sends quantitative data to specialized software which uses advanced image analysis techniques to quantify the status of facial skin.

The study population varied in age and amount of wrinkles Actual wrinkle index values were of limited use for comparative purposes and so for presentation all data are presented as percentages of the baseline measurements for the population at the start of the study Assessment of Skin Health Results Effect of BiOvaDerm™ Cream on Wrinkles and Facial Redness

TABLE 1

Effect of BiOvaDerm ™ Cream use on Wrinkles and Redness

| | | Baseline | 1 Week | 2 weeks | 3 weeks | 4 weeks | 5 weeks |
|---|---|---|---|---|---|---|---|
| Face Cream 1 week use | Emerging(E) | 100% | 81% | 81% | 95% | 94% | 99% |
| | Fine (F) | 100% | 83% | 92% | 83% | 108% | 87% |
| | Deep (D) | 100% | 70% | 95% | 82% | 80% | 48% |
| | Redness | 100% | 110% | 102% | 110% | 87% | 104% |
| | (E + F + D) | 100% | 76% | 90% | 86% | 91% | 73% |
| | n = | 6 | 4 | 2 | 4 | 1 | 3 |

| | | Baseline | 1 Week | 2 weeks | 4 weeks | 6 weeks | 8 weeks |
|---|---|---|---|---|---|---|---|
| Face Cream 2 weeks use | Emerging(E) | 100% | | 83% | 85% | 101% | |
| | Fine (F) | 100% | | 89% | 84% | 98% | |
| | Deep (D) | 100% | | 81% | 83% | 100% | |
| | Redness | 100% | | 99% | 105% | 100% | |
| | (E + F + D) | 100% | | 84% | 84% | 100% | |
| | n = | 9 | | 9 | 7 | 4 | |
| Face Cream 4 weeks use | Emerging(E) | 100% | | 78% | 101% | 81% | 98% |
| | Fine (F) | 100% | | 110% | 107% | 106% | 107% |
| | Deep (D) | 100% | | 93% | 72% | 76% | 87% |
| | Redness | 100% | | 112% | 106% | 114% | 113% |
| | (E + F + D) | 100% | | 92% | 87% | 83% | 94% |
| | n = | 8 | | 8 | 8 | 8 | 8 |

FIG. 11 is a graph depicting the average percentage change from baseline wrinkle measurements for 8 subjects who used the cream for 4 weeks and were followed an additional four weeks after stopping use.

A general overview of the effects of the treatment can be seen in the graph depicting the average percentage change from baseline wrinkle measurements for 8 subjects who used the cream for 4 weeks (FIG. 11). Subjects discontinued use of creams at week 4 as is indicated by the vertical line. The data for weeks 6 and 8 represent values measured after use of product had been discontinued.

This data, representing group 3, demonstrated that use of the cream resulted in:
- 28% reduction of deep wrinkles after 4 weeks of daily use
- 17% overall reduction in all wrinkles (together) at 6 weeks (two weeks after cessation of use).

As was anticipated, the use of the cream resulted in an increase of fine lines concordant with the observation that Emerging, Fine and Deep wrinkles are not independent since loss of deep wrinkles can increase fine lines, and similarly, loss of fine lines can increase the measures of emergent lines. Due to the nature of the face scanning device, measurement error was also expected to be greatest in emergent wrinkle measurements followed by Fine lines and then Deep wrinkles.

FIG. 12 is a Graph depicting the average percentage change from baseline wrinkle measurements for 9 subjects over who used the cream for 2 weeks and were followed for another four weeks after stopping use.

Group 2 subjects discontinued cream application after two weeks. These 9 subjects showed similar changes (10%) to those in Group 3 (8%) for All Wrinkles [E+F+D] after two weeks of application. Subjects were asked to discontinue use of creams after 2 weeks and this is indicated by the vertical line. The data for weeks 4 and 6 represent values measured after use of product had been discontinued.

This data, representing Group 2, demonstrated:

19% reduction of deep wrinkles after 2 weeks of daily use
15% overall reduction in all wrinkles two weeks after cessation of use.

As was anticipated, the use of the cream resulted in an increase of fine lines concordant with the observation that Emerging, Fine and Deep wrinkles are not independent since loss of deep wrinkles can increase fine lines, and similarly, loss of fine lines can increase the measures of emergent lines. Due to the nature of the face scanning device, measurement error was also expected to be greatest in emergent wrinkle measurements followed by Fine lines and then Deep wrinkles.

FIG. 13 Graph depicting the average percentage change from baseline wrinkle measurements for 6 subjects who used the cream for 1 weeks and were followed for another four weeks after stopping use.

Group 1 subjects discontinued cream use after 1 week. These 6 subjects showed a reduction in all categories of wrinkles (24% All Wrinkles [E+F+D]). Subjects discontinued use of creams at week 1 and this is indicated by the vertical line. The data for weeks 2, 3, and 4 represent values measured after use of product had been discontinued.

Complexion

The Tables below summarize the face scan analyses as percentage change from Baseline scans done at commencement of the study. Three variables relevant to Complexion are Pigment Evenness, Redness and Luminescence. Each table summarizes the results for each Group of subjects who used the cream for different lengths of time. All subjects were followed for 4 weeks after stopping daily use of the cream.

| Group 1 | | Baseline | 1 Week | 2 weeks | 3 weeks | 4 weeks | 5 weeks |
|---|---|---|---|---|---|---|---|
| Face Cream 1 week use | Pigment Evenness | 100% | 101% | 128% | 117% | 102% | 148% |
| | Redness | 100% | 127% | 118% | 129% | 101% | 121% |
| | Luminescence | 100% | 92% | 84% | 90% | 67% | 99% |
| | n = | 6 | 4 | 2 | 4 | 1 | 3 |

| Group 2 | Baseline | 1 Week | 2 weeks | 4 weeks | 6 weeks | | 8 weeks |
|---|---|---|---|---|---|---|---|
| Face Cream 2 weeks use | 100% | | 108% | 95% | 247% | Pigment Evenness | — |
| | 100% | | 113% | 123% | 149% | Redness | — |
| | 100% | | 109% | 113% | 229% | Luminescence | — |
| | 9 | | 9 | 7 | 4 | n = | |

| Group 2 | | Baseline | 1 Week | 2 weeks | 4 weeks | 6 weeks | 8 weeks |
|---|---|---|---|---|---|---|---|
| Face Cream 4 weeks use | Pigment Evenness | 100% | | 109% | 125% | 114% | 117% |
| | Redness | 100% | | 112% | 110% | 114% | 113% |
| | Luminescence | 100% | | 103% | 103% | 100% | 99% |
| | n = | 8 | | 8 | 8 | 8 | 8 |

Excess Sebum, Acne, and Pore Inflammation

The Tables below summarize the face scan analyses as percentage change from Baseline scans done at commencement of the study. Three variables relevant to Pore Health are Sebum level (oiliness), Acne and Pore Inflammation. Each table summarizes the results from Groups of subjects that used the cream for different lengths of time. All subjects were followed for 4 weeks after stopping daily use of the cream.

| Group 1 | | Baseline | 1 Week | 2 weeks | 3 weeks | 4 weeks | 5 weeks |
|---|---|---|---|---|---|---|---|
| Face Cream 1 week use | Excess Sebum | 100% | 110% | 123% | 204% | 110% | 57% |
| | Acne | 100% | 48% | 48% | 60% | 82% | 37% |
| | Inflammation | 100% | 57% | 67% | 43% | 63% | 13% |
| | n = | | 6 | 4 | 2 | 4 | 1 | 3 |

| Group 2 | | Baseline | 1 Week | 2 weeks | 4 weeks | 6 weeks | 8 weeks |
|---|---|---|---|---|---|---|---|
| Face Cream 2 weeks use | Excess Sebum | 100% | | 79% | 80% | 10% | |
| | Acne | 100% | | 123% | 56% | 28% | |
| | Inflammation | 100% | | 181% | 92% | 92% | |
| | n = | 9 | | 9 | 7 | 4 | |

| Group 3 | | Baseline | 1 Week | 2 weeks | 4 weeks | 6 weeks | 8 weeks |
|---|---|---|---|---|---|---|---|
| Face Cream 4 weeks use | Excess Sebum | 100% | | 110% | 112% | 68% | 79% |
| | Acne | 100% | | 115% | 102% | 95% | 78% |
| | Inflammation | 100% | | 134% | 148% | 115% | 138% |
| | n = | 8 | | 8 | 8 | 8 | 8 |

Redness increased in all groups and did not appear to be affected by cessation of cream use. Luminescence and Pigment Evenness also increased, resulting in a discernible smoothness, color and patina to the skin in some subjects.

Use of BiOvaDerm™ Cream appeared to have a direct effect on Pore health related parameters but less pronounced effect on Complexion. Changes in Pore Health parameters appeared to be more closely correlated with the use of the cream. Pore inflammation and acne as measured by the scanner, both increased during the period of cream use and decreased when cream applications were discontinued falling to levels below the initial value for these measurements. The net effect therefore was an improvement in Pore health and reduction in excess sebum (blocked pores), Acne and related pore inflammation.

FIGS. 14-15: Pore Health And Complexion Related Measurements. [Read from "0" Baseline to the Vertical Line which Represents the Stopping Point]

Improvements in redness, pigment evenness, and luminescence all increased over the course of the study and were commented on by subjects in interviews and diaries. The effect on these parameters seemed to continue forward as even after subjects stopped applying the cream, an upward trend in skin complexion and health was observed.

Discussion

Wrinkle Count, Prevalence and Severity:

Subjects in the study ranged in age from their twenties to sixties. Subject by subject, the actual indices for the three sub-categories of wrinkles varied widely. To compare and contrast the measurements, the data was expressed as percentages of the baseline measurement for each subject. The Baseline measurement (made at commencement of the study) was set at 100% and all subsequent measurements compared to that starting value. Summary tables and graphs included present the group averages of those changes.

Wrinkles decreased in the majority of subjects in response to cream application within one week. The response times varied among the subjects and some subjects showed no apparent wrinkle reduction. An interesting finding is that the data suggests a linear relationship between amount of time treatment is applied and biological effect over this time frame. The average reduction of wrinkles after 2 weeks of use was approximately 50% of the reduction seen after 4 weeks.

Changes in wrinkle indices are not independent since they may interconvert in response to treatment. In wrinkle improvement, Deep wrinkles are expected to smooth out into Fine wrinkles, which convert to Emergent wrinkles (and vice versa when cream application is stopped). This suggests an explanation for the two week lag between the maximum effect of Deep wrinkles versus the maximum effect of combined (All Wrinkles summed) measurements.

The results obtained in this study are highly significant from scientific, cosmetic, and marketing perspectives when compared to other published studies of anti-wrinkle creams. A very highly publicized double blind randomized controlled study carried out in the UK (Watson et al., 2009) in which subjects with aged skin used a plant based anti-aging formulation, it was found that at 12 months, 70% of the participants showed an improvement in facial wrinkles compared to the start of the study versus a statistically modeled null prediction of 33% of people expected to show improvement using the control (vehicle) cream for 12 months. The improvement in the test group was described as "clinically significant" but researchers did not observe any other benefits of the test product over the control. For example, there were no improvements in the amount of abnormal coloration of the skin and both the test and control products produced similar improvements in skin roughness from the start of the study (see this article from the National Health Services Choices; www.nhs.uk/news/2009/04April/Pages/Facecreamreduceswrinkles.aspx, of the United Kingdom).

FIG. 16: Sum of Wrinkle Measurements (Deep+Fine+Emergent) for Six Subjects Expressed as Percentage of Initial Pre-Use Value.

Cream use was started day 1 and discontinued after 2 weeks Group 2. An overview of the effects of the treatment can be seen in the graph of Total Wrinkles index (Deep+Fine+Emergent) over the course of the study. The wrinkle data are plotted as percentages of the value calculated for the baseline scan taken during first visit 1 for this group (i.e. before the subjects started the treatment). Subjects were asked to discontinue use of creams at 2 weeks to test effect of non-use after daily application. The data for later visits represent wrinkles analysis after product use had been discontinued. In this group, use of the cream resulted in a reduction of wrinkles that was detected after 2 weeks of daily use and varied from 5% to 63% reduction among the subjects. KEY: JR, LE, NR, RC=Initials of study subjects Effect of BiOva Cream FIG. 17: Example of wrinkle measurements (Deep). Four subjects expressed as percentage of initial pre-use value (day 1). Cream use started day 1 and discontinued at 2 weeks. In these subjects, use of the cream resulted in reduction of deep wrinkles detected after 2 weeks of daily use and varied 20% to 60% reduction among the subjects. When cream was discontinued, (at 2 weeks), the skin started to revert to its pretreatment state was seen over the following 4 weeks.

Effect of Biova Cream on Fine Lines

FIG. 18: Wrinkle Measurements (Fine) for Four Subjects Expressed as Percentage of Initial Pre-Use Value. Cream Use was Started on Day 1 and Discontinued after 2 Weeks.

In most subjects, use of the cream resulted in a reduction of wrinkles that was detected after 2 weeks of daily use and varied among the subjects. When use of the cream was discontinued, (Visit 3), the skin started to revert to its pre-treatment state over the following 4 weeks (visits 4 and 5). When analyzing deep wrinkle reductions, the scanner tends to identify more of the fine wrinkles, as a result the effect is less clear in this measurement category. After discontinuing cream use for a month, only 7 subjects in the study had returned to values statistically the same as their starting values (i.e. >90% of their baseline measurement). All other study subjects had wrinkle values ranging from 44%-90% of their baseline measurement.

Effect of Biova Cream on Emerging Wrinkles

In most subjects, use of the cream resulted in a reduction of wrinkles that was detected after 2 weeks of daily use and ranged from 5% to 50% reductions among the subjects. When use of the cream was discontinued, (Visit 3), the skin started to revert to its pre-treatment state over the following 4 weeks (visits 4 and 5). After discontinuing cream use for a month, only 7 subjects in the study had returned to values statistically the same as their starting values (i.e. >90% of their baseline measurement). All other study subjects had wrinkle values ranging from 44%-90% of their baseline measurement.

Complexion Health

Complexion health showed specific trends in response to cream use:

Redness increased in all three groups and stayed elevated throughout the study. It did not appear to be directly affected by cessation of cream use, suggesting an increase in perfusion/skin health/circulation.

Evenness of pigment increased significantly.

Luminescence of the skin, another measure of smoothness, showed less treatment related variation.

FIG. 11: Wrinkle Measurements (Emerging) for Four Subjects Expressed as Percentage of Initial Pre-Use Value.

Cream use was started day 1 and discontinued after 2 weeks.

Skin Texture and Laxity Changes

The values for emergent wrinkles are representative of skin texture. While emergent wrinkles clearly showed a response to the treatment it was more variable among subjects. As emergent wrinkles are close to the normal texture of skin, they are more prone to confounding factors like skin hydration and measurement error from positioning of the subject in the scanner, etc. The machine used for measurements in this study was calibrated to accept variations in facial position potentially corresponding to +/−5%-8% variation in the wrinkle index [Moritex/BTBP Scanner manufacturer's personal communication].

Pore Health

Use of BiOvaDerm™ Cream appeared to have a direct effect on Pore health parameters but less pronounced effect on complexion. Redness appeared to increase slightly in all groups and did not appear to be affected by cessation of use, the effect likely due to increased microcirculation, (increased circulation to skin surfaces) enabling an exchange of water, oxygen, carbon dioxide, and nutrients, between blood an surrounding tissues, an important component of skin health, increasing luminescence and smoothness.

Changes in Pore Health parameters appeared to be more closely correlated to the use of the cream. Pore inflammation and acne as measured by the diagnostic scanner documented that both decreased during the period of cream use and changed the amount of sebum and affected the smoothing and overall clearing of the skin.

UV Damage

Subjects in the study had sun damage ranging from moderate to severe. In the majority of subjects this remained approximately constant throughout the study and did not appear to be directly affected by the use of BiOvaDerm™ Cream.

Appendix-A

Tables of averaged indices data for different face analysis measurements. Each table contains the data from one of the three groups (Group using the cream for 4 weeks, 2 weeks and one week respectively).

Four Week Use Group

|  | 0 | 1 week | 2 weeks | 3 weeks | 4 weeks | 5 weeks | 6 weeks | 7 weeks | 8 weeks |
|---|---|---|---|---|---|---|---|---|---|
| Averages |  |  |  |  |  |  |  |  |  |
| emerging | 44.25 |  | 34.38 |  | 44.75 |  | 35.88 |  | 43.5 |
| fine | 30.13 |  | 33.25 |  | 32.25 |  | 32 |  | 32.13 |
| deep | 79.88 |  | 74.38 |  | 57.38 |  | 60.5 |  | 69.5 |
| redness | 23.18 |  | 25.9 |  | 24.51 |  | 26.34 |  | 26.16 |
| All Wrinkles | 153.75 |  | 142 |  | 134.38 |  | 128.38 |  | 145.13 |
| Pigment evenness | 13.66 |  | 14.9 |  | 17.01 |  | 15.63 |  | 16.01 |
| Redness | 23.18 |  | 25.9 |  | 25.45 |  | 26.38 |  | 26.09 |
| Luminescence | 25.14 |  | 25.81 |  | 25.81 |  | 25.24 |  | 24.79 |
| Excessive Sebum | 602.75 |  | 661.88 |  | 677 |  | 407.25 |  | 477.75 |
| P. acnes | 1143 |  | 1312.81 |  | 1165.63 |  | 1082.5 |  | 889.88 |
| inflammation | 416.63 |  | 558.13 |  | 615 |  | 477.13 |  | 576.75 |
| Deep Inflammation |  |  |  |  |  |  |  |  |  |
| n = | 7 | 8 | 8 | 8 | 8 | 8 | 8 | 8 | 8 |

Two Week Use Group

| Averaged values for | 0 | 1 | 2 | 3 | 4 | 5 | 6 |
|---|---|---|---|---|---|---|---|
| emerging | | 57.89 | 44.6 | 48.22 | 49.43 | 80 | 53.33 |
| fine | | 39.78 | 27.8 | 35.22 | 33.57 | 56 | 29.33 |
| deep | | 56 | 34.7 | 41.9 | 49.43 | 57.5 | 38.33 |
| redness | | 27.41 | 43 | 35.33 | 28.7 | 11.85 | 25.83 |
| sum wrinkles | | 153.67 | 85.6 | 113.78 | 132.43 | 193.5 | 121 |
| Pigment evenness | | 14.13 | 20.94 | 15.27 | 13.37 | 16.3 | 34.9 |
| Redness | | 23.86 | 27.12 | 26.9 | 29.36 | 11.85 | 35.5 |
| Luminescence | | 24.23 | 44.46 | 26.34 | 27.27 | 28.95 | 55.4 |
| Excessive Sebum | | 521.86 | 402.25 | 412.63 | 417.17 | 11 | 50.5 |
| P. acnes | | 729.57 | 345.5 | 900.5 | 408.83 | 127 | 204.5 |
| inflammation | | 286.07 | 111.25 | 518.56 | 262 | 175 | 264 |
| Deep Inflammation | | | | | | | |
| n = | 1 | 9 | 5 | 9 | 0 | 7 | 2 | 3 |

One Week Use Group

| Averaged values for | 0 | 1 | 2 | 3 | 4 | 5 | 6 |
|---|---|---|---|---|---|---|---|
| emerging | 64.75 | 51.17 | 48.75 | 49 | 73 | 57 | 59.67 |
| fine | 41.25 | 37.5 | 36.25 | 40 | 48.5 | 47 | 37.67 |
| deep | 83 | 67.5 | 60.25 | 81.5 | 97 | 69 | 41 |
| redness | 22.1 | 23.93 | 24.73 | 22.85 | 27.9 | 19.5 | 23.37 |
| sum wrinkles | 189 | 156.17 | 145.25 | 170.5 | 218.5 | 173 | 138.33 |
| Pigment evenness | 16.88 | 3.35 | 17.73 | 22.45 | 25.18 | 17.8 | 25.9 |
| Redness | 11.78 | 0 | 11.6 | 16.6 | 20.08 | 0 | 16.77 |
| Luminescence | 26.4 | 3.02 | 22.88 | 20.75 | 27.3 | 16.6 | 24.43 |
| Excessive Sebum | 259.38 | 38.33 | 278 | 312.5 | 586.25 | 280 | 144.67 |
| P. acnes | 496.25 | 55 | 220 | 220 | 351.25 | 380 | 171.67 |
| inflammation | 421.25 | 51.67 | 228.75 | 267.5 | 236.25 | 250 | 53 |
| Deep Inflammation | 0 | 0 | 0 | 0 | 0 | 0 | 0 |
| n = | 4 | 6 | 4 | 2 | 4 | 1 | 3 |

Appendix-B

Face Diagnostic-Scanning Equipment Used in Study.

Clarity™ Pro Face Scanning System (Moritex Incorporated, USA) Quantitative Analysis of Skin Condition. Clarity™ Pro features early skin condition detection, statistical comparison of before and after treatment images, and product and treatment recommendations. This system is integrated with the Facial Stage, capturing digital, high resolution full face images for recognition and extraction of particular skin condition features. Images are taken in a dual light mode: true white light and safe UV capture.

REFERENCES

1. Baker, J. R. and Balch, D. A., Biochem. J., 82: 352-361, 1962
2. Picard, J., Paul-Gardais, A., and Vedel, M, Biochimica et Biophysica Acta, 320: 427-441
3. Gautron, J., et. al, Connective Tissue Research, 42:255-267, 2001
4. Starcher, B. C. and King, G. S., Connective Tissue Research, 8:53-55, 1980
5. Akagawa, M, et. al, Biochim. Biophys. Acta, 14:151-160, 1999
6. Hincke, M. T., et. al, Matrix Biology, 19:443-453, 2000
7. Deal, C L and Moskowitz, R W, Osteoarthritis, 1999. 25:379-395
8. Matheson, A J and Perry, C M, Drugs Aging. 2003; 20:1041-1060
9. Kevin J Ruff, Anne Winkler, Robert W Jackson, Dale P Devore, Barry W Ritz; Clinical rheumatology. 2009 Apr. 2
10. Sim, J. S., S, Nakai, and W. Guenter, editors—Egg Nutrition and Biotechnology, CABI Publishing, UK 2000 pp 219-232

Example 14

Human Clinical Safety and Efficacy Pilot Study for the Treatment of Knee Associated Musculoskeletal Pain and Stiffness 309 was evaluated for safety and efficacy in the treatment of musculoskeletal pain and flexibility. For study purposes, the knee joint was specified and monitored for the 6 week duration of the study.

An open-label Pilot Study was conducted. Forty-two subjects were recruited and assigned to receive 450 mg of BiovaFlex™ (BIO2) daily for 6 weeks. Subjects were clinically evaluated at established intervals for both effectiveness (pain level and total flexion) and overall health evaluations. Assessments were made at 2, 4 and 6 weeks. Daily online tracking and measurement of the subject's joint pain was recorded via the Western Ontario and McMasters University (WOMAC) Abbreviated Index.

Pain symptoms were reduced 8.25% from base line within 7 days and 16.42% from baseline within 14 days.

Total pain symptoms were reduced 20% from baseline at study end. The average WOMAC value across all subjects fell from 4.61 (baseline) to 3.69 (study end). A reduction of 0.97 or 20.78%. (P<0.0001)

This reduction in absolute pain is significant in that the pain relief overcame the pain increases normally associated with increases in flexion. Improved Knee Functionality in just seven days was 9.191%, and 10.14% from baseline within 14 days.

Relative Knee Functionality improved 37.8% over the course of six weeks.

The safety profile was remarkable with no reported adverse events.

This study shows that BiovaFlex™ (BIO2) is an effective and safe alternative treatment for musculoskeletal pain and stiffness as associated with the knee.

This study was designed to assess the effectiveness of the BiovaFlex™ (BIO2) compositions in the form of an ingestible daily supplement for the treatment of connective tissue and joint pain and discomfort.

Biova LLC in Johnston, Iowa supplied Clinic Testing site with capsules containing BiovaFlex™ (BIO2) in the following: 220 small bottles with 40 capsules, each containing 150 mg of 309. The studied dosage required the consumption of 3 capsules daily to total 450 mg per day. Approximately a two week supply of product per bottle and a 6 week supply of capsules in total were provided to each subject over the duration of the study.

Product Accountability

Supplies delivered to the investigational Clinic were distributed to enrolled subjects at each visit. All supplies were labeled by the Clinic with study date, Clinic name, Supplement name, a number from 1 to 45, with use/dose instructions. Later when the product was supplied to the subject, the subject's identifier code was written on the bottle/jar. The site used a form to document distribution of capsule supplies among subjects. This form was maintained by the investigator. If a subject withdrew from the study, any remaining capsules and capsule containers were collected by the investigator. An accurate account of capsules consumed by each subject in the study was maintained.

Intended Use

The Ingestible Natural Eggshell Membrane supplement of BiovaFlex™ (BIO2) is intended for treatment of the discomfort from connective tissue and knee joint pain. Hydrolyzed eggshell membrane powder of BiovaFlex™ (BIO2) for the study was contained in capsules of 150 mg per capsule. Three (3) capsules are taken by mouth along with water or juice daily.

Study Design

The study was conducted to evaluate the safety and efficacy of BiovaFlex™ (BIO2) ingredient on joint and musculoskeletal pain. Forty two subjects were enrolled in a period of approximately one month and evaluated over the course of 6 subsequent weeks at the test center in Sausalito, Calif. (USA). Selection was based on health and physical evaluations of the subjects along with satisfaction of the inclusion/exclusion criterion set forth in the design of the study. Provision of written informed consent was mandated and obtained prior to enrollment of the subjects in the study. Treatment involved a 450 mg daily dose of BiovaFlex™ (BIO2) soluble eggshell membrane powder via three 150 mg capsules.

Clinic visits and assessments were scheduled at weeks 2, 4 and 6 from subject start. Subject compliance reviews were performed by subject interviews and via monitoring of the subject's online daily diary and WOMAC surveys. Subjects were asked to log questions and or concerns if necessary, in dairies provided to them.

Subjects 18 years of age or older with history of arthritic type joint pain or connective tissue disorder with a reduced range of motion were considered for this study (1). In the selection process the potential subjects clinical history was reviewed and vital signs observed. Selection was based on subject fulfilling the inclusion criteria and disqualifying others based the exclusion criterion. Subjects were included based on Inclusion Criteria. (see below) Subjects acknowledged persistent pain in one or both knees or complained of connective tissue disorder with an assessment score of at least 5, but not more than 9 using the Pain Assessment and Pain Intensity Rating scale. Subjects agreed to replace current pain relief medications with BiovaFlex™ (BIO2) treatment, and female participants agreed to use appropriate birth control for duration of trial.

Subjects were excluded (see detail below) if they had a history of Rheumatoid Arthritis, or were on medications such as methotrexate or immunosuppressive medications. Subjects were asked to refrain from taking any other vitamins or supplements.

Subjects who met all of the eligibility criteria were enrolled to participate. As part of their informed consent subjects were informed of their rights as research participants; the contents of the study, including the procedures involved and the treatment, risk and benefits associated with it, along with any other alternatives available were explained to them. A signed consent form was required and received in order to allow the subjects to participate. A "drop out" log was maintained for any participant who dropped during the duration of the study.

Treatments & Mode of Administration

Subjects were instructed to take a daily dose of three 150 mg (450 mg) processed BiovaFlex™ (BIO2) with juice or water as treatment for their musculoskeletal pain and stiffness. Subjects were evaluated on-site at Week 2, Week 4, and Week 6, and their supplement was replenished till the duration of the next visit. Compliance was tracked using multiple methods including: subject's daily self-assessment diary, to be filled throughout the study period; an online self-assessment electronic questionnaire for pain and stiffness assessed at various range of motions, the WOMAC Assessment and Pain Intensity Rating Scale; or the Center's Study Compliance Phone Line, where subjects identify themselves and record comments regarding their condition. Clinic staff also followed-up with subjects by telephone.

The primary endpoint was to evaluate the effectiveness of 450 mg BiovaFlex™ (BIO2) as a treatment for pain, stiffness, and discomfort for knee associated musculoskeletal disorder. Subjects were evaluated for response to treatment in clinic on Week 2, Week 4, and Week 6. During each clinic visit, review of medical history, physical evaluation, and patient interview provided insight to patient compliance and concerns with respect to the treatment. In addition, subjects were interviewed about situations that have potential to mask symptoms or produce adverse reactions, such as recreational drug abuse or applied-therapeutics or supplements. Effectiveness of response, via knee exam, was determined through pain assessment at rest and on motion as measured on a numerical scale ranging from 0 (no pain) to 10 (worst pain perceivable), along with range of motion as measured using a Goniometer. Signs and Symptoms, e.g. swelling, crepitus, were documented to provide insight into the functionality of knee. The online WOMAC Pain Assessment and Pain Intensity Rating scale was also used to quantify the pain and stiffness and provided a objective tool to evaluate subjects in-between visits. Primary endpoint values were compared to baseline (first visit) to determine efficacy of treatment.

Adverse Effects & Safety Monitoring

The secondary endpoint was to assess the safety of BiovaFlex™ (BIO2) capsules as a treatment option for knee associated musculoskeletal dysfunction. Subjects were also instructed to record any changes in overall health, as well as any discomfort associated with ingestion of the capsules in their self-assessment diaries. An evaluation of heart rate and blood pressure was performed with every visit, to keep track of any potential adverse cardiovascular effect. The subject self-assessment diary was reviewed at each visit and any discomfort of other adverse events recorded was discussed with each subject. Blood Chemistry, hematology, and allergen antibody assays provided valuable insights in any systemic changes that might be of negative consequence to the subject. The testing was performed by a CLIA certified, medical diagnostic laboratory and included non fasting glucose, sodium, potassium, calcium, chloride, carbon dioxide, urea, creatine, alkaline phosphatase, total protein, albumin, globulin, AST, ALT, and total bilirubin. Blood samples from subjects were drawn by certified phlebotomists on initial visit, at week 6 and at varying intervals in between.

Inclusion Criteria

Subject selected were 18 years of age or older; able and willing to give informed consent and attend all evaluation visits. Subject had persistent pain in one or more knee joints or connective tissue with a pain assessment score of at least 5, but not more than 9 using the Pain Assessment and Pain Intensity Rating scale. Subject agreed to take/use BiovaFlex™ (BIO2) compositions to replace current pain relief medications, and was willing to use appropriate birth control for duration of trial if necessary.

Exclusion Criteria

Subjects with Rheumatoid Arthritis, or currently receiving remission-inducing drugs such as methotrexate or immunosuppressive medications in the past 3 months, or using accutane or other skin treatment products were excluded. Subjects using accutane, or other skin treatment drugs or topicals such as Isotretinoin, oral antibiotics, topical antimicrobials, (Azelaic acid, Benzoyl Peroxide, Clindamycin, Erythromycin, Sodium Sulfacetamide, or topical retinoids, like Adapalene, Tazarotene, or Tretinoin were also excluded. Subjects with a persistent pain score >9 using the Pain Assessment and Pain Intensity Rating scale were excluded from the joint study arm but were allowed to participate in the Skin Treatment arm of the study.

In addition, subjects were excluded if they had known allergy to eggs or egg products; were Pregnant or breastfeeding women; unwilling to forgo use of over-the-counter (OTC) treatments for the of the study; involved in any other research study involving an investigational products (drug, device or biologic) or a new application of an approved product, within 30 days of screening; were in poor health, diabetic, high blood pressure, a heart condition, had known problems with bleeding, on medications to stabilize organ function, or moods, or were over-weight by 20% to 25% their maximum desirable weight for their height. Subjects were required to refrain from taking any other vitamins or supplements.

Subjects who met all of the eligibility criteria were invited to participate. Study personnel (clinical investigator or research nurse/coordinator) explained the study to each subject, and reviewed study procedures involved in the treatment, risk and benefits, alternative treatments and his/her rights as a study subject. The subject was given the consent form and allowed as much time as he or she required to read and decide on participation. Subject who decided to participate, were asked to sign the consent form. Subjects who signed the consent form, and provided a medical history and met the inclusion criteria and agreed to the treatment were considered enrolled. Subjects who withdraw after signing the consent but before any study treatment were administered were recorded on a dropout log.

After a Consent Form was signed by the subject, baseline information was collected and the following procedures were conducted:

Review of Medical history. including past or present symptoms, drugs-therapeutic and/or abuse, operations, trauma, joint pain History and Physical exam-functional evaluation (work/walking/swelling/how alleviated) including; knee exam—noting swelling, walk with a limp, needs to use a cane and/or wheelchair, etc.

Scoring of joint pain or connective tissue pain using the WOMAC Pain Assessment and Pain Intensity Rating Scale. Determine range of motion of effected joint(s), a pain reduction of 0.97 or 20.78% ($P<0.0001$)

Concomitant medications.

Blood Chemistry, CBC, blood pressure and heart rate.

Study Schedule:

Table One. S=Supplement T=Topical.

Results

A total of forty-two subjects were recruited and enrolled in the trial with respect to the selection criteria discussed above.

The average drop in pain over the study period across all individuals was almost one full point on the WOMAC scale: 0.97 (4.61 (baseline) to 3.69, a pain reduction of 20.78% ($P<0.0001$) (study end)). (Also see diary data for some of the more dramatic effects) A full point decrease in absolute pain is substantial because it means that even as degree of flex increases, the pain relief is so substantial that it outweighs the upward pressure on pain due to increase in flex. The functionality measurements show increases in overall functionality of the knees given both flex and pain.

Treatment with BiovaFlex™ demonstrated:

In First 10 days of Treatment Pain Is Reduced an Average of 23.77% in all Subjects:

| Walking on flat surface - pain | Going on up or down stairs - pain | At night while in bed - pain | While sitting or laying - pain | While standing - pain | Average for All |
|---|---|---|---|---|---|
| 23.64% | 24.69% | 18.92% | 20.00% | 31.58% | 23.77% |

The subject self-report data show that over a ten day period pain was reduced by 23.64% for walking on a flat surface, 24.69% for going up or down stairs, 18.92% while in bed, 20% while sitting or laying, and 31.58% while standing. The average reduction in pain for all subjects over all measured activities was 23.77%. This implies, if the set of subjects is truly representative of the set of consumers of the product, that a reduction in pain of 18.92% to 31.58% with consistent consumption of the intervention product is not inconsistent with the data. This analysis is based on average responses from survey data reported by subjects based on the WOMAC pain scale.

Toxicity and Adverse Effects

Medical Histories Review

Twelve subjects dropped/no showed from the study due to a combination of personal reasons, exclusionary or precautionary measures taken on by clinical staff.

Dropouts:

| | CODE | REASON |
|---|---|---|
| 1 | LR 40 | Blood Pressure - slight- hyperactive |
| 2 | JL 30 | Blood Pressure - white coat |
| 3 | JH 48 | Personal |
| 4 | PT 39 | On medication for Blood Pressure |
| 5 | AG 4 | Personal |
| 6 | TFB 3 | Egg Allergy |
| 7 | CM 51 | Egg Allergy |
| 8 | AS 44 | Personal (drug usage) |
| 9 | DW 50 | Due to no show |
| 10 | DJ 49 | Personal (Surgery) |
| 11 | SM 45 | Due to no show |
| 12 | AL 1 | Personal (family) |

Blood Analysis Results Summary

As part of the design to ascertain safety and efficacy, an average of two blood samples were taken from each subject. Blood samples were collected at baseline at the end of the study. In addition, sampling was done at varying intervals throughout the treatment period to monitor allergies or toxicity. As a part of the safety protocol, blood chemistry, hematology, and allergen antibody assays were performed. The testing was performed by a CLIA certified, medical diagnostic reference laboratory.

The blood chemistry analysis included non fasting glucose, sodium, potassium, chloride, carbon dioxide, urea nitrogen, creatinine, calcium, alkaline phosphatase, total protein, albumin, and globulin. In addition, AST, ALT and total bilirubin were tested to monitor liver function.

A complete blood cell count was performed to monitor general system function. The hematology analysis included a hematocrit and hemoglobin level, red cell, white cell, and platelet counts, as well as cell morphology.

A slight overall rise in blood chloride and urea nitrogen were noted, but were still within the reference range at the study completion.

Although there was an occasional nonspecific result that fell outside the reference range, all results were predominantly well within normal ranges. In review of analytical data reported, there was no significant change from baseline beyond the normal variations that are expected. There was no negative effect nor toxicity observed in blood chemistry analysis. Hematocrit and hemoglobin concentration showed little change and there was no abnormal blood cell morphology. Furthermore, none of the participants showed any significant increase in IgE antibodies to egg allergens.

Effectiveness Analysis

The following will be a discussion of the data obtained from the patient diaries and the flexibility/pain measurement data. These data are used to analyze the overall effectiveness of the BiovaFlex™ product on subjects over time. All data were collected according to guidelines detailed by the WOMAC™ scale. (cite: http://www.womac.org/womac/womac_userguide.htm) Diary data comprises the self-report segment of the study, while the Pain/Flexibility data comprise corroborating medical measurements.

Subject Self-Report Logs

In addition to the data collected from subject blood work, subjects were required to note protocol compliance in an online electronic journal on a daily basis. Data collected include time, date, patient information, and pill consumption behavior. In addition, several questions from the WOMAC scale were presented, including the level of pain (mild, moderate, severe, extreme) for the following activities: walking on a flat surface, going up or down stairs, at night while in bed, while sitting, and while standing. Space was left for comments to allow comparison of response with subject qualitative notes. Subject self-report logs served as positive reinforcement for protocol compliance. Further, the tabulation of this data illustrates some of the evolution of subject responses over time in a more granular fashion. Summary tabulations of results are displayed in Table Two below.

TABLE TWO

Subject self report (online diary) data. The data show the changes from the inception period to the end period. Numbers denote the percentage of total individuals listing the response (none, mild, moderate, severe, extreme) on the pain questionnaire.
Subject Self-Report Log Data

| Date Range | Factor | None (%) | Mild (%) | Mod. (%) | Severe (%) | Extreme (%) |
|---|---|---|---|---|---|---|
| April | 5 | 46.39 | 30.93 | 20.62 | 0.00 | 0.00 |
| | 4 | 54.64 | 34.02 | 9.28 | 0.00 | 0.00 |
| | 3 | 77.32 | 21.65 | 0.00 | 0.00 | 0.00 |
| | 2 | 39.18 | 38.14 | 20.62 | 0.00 | 0.00 |
| | 1 | 34.02 | 47.42 | 16.49 | 0.00 | 0.00 |
| January | 5 | 40.61 | 29.95 | 26.90 | 1.02 | 0.00 |
| | 4 | 45.18 | 36.04 | 13.20 | 4.06 | 0.51 |
| | 3 | 55.84 | 24.87 | 15.74 | 3.05 | 0.00 |
| | 2 | 27.92 | 28.43 | 27.92 | 13.71 | 2.03 |
| | 1 | 39.09 | 30.96 | 25.89 | 3.55 | 0.00 |

Key to factors:
1 = Walking on flat surface - pain;
2 = Going on up or down - pain;
3 = At night while in bed - pain;
4 = While sitting or laying - pain;
5 = While standing - pain.

A simple analysis of diary data over time showed that a smaller proportion of subjects showed pain in each question as participation in the study changed. The percentage of subjects suffering from no pain in factor five went from 40.61% to 46.39%, in six week, showing a potentially positive redistribution from higher pain groups to lower pain groups. The percentage of subjects in the worst pain groups declined to zero at the end of the study.

TABLE THREE

Subject self-report (online diary) data.

| Factor | None (%) | Mild (%) | Mod. (%) | Severe (%) | Extreme (%) |
|---|---|---|---|---|---|
| 5 | 12.45 | 3.168445 | −30.45 | TR | TR |
| 4 | 17.31 | −5.93768 | −42.24 | TR | TR |
| 3 | 27.78 | −14.873 | TR | TR | TR |
| 2 | 28.73 | 25.45884 | −35.40 | TR | TR |
| 1 | −14.90 | 34.71109 | −57.00 | TR | TR |

This chart documents the changes in the percentages of subjects reporting various levels of pain from the inception of the study in January to the end of the study in April. The higher categories show decline while the "None" category shows increase in all but one area.

As the data in Table Three show, the "Severe" and "Extreme" categories are completely vacated by the end of the study. The "Moderate" pain category has shown significant decline. Declines are seen in the mild category and the "None" category has seen increases for all except factor one. The bulk of increase for factor 1 appears to have been distributed with the "Mild" category. This evidence is consistent with the hypothesis that the BiovaFlex™ (BIO2) supplement has a positive effect on the reduction of knee pain.

Direct Flexibility and Pain Scale Measurements

Supplement effectiveness evaluations were carried out at week 2, week 4, and week 6 following initiation of treatment. During the follow up evaluation visits the clinical investigators reviewed the subject's diary and conducted a pain assessment using the pain assessment and pain intensity rating scale. The investigators also conducted manual range of motion assessments on the subject's knee(s). Another pain assessment using the WOMAC pain assessment and pain intensity rating scale was also made during range of motion measurements.

The mean baseline pain assessment score was calculated for all subjects. The change in pain assessment score for each treatment was calculated and then averaged across the subject population at week 2, 4, and 6 of the evaluation.

A challenge when measuring the effects of knee pain is that there is natural confounding in the end measured results: the knee's range of motion, i.e. degrees of flexibility and subject' pain level at specific measurements within that range of motion. The data set is essentially subject to double variables. Therefore, a simple analysis of either measurement may show a fallacious positive or negative relationship between the measurement targets and the intervention material. In order to compensate for these double variables, a couple of simple formulae have been developed to enable comparisons of data averages.

The formulae are as follows:

$$\text{Relative Functionality (Pop. Average): } Y = \frac{1}{n}\sum_i^n \frac{(x_{1i}/90)}{((10-x_{2i})/(10))} \quad x_{2i} \neq 10 \quad \text{Eq. 1}$$

This calculates the relative increase range of motion of leg given pain, or "Relative Functionality" of the subjects knees. It is simply the corrected ratio of range of leg motion compared to the inverse of the level of pain, to denote pain-related functionality. The end-result is a comparison of percentages put in the same numerical terms, which delineates the degree to which increases in total functionality can be attributed to increased range of leg motion.

$$\text{Total Functionality (Pop. Average): } Y = \frac{1}{n}\sum_i^n (x_{1i}/90) + [(10-x_{2i})/10)] \quad \text{Eq. 2}$$

This calculates the total increase range of motion of leg given pain level, or "Total Functionality" of the subjects knees. It is the corrected ratio of range of leg motion added to the inverse of the level of pain, to denote pain-related functionality. The result is a corrected version of the total change in subject knee functionality over the study period.

In both equations please note the following: y denotes the estimated outcome measure, n is the number of subjects, i is the ith subject, $x_{1i}$ is the degree of movement for subject i, $x_{2i}$ is the measurement on the pain scale for subject i, 90 is the total number of degrees of movement for a totally functional knee and 10 is the total for the pain scale. As 10 is the highest level of pain, $10-x_{2i}$ denotes the pain-related functionality of the subject.

| | Baseline | Comparison | Total Change |
|---|---|---|---|
| Relative Functionality | 1.509699 | 2.080397 | 37.8% |
| Total Functionality | 1.135095 | 1.351762 | 19.1% |

Source: This chart denotes population averages tabulated as per Eq. 1, Eq2.

The data obtained are supplied in the chart above. The data illustrate noticeable improvements over the three sampling time points, week 2, 4 & 6. The interpretation of the information in the chart above is as follows: relative flexibility fluctuated in the sample by 37.8%. This means that of the amount of functionality gained, 37.8% as calculated, can be attributed to the relative increases in degree of knee bend concurrent to the relative reductions in pain as realized within this range of motion. (Also, it is worth noting that the p-values for all of the values are p<0.0001, allowing for the rejection of the null hypothesis.) This is consistent with the observation that as the intervention takes effect, the subject is able to increase his/her angle of motion to the point of pain tolerance. The increase in total functionality means that knee functionality taking into account both angle of motion and pain level have increased by a total of 19.1%. These calculations are based on averages documented above computed on the sample of individuals provided in the study.

Discussion-Conclusion:

Chronic debilitating knee pain and dysfunction is an extremely common disorder and is a significant cause of dysfunction in individuals of all age groups. This study was designed to evaluate the safety and efficacy of BiovaFlex™ as a treatment option for subjects suffering from knee associated musculoskeletal dysfunction.

The study concludes that BiovaFlex™ is a viable option for treatment of knee and musculoskeletal disorder in that it has proven effectiveness in joint related symptoms and has been shown to be safe, with no reported adverse effects. The absence of reported adverse events with BiovaFlex™ may prove it to be more advantageous as a remedy than the traditional route of joint relief with NSAIDS, with their serious side effects.

Subjects have shown significant improvement in symptoms relative to the short duration of the study. (an average drop in pain over the study period across all individuals was almost one full point on the WOMAC scale: 0.97, in just the first 10 days of treatment pain was reduced an average of 23.77% in all subjects.

As the data in Table 3 shows, in this 45 day study, there is a significant decline in pain of moderate level with redistribution into lower pain groups. Relative functionality of 37.8% denotes a marked improvement in overall flexibility. This shows that range of motion has improved with subjects showing greater degrees of flexion. Total functionality of 19.1%, although not as marked as relative functionality, is nevertheless significant given the short duration of the study. This total functionality denotes improvement in symptoms on joint usage (e.g. walking, climbing stairs). It is evident from these results that use of BiovaFlex™ does have potential as a treatment for symptomatic joint relief in knee musculoskeletal dysfunction, more so with its absence of reported adverse effect. This is significant especially when dealing with a condition that requires long-term treatment.

The improvements in the signs and symptoms may in part be related to the Glycosaminoglycans (GAGs), which are constituents of the BiovaFlex™ Glycosaminoglycans (GAGs), the class of amino sugars to which Hyaluronic acid, chondroitin-sulfate and glucosamine belong to, are an integral part of the amorphic ground substance that constitutes the extracellular matrix of connective tissues, for example articular cartilage. GAGS have highly charged side groups that render them extremely hydrophilic, thus attracting large volume of water, which imparts the characteristic turgor of supportive tissues.

REFERENCES

1. Baker, J. R. and Balch, D. A., Biochem. J., 82: 352-361, 1962
2. Picard, J., Paul-Gardais, A., and Vedel, M, Biochimica et Biophysica Acta, 320: 427-441
3. Gautron, J., et. al, Connective Tissue Research, 42:255-267, 2001
4. Starcher, B. C. and King, G. S., Connective Tissue Research, 8:53-55, 1980
5. Akagawa, M, et. al, Biochim. Biophys. Acta, 14:151-160, 1999
6. Hincke, M. T., et. al, Matrix Biology, 19:443-453, 2000
7. Deal, C L and Moskowitz, R W, Osteoarthritis, 1999. 25:379-395
8. Matheson, A J and Perry, C M, Drugs Aging. 2003; 20:1041-1060

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention. In particular, it is to be understood that the present invention contemplates variations in the proteinaceous material, process parameters, including temperature, time, pH, salt (ash), separation techniques, drying or preparation techniques, and proteins of interest.

What is claimed is:

1. A method of treating a disease, disorder or condition caused by oxidative stress from reactive oxygen species (ROS) comprising administering to an individual in need thereof an effective amount of a composition wherein the composition is a solubilized protein composition obtained from avian eggshell membrane without the use of proteolytic enzymes or cross-linking agents, wherein the composition is essentially odor-free, has an ash content of less than 20% by weight of the composition, and comprises a solubilized protein content of at least 80% by weight of the composition, wherein the composition comprises a mixture of solubilized proteins selected from the group consisting of Type I collagen, Type V collagen, Type X collagen, elastin, lysozyme, ovotransferrin, desmosine, and/or B—N-acetylglucosaminidase, wherein the solubilized proteins are undenatured and retain biological activity, and wherein the solubilized protein composition is obtained by a process comprising:
   (a) exposing the eggshell membrane to a sufficient amount of a basic solution for a sufficient length of time and temperature for hydrolysis of the eggshell membrane to occur so as to produce a solution containing solubilized proteins whereby the solubilized proteins are undenatured and retain biological activity;
   (b) cooling the solution containing the solubilized proteins to a temperature of from about 2 degrees Celsius to about 18 degrees Celsius;
   (c) centrifuging the cooled solubilized protein solution to form a supernatant liquid;
   (d) removing ash from the supernatant liquid so that the supernatant liquid has a conductivity of less than 5 milliSiemens/cm; and
   (e) recovering the solubilized protein composition from the supernatant liquid obtained in step (d) by filtering the supernatant liquid through a membrane that has a molecular cutoff of at least 100 kDa to obtain a retentate protein mixture containing solubilized proteins having a molecular weight of greater than 100 kDa and/or a permeate protein mixture containing solubilized proteins having a molecular weight of less than 100 kDa.

2. The method of claim 1 wherein the disease, disorder or condition is a cosmetic condition or dermatological disorder in the individual.

3. The method of claim 1 wherein the disease, disorder or condition is associated with joint health, a wound, or a skin condition.

4. The method of claim 3 wherein the administering comprises topically applying to skin of the individual an effective amount of the composition.

5. The method of claim 4, wherein the skin being treated has less wrinkles, less blocked pores, uneven pigmentation, skin roughness, acne, and more perfusion or vascularization as compared to skin of an individual not receiving the composition.

6. The method of claim 3 wherein the wound has enhanced healing as compared to a wound in an individual not receiving the composition.

7. The method of claim 1 wherein the disease, disorder or condition is associated with a mitochondrial disorder in the individual.

8. The method of claim 1 further comprising treating a disease, disorder or condition associated with inflammation in an individual.

9. The method of claim 1 wherein the administering is selected from the set consisting of intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesiculully, mucosally, intrapericardially, intraumbilically, intraocularally, orally, topically, locally, inhalation (e.g., aerosol inhalation), injection, infusion, and continuous infusion to the individual.

10. A method of treating a disease, disorder or condition associated with inflammation and/or oxidative stress comprising administering to an individual in need thereof an effective amount of composition of solubilized eggshell membrane; wherein the composition is a solubilized protein composition obtained from avian eggshell membrane without the use of proteolytic enzymes or cross-linking agents, wherein the composition is essentially odor-free, has an ash content of less than 20% by weight of the composition, and comprises a solubilized protein content of at least 80% by weight of the composition, wherein the composition comprises a mixture of solubilized proteins selected from the group consisting of Type I collagen, Type V collagen, Type X collagen, elastin, lysozyme, ovotransferrin, desmosine, and/or B—N-acetylgluosaminidase, wherein the solubilized proteins are undenatured and retain biological activity, and wherein the solubilized protein composition is obtained by a process comprising:

(a) exposing the eggshell membrane to a sufficient amount of a basic solution for a sufficient length of time and temperature for hydrolsis of the eggshell membrane to occur so as to produce a solution containing solubilized proteins whereby the solubilized proteins are undenatured and retain biological activity;

(b) cooling the solution;

(c) centrifuging the cool solubilized protein solution to form a supernatant liquid;

(d) removing ash from the supernatant liquid; and (e) recovering the solubilized protein composition from the supernatant liquid obtained in step (d) by filtering the supernatant liquid through a membrane that has a molecular cutoff of at least 100 kDa to obtain a retentate protein mixture containing solubilized proteins having a molecular weight og greater than 100 kDa and/or a permeate protein mixture containing solubilized proteins having a molecular weight of less than 100 kDa.

11. The method of claim 10 wherein the disease, disorder or condition is selected from a set consisting of a joint health condition, a dermatological disorder, a cosmetic condition, a wound, a mitochondrial disorder, and an inflammation.

12. The method of claim 10 wherein the disease, disorder, or condition is associated with inflammation in the individual.

* * * * *

UNITED STATES PATENT AND TRADEMARK OFFICE
CERTIFICATE OF CORRECTION

PATENT NO. : 8,425,943 B2
APPLICATION NO. : 13/484537
DATED : April 23, 2013
INVENTOR(S) : Ronald E. Strohbehn et al.

It is certified that error appears in the above-identified patent and that said Letters Patent is hereby corrected as shown below:

In the Claims:

Col. 66, Claim 10, Line 14:
DELETE after weight "og"
ADD after weight --of--

Signed and Sealed this
Eleventh Day of June, 2013

Teresa Stanek Rea
*Acting Director of the United States Patent and Trademark Office*